(12) United States Patent
Gersbach et al.

(10) Patent No.: US 10,711,256 B2
(45) Date of Patent: Jul. 14, 2020

(54) GENETIC CORRECTION OF MUTATED GENES

(71) Applicant: Duke University, Durham, NC (US)

(72) Inventors: Charles Gersbach, Durham, NC (US); David Ousterout, Durham, NC (US)

(73) Assignee: Duke University, Durham, NC (US)

( * ) Notice: Subject to any disclaimer, the term of this patent is extended or adjusted under 35 U.S.C. 154(b) by 127 days.

(21) Appl. No.: 15/634,425

(22) Filed: Jun. 27, 2017

(65) Prior Publication Data

US 2017/0298331 A1    Oct. 19, 2017

Related U.S. Application Data

(62) Division of application No. 14/397,420, filed as application No. PCT/US2013/038536 on Apr. 26, 2013, now Pat. No. 9,738,879.

(60) Provisional application No. 61/639,227, filed on Apr. 27, 2012.

(51) Int. Cl.
| | |
|---|---|
| *C12N 9/22* | (2006.01) |
| *C12N 9/14* | (2006.01) |
| *A61K 48/00* | (2006.01) |
| *C07K 14/47* | (2006.01) |
| *C12N 15/90* | (2006.01) |
| *C12N 15/11* | (2006.01) |
| *A61K 38/00* | (2006.01) |

(52) U.S. Cl.
CPC .............. *C12N 9/22* (2013.01); *A61K 48/005* (2013.01); *C07K 14/4708* (2013.01); *C12N 15/111* (2013.01); *C12N 15/907* (2013.01); *C12N 2310/20* (2017.05); *C12N 2320/30* (2013.01)

(58) Field of Classification Search
None
See application file for complete search history.

(56) References Cited

U.S. PATENT DOCUMENTS

| | | | |
|---|---|---|---|
| 5,593,972 A | 1/1997 | Weiner et al. | |
| 5,773,700 A | 6/1998 | Van Grinsven et al. | |
| 5,962,428 A | 10/1999 | Carrano et al. | |
| 9,890,364 B2 | 2/2018 | Joung et al. | |
| 2004/0175727 A1 | 9/2004 | Draghia-Akli et al. | |
| 2007/0185042 A1* | 8/2007 | Tsai ................... | C12N 15/1137 514/44 A |
| 2011/0197290 A1 | 8/2011 | Fahrenkrug et al. | |
| 2011/0263682 A1 | 10/2011 | De Kimpe et al. | |
| 2011/0301073 A1 | 12/2011 | Gregory et al. | |
| 2013/0274129 A1 | 10/2013 | Katzen et al. | |
| 2014/0179006 A1 | 6/2014 | Zhang | |
| 2014/0234975 A1 | 8/2014 | Silva et al. | |
| 2014/0356956 A1 | 12/2014 | Church et al. | |
| 2015/0045413 A1 | 2/2015 | De Visser et al. | |
| 2015/0056705 A1 | 2/2015 | Conway et al. | |
| 2015/0079064 A1 | 3/2015 | Gersbach et al. | |
| 2015/0159178 A1 | 6/2015 | Green et al. | |

FOREIGN PATENT DOCUMENTS

| | | |
|---|---|---|
| CA | 2749305 | 7/2010 |
| JP | 2015-534817 A | 12/2015 |
| JP | 2016-521452 A | 7/2016 |
| JP | 2016-521975 A | 7/2016 |
| JP | 2016-523082 A | 8/2016 |
| WO | WO 93/024640 | 12/1993 |
| WO | WO 94/016737 | 8/1994 |
| WO | WO 01/83783 | 11/2001 |
| WO | WO 2008/006028 | 1/2008 |
| WO | WO 2011/036640 | 3/2011 |
| WO | WO 2011/154427 | 12/2011 |
| WO | WO 2013/163628 | 10/2013 |
| WO | 2014/081855 A1 | 5/2014 |
| WO | 2014/093595 A1 | 6/2014 |

OTHER PUBLICATIONS

United States Patent Office Action for U.S. Appl. No. 14/895,316 dated Mar. 21, 2018 (8 pages).
United States Patent Office Action for U.S. Appl. No. 15/789,348 dated Feb. 22, 2018 (14 pages).
European Patent Office Action for Application No. 13781472.9 dated Jan. 4, 2018 (4 pages).
United States Patent Office Action for U.S. Appl. No. 15/789,348 dated Aug. 13, 2018 (15 pages).
Aartsma-Rus, A. et al., "Antisense-mediated exon skipping: a versatile tool with therapeutic and research applications," RNA 13, 2007, 1609-1624.
Aartsma-Rus, A. et al., "Exploring the frontiers of therapeutic exon skipping for Duchenne muscular dystrophy by double targeting within one or multiple exons," Mol Ther, 2006, 14:401-407.
Aartsma-Rus, A. et al., "Theoretic applicability of antisense-mediated exon skipping for Duchenne muscular dystrophy mutations," Hum Mutat, 2009, 30:293-299.
Adler, A.F. et al., "Nonviral direct conversion of primary mouse embryonic fibroblasts to neuronal cells," Molecular therapy, 2012 Nucleic acids 1, e32.
Aiuti, A. et al., "Lentiviral hematopoietic stem cell gene therapy inpatients with Wiskott-Aldrich syndrome," Science, 2013, 341(6148): p. 1233151.
Anders, S. et al., "Differential expression analysis for sequence count data," Genome biology 11, 2010, R106.
Anguela, X. M. et al., "Robust ZFN-mediated genome editing in adult hemophilic mice," Blood, 2013, 122:3283-3287.
Aoki, Y. et al., "Bodywide skipping of exons 45-55 in dystrophic mdx52 mice by systemic antisense delivery," Proc Natl Acad Sci USA, 2012, 109:13763-13768.
Bartsevich, V. V. et al., "Engineered zinc finger proteins for controlling stem cell fate," Stem Cells 21, 2003, 632-637.

(Continued)

*Primary Examiner* — Manjunath N Rao
*Assistant Examiner* — Samuel W Liu
(74) *Attorney, Agent, or Firm* — Michael Best & Friedrich LLP

(57) ABSTRACT

Disclosed herein are transcription activator-like effector nuclease (TALEN)-related compositions and methods of using said TALENs for correcting mutant genes.

16 Claims, 17 Drawing Sheets

Specification includes a Sequence Listing.

(56) References Cited

OTHER PUBLICATIONS

Beerli, R. R. et al., "Chemically regulated zinc finger transcription factors," J Biol Chem, 2000, 275(42): p. 32617-32627.
Beerli, R.R. et al., "3rd Engineering polydactyl zinc-finger transcription factors," Nat Biotechnol 20, 2002, 135-141.
Beerli, R.R. et al., "3rd Positive and negative regulation of endogenous genes by designed transcription factors," Proc Natl Acad Sci U S A 97, 2000, 1495-1500.
Beerli, R.R. et al., "3rd Toward controlling gene expression at will: specific regulation of the erbB-2/HER-2 promoter by using polydactyl zinc finger proteins constructed from modular building blocks," Proc Natl Acad Sci U S A 95, 1998, 14628-14633.
Beltran, A. et al., "Re-activation of a dormant tumor suppressor gene maspin by designed transcription factors," Oncogene 26, 2007, 2791-2798.
Benedetti, S. et al., "Repair or Replace? Exploiting Novel Gene and Cell Therapy Strategies for Muscular Dystrophies," FEBS Journal (2013).
Berghella, L. et al., "Reversible immortalization of human myogenic cells by site-specific excision of a retrovirally transferred oncogene," Human gene therapy 10, 1999, 1607-1617.
Bhakta, M. S. et al., "Highly active zinc-finger nucleases by extended modular assembly," Genome Res, 2013, 530-538.
Bidou, L. et al., "Sense from nonsense: therapies for premature stop codon diseases," Trends in Molecular Medicine 18, 2012, 679-688.
Blancafort, P. et al., "3rd Scanning the human genome with combinatorial transcription factor libraries," Nat Biotechnol 21, 2003, 269-274.
Boch, J. et al., "Breaking the code of DNA binding specificity of TAL-type III effectors," Science 326, 2009, 1509.
Bowles, D. E. et al., "Phase 1 Gene Therapy for Duchenne Muscular Dystrophy Using a Translation Optimized AAV Vector," Molecular Therapy 20, 2012, 443-455.
Brunet, E. et al., "Chromosomal translocations induced at specific loci in human stem cells," Proc Natl Acad Sci USA, 2009, 106:10620-10625.
Buler et al. Energy-sensing factors coactivator peroxisome proliferator-activated receptor gamma coactivator 1-alpha (PGC-1 alpha) and AMP-activated protein kinase control expression of inflammatory mediators in liver. The Journal of Biological Chemistry, vol. 287, No. 3, pp. 1847-1860, Jan. 13, 2012.
Bultmann, S. et al., "Targeted transcriptional activation of silent oct4 pluripotency gene by combining designer TALEs and inhibition of epigenetic modifiers," Nucleic Acids Res 40, 2012, 5368-5377.
Cerletti, M. et al., "Highly efficient, functional engraftment of skeletal muscle stem cells in dystrophic muscles," Cell 134, 2008, 37-47.
Cermak, T. et al., "Efficient design and assembly of custom TALEN and other TAL effector-based constructs for DNA targeting," Nucleic Acids Res 30, 2011, e82.
Chapdelaine, P. et al., "Meganucleases can restore the reading frame of a mutual dystrophin," Gene therapy 17, 2010, 846-858.
Cheng, A. W. et al., "Multiplexed activation of endogenous genes by CRISPR-on, an RNA-guided transcriptional activator system," Cell Res, 2013, 23(10): p. 1163-1171.
Cho, S. W. et al., "Analysis of off-target effects of CRISPR/Cas-derived RNA-guided endonucleases and nickases," Genome Res, 2014, 24:132-141.
Cho, S.W. et al., "Targeted genome engineering in human cells with the Cas9 RNA-guided endonuclease," Nat Biotechnol 31, 2013, 230-232.
Christian, M. et al., "Targeting DNA double-strand breaks with TAL effector nucleases," Genetics 186, 2010, 757-761.
Cirak, S. et al., "Exon skipping and dystrophin restoration inpatients with Duchenne muscular dystrophy after systemic phosphorodiamidate morpholino oligomer treatment: an open-label, phase 2, dose-escalation study," Lancet 378, 2011, 595-605.
Cong, L. et al., "Multiplex Genome Engineering Using CRISPR/Cas Systems," Science 339, 2013, 819-823.
Cornu et al., "Quantification of zinc finger nuclease-associated toxicity," Meth Mol Biol, 2010, 649:237-245.
Cornu, T. I. et al., "DNA-binding specificity is a major determinant of the activity and toxicity of zinc-finger nucleases," Mol Ther, 2008, 16:352-358.
Cradick, T. J. et al., "CRISPR/Cas9 systems targeting beta-globin and CCR5 genes have substantial off-target activity," Nucleic Acids Res, 2013, 41(20): p. 9584-92.
Darabi, R. et al., "Human ES-and iPS-derived myogenic progenitors restore dystrophin and improve contractility upon transplantation in dystrophic mice," Cell Stem Cell 10, 2012, 610-619.
Dezawa, M. et al., "Bone marrow stromal cells generate muscle cells and repair muscle degeneration," Science Signaling 309, 2005, 314.
Ding, Q. et al., "A TALEN Genome-Editing System for Generating Human Stem Cell-Based Disease Models," 2013, Cell Stem Cell 12, 238-251.
Ding, Q. et al., "Enhanced efficiency of human pluripotent stem cell genome editing through replacing TALENs with CRISPRs," Cell Stem Cell, 2013, 12:393-394.
Doyle, E. L. et al., "TAL Effector-Nucleotide Targeter (TALE-NT) 2.0: tools for TAL effector design and target prediction," Nucleic Acids Res 40, 2012, W117-122.
Doyon, Y. et al., "Enhancing zinc-finger-nuclease activity with improved obligate heterodimeric architectures," Nat Methods 8, 2010, 74-79.
Edelstein et al. Gene therapy clinical trials worldwide 1989-2004—an overview. J. Gene Med. vol. 6, pp. 597-602, 2004.
Esvelt et al., "Orthogonal Cas9 proteins for RNA-guided gene regulation and editing," Nature Methods 2013, 10(11): p. 1116-21.
Farinelli, G. et al., "Lentiviral vectors for the treatment of primary immunodeficiencies," J Inherit Metab Dis, 2014.
Farzadfard, F. et al., "Tunable and Multifunctional Eukaryotic Transcription Factors Based on CRISPR/Cas," ACS Synth Biol, 2013, 604-613.
Flanigan, K. M. et al., "Mutational spectrum of DMD mutations in dystrophinopathy patients: application of modern diagnostic techniques to a large cohort," Human mutation 30, 2009, 1657-1666.
Fonfara, I. et al., "Phylogeny of Cas9 determines functional exchangeability of dual-RNA and Cas9 among orthologous type II CRISPR-Cas systems," Nucleic Acids Res, 2013.
Fu, Y., et al., "High-frequency off-target mutagenesis induced by CRISPR-Cas nucleases in human cells," Nat Biotechnol, 2013, 31(9): p. 822-6.
Fu, Y., et al., "Improving CRISPR-Cas nuclease specificity using truncated guide RNAs," 2014, Nat Biotechnol 32, 279-284.
Gaj, T. et al., "Targeted gene knockout by direct delivery of zinc-finger nuclease proteins," Nature Methods, 2012.
Gaj, T. et al., "ZFN, TALEN, and CRISPR/Cas-based methods for genome engineering," Trends Biotechnol, 2013, 31:397-405.
Garg, A. et al., "Engineering synthetic TAL effectors with orthogonal target sites," Nucleic Acids Res 40, 2012, 7584-7595.
Gertz, J. et al., "Transposase mediated construction of RNA-seq libraries," Genome Res 22, 2012, 134-141.
Goemans, N. M. et al., "Systemic administration of PRO051 in Duchenne's muscular dystrophy," The New England journal of medicine 364, 2011, 1513-1522.

(56) References Cited

OTHER PUBLICATIONS

Gou, D. et al., "A novel approach for the construction of multiple shRNA expression vectors," J Gene Med, 2007, 9(9): p. 751-63.
Graslund, T. et al., "3rd Exploring strategies for the design of artificial transcription factors: targeting sites proximal to known regulatory regions for the induction of gamma-globin expression and the treatment of sickle cell disease," J Biol Chem 280, 2005, 3707-3714.
Gregorevic, P. et al., "Systemic delivery of genes to striated muscles using adeno-associated viral vectors," Nat Med, 2004, 10:828-834.
Guo, J. et al., "Directed evolution of an enhanced and highly efficient FokI cleavage domain for zinc finger nucleases," J Mol Biol, 2010.
Guschin, D. Y. et al., "A rapid and general assay for monitoring endogenous gene modification," Methods Mol Biol 649, 2010, 247-256.
Hockemeyer, D. et al., "Efficient targeting of expressed and silent genes in human ESCs and iPSCs using zinc-finger nucleases," Nat Biotechnol, 2009, 27(9): p. 851-7.
Hockemeyer, D. et al., "Genetic engineering of human pluripotent cells using TALE nucleases," Nat Biotechnol 29, 2011, 731-734.
Hoffman, E. P. et al., "Dystrophin: the protein product of the Duchenne muscular dystrophy locus," Cell, 1987, 51:919.
Hou, Z. et al., "Efficient genome engineering in human pluripotent stem cells using Cas9 from Neisseria meningitidis," Proc Natl Acad Sci USA, 2013, 110:15644-15649.
Hsu et al. (2012) "Dissecting Neural Function Using Targeted Genome Engineering Technologies", ACS Chem. Neurosci., pp. 603-610.
Hsu et al., "DNA targeting specificity of RNA-guided Cas9 nucleases," Nature Biotechnology 31, 2013, 827-832 doi:10.1038/nbt.2647.
Humbert et al., "Targeted gene therapies: tools, applications, optimization", Critical Reviews in Biochemistry and Molecular Biology, CRC Press, vol. 47, No. 3, Apr. 2012, pp. 264-281.
Hwang, W. Y. et al., "Efficient genome editing in zebrafish using CRISPR-Cas system," Nat Biotechnol, 2013, 31(3):p. 227-9.
Jinek, M. et al., "A programmable dual-RNA-guided DNA endonuclease in adaptive bacterial immunity," Science 337, 2012, 816-821.
Jinek, M. et al., "RNA-programmed genome editing in human cells. eLife 2," e00471, 2013.
Jinek, M. et al., "Structures of Cas9 endonucleases reveal RNA-mediated conformational activation," Science, 2014, 343(6176): p. 1247997.
Joung, J. K. et al., "TALENs: a widely applicable technology for targeted genome editing," Nature Reviews Molecular Cell Biology 14, 2013, 49-55.
Kayali et al., "Site-directed gene repair of the dystrophin gene mediated by PNA-ssODNs," Human Molecular Genetics, vol. 19, No. 16, Aug. 15, 2010, pp. 3266-3281.
Kearns, N. A. et al., "Cas9 effector-mediated regulation of transcription and differentiation in human pluripotent stem cells," Development, 2014, 141(1): p. 219-23.
Kim, H. et al., "Surrogate reporters for enrichment of cells with nuclease-induced mutations," Nat Methods, 2011, 8:941-943.
Kim, Y. et al., "TALENs and ZFNs are associated with different mutation signatures," Nat Methods, 2013.
Kimura, E. et al., "Cell-lineage regulated myogenesis for dystrophin replacement: a novel therapeutic approach for treatment of muscular dystrophy," Hum Mol Genet 17, 2008, 2507-2517.
Konermann, S. et al., "Optical control of mammalian endogenous transcription and epigenetic states," Nature, 2013, 500(7463): p. 472-6.
Konieczny, P. et al., "Gene and cell-mediated therapies for muscular dystrophy," Muscle Nerve, 2013, 47:649-663.
Kubokawa, I. et al., "Molecular characterization of the 5'-UTR of retinal dystrophin reveals a cryptic intron that regulates translational activity," Molecular Vision, 2010, vol. 16, pp. 2590-2597.
Kyte et al., "A Simple Method for Displaying the Hydropathic Character of a Protein," J. Mol. Biol., 1982, 157:105-132.

Langmead, B. et al., "Ultrafast and memory-efficient alignment of short DNA sequences to the human genome," Genome biology 10, 2009, R25.
Larson, M. H. et al., "CRISPR interference (CRISPRi) for sequence-editing control of gene expression," Nat Protoc, 2013, 8(11): p. 2180-96.
Latta-Mahieu et al. Gene transfer of a chimeric trans-activator is immunogenic and results in short-lived transgene expression. Human Gene Therapy, vol. 13, No. 13, pp. 1611-1620, Sep. 2002.
Lattanzi, L. et al., "High efficiency myogenic conversion of human fibroblasts by adenoviral vector-mediated MyoD gene transfer. An alternative strategy for ex vivo gene therapy of primary myopathies," The Journal of clinical investigation 101, 1998, 2119-2128.
Lee, H. J. et al., "Targeted chromosomal deletions in human cells using zinc finger nucleases," Genome research 20, 2010, 81-89.
Li, D. et al., "Marginal level dystrophin expression improves clinical outcome in a strain of dystrophin/utrophin double knockout mice," PLoS One, 2010, 5:e15286.
Li, H. et al, "In vivo genome editing restores haemostasis in a mouse model of haemophilia," Nature 475, 2011, 217-221.
Li, T. et al., "Modularly assembled designer TAL effector nucleases for targeted gene knockout and gene replacement in eukaryotes," Nucleic Acids Research, 2011, vol. 39, No. 14, pp. 6315-6325.
Li, Y. et al., "Transcription activator-like effector hybrids for conditional control and rewiring of chromosomal transgene expression," Scientific reports 2, 2012, 897.
Liang, J.C. et al., "Engineering biological systems with synthetic RNA molecules," Mol Cell 43, 2011, 915-926.
Lohmueller, J.J. et al., "A tunable zinc finger-based framework for Boolean logic computation in mammalian cells," Nucleic Acids Res 40, 2012, 5180-5187.
Lovric, J. et al., "Terminal Differentiation of Cardiac and Skeletal Myocytes Induces Permissivity to AAV Transduction by Relieving Inhibition Imposed by DNA Damage Response Proteins," Molecular Therapy, 2012, 2087-2097.
Lu, Q. L. et al., "The status of exon skipping as a therapeutic approach to duchenne muscular dystrophy," Molecular Therapy 19, 2011, 9-15.
Lund et al. "Promoter-targeted phage display selections with preassembled synthetic zinc finger libraries for endogenous gene regulation." Journal of Molecular Biology, vol. 340, pp. 599-613, 2004.
Luo et al. Synthetic DNA delivery systems. Nature Biotechnology, vol. 18, pp. 33-37, 2000.
Maeder et al. Robust, synergistic regulation of human gene expression using TALE activators. Nature Methods, vol. 10, No. 3, pp. 243-246, Feb. 10, 2013, including pp. 1/14-14/14 of Supplementary Material.
Maeder, M. L., "Targeted DNA demethylation and activation of endogenous genes using programmable TALE-TET1 fusionproteins," Nat Biotechnol, 2013, 31(12): p. 1137-42.
Maeder, M.L. et al., "Robust, synergistic regulation of human gene expression using TALE activators," Nat Methods 10, 2013, 243-245.
Mali, P. et al., "Cas9 as a versatile tool for engineering biology," Nat Methods, 2013, 10(10): p. 957-63.
Mali, P. et al., "CAS9 transcriptional activators for target specificity screening and paired nickases for cooperative genome engineering," Nat Biotechnol, 2013, 31(9): p. 833-8.
Mali, P. et al., "RNA-Guided Human Genome Engineering via Cas9," Science 339, 2013, 823-826.
Mamchaoui, K. et al., "Immortalized pathological human myoblasts: towards a universal tool for the study of neuromuscular disorders," Skelet Muscle 1, 2011, 1-11.
Mendell, J. R. et al., "Dystrophin immunity in Duchenne's muscular dystrophy," New England Journal of Medicine 363, 2010, 1429-1437.
Mendenhall, E. M. et al., "Locus-specific editing of histone modification at endogenous enhancers," Nat Biotechnol, 2013, 31(12): p. 1133-6.
Mercer, A. C. et al., "Regulation of Endogenous Human Gene Expression by Ligand-Inducible TALE Transcription Factors," ACS Synth Biol, 2013.

(56) References Cited

OTHER PUBLICATIONS

Miller, J.C. et al., "A TALE nuclease architecture for efficient genome editing" Nat Biotechnol 29, 2011, 143-148.
Moscou, M. J. et al., "A simple cipher governs DNA recognition by TAL effectors," Science 326, 2009, 1501.
Murphy et al., "The in vitro transcription of the 7SK RNA gene by RNA polymerase III is dependable only on the presence of an upstream promoter," Cell, 1987, 51:81-87.
Mussolino, C. et al., "A novel TALE nuclease scaffold enables high genome editing activity in combination with low toxicity," Nucleic Acids Res 39, 2011, 9283-9293.
Myslinski et al., "An unusually compact external promoter for RNA polymerase III transcription of the human H1RNA gene," Nucleic Acids Res, 2001, 29:2502-2509.
Negroni, E. et al., "In Vivo Myogenic Potential of Human CD133+ Muscle-derived Stem Cells: A Quantitative Study," Molecular Therapy 17, 2009, 1771-1778.
Nishimasu, H. et al., "Crystal structure of cas9 in complex with guide RNA and target DNA Cell," 2014, 156(5): p. 935-49.
Ohshima et al., "Nucleotide sequence of mouse genomic loci including a gene or pseudogene for U6 (4.85) nuclear RNA," Nucleic Acids Res, 1981, 9:5145-5158.
Ousterout et al., "Reading frame correction by targeted genome editing restores dystrophin expression in cells from Duchenne muscular dystrophy patients," Mol Ther, 2013, 21:1718-1726.
Palu et al. In pursuit of new developments for gene therapy of human diseases. J. Biotechnol. vol. 68, pp. 1-13, 1999.
Papayannakos, C. et al., "Understanding lentiviral vector chromatin targeting: working to reduce insertional mutagenic potential for gene therapy," Gene Ther, 2013, 20(6): p. 581-8.
Park, K.S. et al., "Phenotypic alteration of eukaryotic cells using randomized libraries of artificial transcription factors," Nat Biotechnol 21, 2003, 1208-1214.
Pattanayak, V. et al., "High-throughput profiling of off-target DNA cleavage reveals RNA-programmed Cas9 nuclease specificity," Nat Biotechnol, 2013, 31(9): p. 839-43.
Peault, B. et al., "Stem and progenitor cells in skeletal muscle development, maintenance, and therapy," Molecular Therapy 15, 2007, 867-877.
Perez, E. et al., "Establishment of HIV-1 resistance in CD4+ T cells by genome editing using zinc-finger nucleases," Nature biotechnology 26, 2008, 808-816.
Perez-Pinera et al. Abstract 855. "Synergistic Transcriptional Activation by Combinations of Engineered TALEs" was publicly presented at the American Society of Gene & Cell Therapy's 15th Annual Meeting in Philadelphia, Pennsylvania during the Late Abstracts Poster Session I11: Saturday, May 19, 2012.
Perez-Pinera et al. Synergistic and tunable human gene activation by combinations of synthetic transcription factors. Nature Methods, vol. 10, No. 3, pp. 239-244, Feb. 3, 2013, including pp. 1/12-12-12 of Supplementary Material.
Perez-Pinera et al., "Gene targeting to the ROSA26 locus directed by engineered zinc finger nucleases," Nucleic Acids Research, 2012, 40:3741-3752.
Perez-Pinera et al., "RNA-guided gene activation by CRISPR-Cas9-based transcription factors," Nat Methods, 2013, 10:973-976.
Perez-Pinera, P. et al., "Advances in targeted genome editing," Current Opinion in Chemical Biology 16, 2012, 268-277.
Perez-Pinera, P. et al., "Synergistic and tunable human gene activation by combinations of synthetic transcription factors," Nat Methods 10, 2013, 239-242.
Persons, D. A., "Lentiviral vector gene therapy: effective and safe?" Mol Ther, 2010, 18(5): p. 861-2.
Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23:635-646.
Pichavant, C. et al., "Current status of pharmaceutical and genetic therapeutic approaches to treat DMD," Molecular Therapy 19, 2011, 830-840.
Polstein, L. R. and Gersbach, C. A., "Light-inducible spatiotemporal control of gene activationby customizable zinc finger transcription factors," J Am Chem Soc, 2012, 134(40): p. 16480-3.
Popplewell, L. et al., "Gene correction of a duchenne muscular dystrophy mutation by meganuclease-enhanced exon knock-in," Hum Gene Ther, 2013, 24:692-701.
Qi, L.S. et al., "Repurposing CRISPR as an RNA-guided platform for sequence-specific control of gene expression," Cell 152, 2013, 1173-1183.
Ran, F. A. et al., "Double nicking by RNA-guided CRISPR Cas9 for enhanced genome editing specificity," Cell, 2013, 154(6): p. 1380-9.
Rebar, E.J. et al., "Induction of angiogenesis in a mouse model using engineered transcription factors," Nat Med 8, 2002, 1427-1432.
Reyon, D. et al., "FLASH assembly of TALENs for high-throughput genome editing," Nat Biotechnol 30, 2012, 460-465.
Rousseau, J. et al., "Endonucleases: tools to correct the dystrophin gene" The Journal of Gene Medicine, 2011, vol. 13, pp. 522-537.
Salmon, P. and Trono, D., "Production and titration of lentiviral vectors," Curr Protoc Neurosci, 2006, Chapter 4: Unit 4 21.
Sambrook et al., Molecular Cloning and Laboratory manual, Second Ed., Cold Spring Harbor (1989).
Schmid-Burgk, J. L. et al., "A ligation-independent cloning technique for high-throughput of transcription activator-like effector genes," Nat Biotechnol 31, 2012, 76-81.
Scholze et al. TAL effectors are remote controls for gene activation Current Opinion in Microbiology, vol. 14, pp. 47-53, Jan. 2011.
Schultz, B. R. & Chamberlain, J. S., "Recombinant adeno-associated virus transduction and integration," Molecular Therapy 16, 2008, 1189-1199.
Sebastiano, V. et al., "In Situ Genetic Correction of the Sickle Cell Anemia Mutation in Human Induced Pluripotent Stem Cells Using Engineered Zinc Finger Nucleases," Stem Cells 29, 2011, 1717-1726.
Seto et al., "Gene Replacement Therapies for Duchenne Muscular Dystrophy Using Adeno-Associated Viral Vectors," Current Gene Therapy, 2012, 12:139-151.
Sharma, S. et al., "Efficiency of nonhomologous DNA and joining varies among somatic tissues, despite similarity in mechanism," Cellular and Molecular Life Science 68, 2011, 661-676.
Silva, G. et al., "Meganucleases and other tools for targeted genome engineering: perspective and challenges for gene therapy," Current gene therapy, 2011, 11:11-27.
Şöllü, C. et al., "Autonomous zinc-finger nuclease pairs for targeted chromosomal deletion," Nucleic acids research 38, 2010, 8269-8276.
Song, L. et al., "Dnase-seq: a high-resolution technique for mapping active gene regulatory elements across the genome from mammalian cells," Cold Spring Harbor protocols 2010, pdb prot5384.
Song, L. et al., "Open chromatin defined by DNaseI and FAIRE identifies regulatory elements that shape cell-type identify," Genome Res 21, 2011, 1757-1767.
Sun, N. et al., "Optimized TAL effector nucleases (TALENs) for use in treatment of sickle cell disease," Molecular bioSystems 8, 2012, 1255-1263.
Taniguchi-Ikeda, M. et al., "Pathogenic exon-trapping by SVA retrotransposon and rescue in Fukuyama muscular dystrophy," Nature 478, 2011, 127-131.
Tebas, P. et al., "Gene editing of CCR5 in autologous CD4 T cells of persons infected with HIV," N Engl J Med, 2014, 370:901-910.
Tedesco, F. S. et al., "Repairing skeletal muscle: regenerative potential of skeletal muscle stem cells," J Clin Invest, 2010, 120:11-19.
Tedesco, F. S. et al., "Stem Cell-Mediated Transfer of a Human Artificial Chromosome Ameliorates Musculat Dystrophy," Science Translational Medicine 3, 96ra78-96ra78, 2011.
Tedesco, F. S. et al., "Transplantation of Genetically Corrected Human iPSC-Derived Progenitors in Mice with Limb-Girdle Muscular Dystrophy," Science Translational Medicine 4, 140ra189, 2012.
Urnov, F. et al., "Highly efficient endogenous human gene correction using designed zinc-finger nucleases," Nature 435, 2005, 646-651.

(56) References Cited

OTHER PUBLICATIONS

Van Putten, M. et al., "Low dystrophin levels in heart can delay heart failure in mdx mice," J Mol Cell Cardiol, 2014, 69C:17-23.
Van Putten, M. et al., "Low dystrophin levels increase survival and improve muscle pathology and function in dystrophin/utrophin double-knockout mice," FASEB J, 2013, 27:2484-2495.
Verma and Weitzman. Gene Therapy: Twenty-first century medicine. Annual Review of Biochemistry, vol. 74, pp. 711-738, 2005.
Verma et al. Gene therapy—promises, problems and prospects. Nature, vol. 389, pp. 239-242, 1997.
Vierbuchen, T. et al., "Direct conversion of fibroblasts to functional neurons by defined factors," Nature 463, 2010, 1035-1041.
Wang et al., "Adeno-associated virus vector carrying human minidystrophin genes effectively ameliorates muscular dystrophy in mdx mouse model," Proc Natl Acad Sci US A. (2000) 97(25):13714-13719.
Wang H. et al., "One-Step Generation of Mice Carrying Mutations in Multiple Genes by CRISPR-Cas-Mediated Genome Engineering" Cell, 2013, 153(4): p. 910-8.
Wein, N. et al., "Efficient bypass of mutations in dysferlin deficient patient cells by antisense-induced exon skipping," Hum Mutat 31, 2010, 136-142.
Welch, E. M. et al., "PTC124 targets genetic disorders caused by nonsense mutations," Nature 447, 2007, 87-91.
Yan et al. Biochimica et Biophysica Acta, vol. 1835, No. 1, pp. 76-85, Jan. 2013.
Yang, L., "Optimization of scarless human stem cell genome editing," Nucleic Acids Res, 2013, 41:9049-9061.
Yusa, K. et al., "Targeted gene correction of α1-antitrypsin deficiency in induced pluripotent stem cells," Nature 478, 2011, 391-394.
Zhang, F. et al. "Efficient construction of sequence-specific TAL effectors for modulating mammalian transcription," Nat Biotechnol 29, 2011, 149-153.
Zhu, C. H. et al., "Cellular senescence in human telomerase reverse transcriptase and cyclin—dependent kinase 4: consequences in aging muscle and therapeutic strategies for muscular dystrophies," Aging cell 6, 2007, 515-523.
Zou, J. et al., "Site-specific gene correction of a point mutation in human iPS cells derived from an adult patient with sickle cell disease," Blood 118, 2011, 4599-4608.
International Search Report and Written Opinion for Application No. PCT/US14/41190 dated Dec. 17, 2014 (14 pages).
United States Patent Office Action for U.S. Appl. No. 14/220,116 dated Jul. 22, 2015 (26 pages).
United States Patent Office Final Action for U.S. Appl. No. 14/220,116 dated May 4, 2016 (29 pages).
Extended European Search Report for Application No. 13781472.9 dated Feb. 3, 2016 (11 pages).
United States Patent Office Action for U.S. Appl. No. 14/397,420 dated Jun. 2, 2016 (8 pages).
United States Patent Office Action for U.S. Appl. No. 14/397,420 dated Oct. 5, 2016 (10 pages).
International Search Report and Written Opinion for Application No. PCT/US13/38536 dated Nov. 29, 2013 (27 pages).
United States Patent Office Action for U.S. Appl. No. 14/220,116 dated Dec. 2, 2016 (16 pages).
United States Patent Office Action for U.S. Appl. No. 14/895,316 dated Dec. 15, 2016 (13 pages).
European Examination Report for Application No. 13781472.9 dated Mar. 2, 2017 (5 pages).
United States Patent Office Action for U.S. Appl. No. 14/895,316 dated Apr. 19, 2019 (11 pages).
United States Patent Office Action for U.S. Appl. No. 15/991,333 dated Apr. 19, 2019 (12 pages).
Saito et al., "Specific activation of microRNA-127 with downregulation of the proto-oncogene BCL6 by chromatin-modifying drugs in human cancer cells," Cancer Cell, 2006, vol. 9, pp. 435-443.
Seidel et al., "Chromatin-modifygin agents in anti-cancer therapy," Biochimie, 2012, vol. 94, pp. 2264-2279.
Szyf, M., "Epigenetics, DNA methylation, and chromatin modifying drugs," Annual Review of Pharmacology and Toxicology, 2009, vol. 49, pp. 243-263.
United States Patent Office Action for U.S. Appl. No. 14/220,116 dated Jul. 19, 2017 (15 pages).
United States Patent Office Notice of Allowance for U.S. Appl. No. 14/220,116 dated Sep. 19, 2017 (8 pages).
United States Patent Office Action for U.S. Appl. No. 14/895,316 dated Oct. 22, 2018 (11 pages).
Kwa et al., "Chromatin modifying agents—the cutting edge of anticancer therapy," Drug Discovery Today, 2011, 16 (13/14):543-547.
United States Patent Office Action for U.S. Appl. No. 15/789,348 dated Dec. 10, 2019 (18 pages).
European Patent Office Extended Search Report for Application No. 19179921.2 dated Oct. 17, 2019 (10 pages).
United States Patent Office Notice of Allowance for U.S. Appl. No. 14/895,316 dated Sep. 30, 2019 (9 pages).
United States Patent Office Action for U.S. Appl. No. 15/991,333 dated Oct. 4, 2019 (6 pages).
United States Patent Office Action for U.S. Appl. No. 15/789,348 dated May 22, 2019 (13 pages).
United States Patent Office Notice of Allowance for U.S. Appl. No. 14/895,316 dated Jan. 27, 2020 (7 pages).

\* cited by examiner

TN2 (Fok-ELDS) (SEQ ID NO:1):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNGGGKQALETVQRLLPVLCQDHGLTPDQVVAIAS
NGGGKQALETVQRLLPVLCQDHGLTPDQVVAIASNIGGKQALETVQRLLPVLCQDHGLTPDQVVAIASNGGGKQALETVQRLLPVLCQDHGLTPDQ
VVAIASNGGGKQALETVQRLLPVLCQDHGLTPDQVVAIASHDGGKQALETVQRLLPVLCQDHGLTPDQVVAIASNGGGKQALETVQRLLPVLCQDH
GLTPDQVVAIASHDGGKQALETVQRLLPVLCQDHGLTPDQVVAIASNIGGKQALETVQRLLPVLCQDHGLTPDQVVAIASNNGGKQALETVQRLLPVLC
QDHGLTPDQVVAIASNIGGKQALESIVAQLSRPDPALAALTNDHLVALACLGGRPAMDAVKKGLPHAPELIRRVNRRIGERTSHRVAQLVKSELEEKKS
ELRHKLKYVPHEYIELIEIARNPTQDRILEMKVMEFFMKVYGYRGEHLGGSRKPDGAIYTVGSPIDYGVIVDTKAYSGGYNLPIGQADEMERYVEENQT
RDKHLNPNEWWKVYPSSVTEFKFLFVSGHFKGNYKAQLTRLNHITNCNGAVLSVEELLIGGEMIKAGTLTLEEVRRKFNNGEINF

TN3 (Fok-ELDS) (SEQ ID NO:2):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNGGGKQALETVQRLLPVLCQDHGLTPDQVVAIAS
NNGGKQALETVQRLLPVLCQDHGLTPDQVVAIASHDGGKQALETVQRLLPVLCQDHGLTPDQVVAIASNGGGKQALETVQRLLPVLCQDHGLTPDQVVA
IASHDGGKQALETVQRLLPVLCQDHGLTPDQVVAIASNIGGKQALETVQRLLPVLCQDHGLTPDQVVAIASNGGGKQALETVQRLLPVLCQDHGLT
PDQVVAIASNGGGKQALETVQRLLPVLCQDHGLTPDQVVAIASNIGGKQALETVQRLLPVLCQDHGLTPDQVVAIASNGGGKQALETVQRLLPVLCQDH
GLTPDQVVAIASHDGGKQALETVQRLLPVLCQDHGLTPDQVVAIASNIGGKQALESIVAQLSRPDPALAALTNDHLVALACLGGRPAMDAVKKGLPHAPELIRRVNRRIGERTSHRVAQLVKSELEEKKSELRHKLKYVPHEYIELIEIARNPTQDRILEMKVM
EFFMKVYGYRGEHLGGSRKPDGAIYTVGSPIDYGVIVDTKAYSGGYNLPIGQADEMERYVEENQTRDKHLNPNEWWKVYPSSVTEFKFLFVSGHFKGNY
KAQLTRLNHITNCNGAVLSVEELLIGGEMIKAGTLTLEEVRRKFNNGEINF

TN6 (Fok-KKRS) (SEQ ID NO:3):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNGGGKQALETVQRLLPVLCQDHGLTPDQVVAIAS
NNGGKQALETVQRLLPVLCQDHGLTPDQVVAIASHDGGKQALETVQRLLPVLCQDHGLTPDQVVAIASNGGGKQALETVQRLLPVLCQDHGLTPDQVVA
IASNIGGKQALETVQRLLPVLCQDHGLTPDQVVAIASHDGGKQALETVQRLLPVLCQDHGLTPDQVVAIASNIGGKQALETVQRLLPVLCQDHGLT
PDQVVAIASNNGGKQALETVQRLLPVLCQDHGLTPDQVVAIASNGGGKQALETVQRLLPVLCQDHGLTPDQVVAIASNGGGKQALETVQRLLPVLCQDH
GLTPDQVVAIASHDGGKQALETVQRLLPVLCQDHGLTPDQVVAIASNIGGKQALESIVAQLSRPDPALAALTNDHLVALACLGGRPAMDAVKKGLPHAPELIRRVNRRIGERTSHRVAQLVKSELEEKKSELRHKLKYVPHEYIELIEIARNPTQDRILEMKVM
EFFMKVYGYRGEHLGGSRKPDGAIYTVGSPIDYGVIVDTKAYSGGYNLPIGQADEMQRYVKENQTRNKHINPNEWWKVYPSSVTEFKFLFVSGHFKGNY
KAQLTRLNRKTNCNGAVLSVEELLIGGEMIKAGTLTLEEVRRKFNNGEINF

Figure 2

TN8 (Fok-KKRS)(SEQ ID NO:4):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNGGGKQALETVQRLLPVLCQDHGLTPDQVVAIAS
HDGGKQALETVQRLLPVLCQDHGLTPDQVVAIASNGGGKQALETVQRLLPVLCQDHGLTPDQVVAIASNGGGKQALETVQRLLPVLCQDHGLTPDQVVA
IASNIGGKQALETVQRLLPVLCQDHGLTPDQVVAIASHDGGKQALETVQRLLPVLCQDHGLTPDQVVAIASNGGGKQALETVQRLLPVLCQDHGLT
PDQVVAIASHDGGKQALETVQRLLPVLCQDHGLTPDQVVAIASNIGGKQALETVQRLLPVLCQDHGLTPDQVVAIASNNGGKQALETVQRLLPVLC
QDHGLTPDQVVAIASNGGGKQALESIVAQLSRPDPALAALTNDHLVALACLGGRPAMDAVKKGLPHAPELIRRVNRRIGERTSHRVAQLVKSELEEKKS
ELRHKLKYVPHEYIELIEIARNPTQDRILEMKVMEFFMKVYGYRGEHLGGSPIDYGVIVDTKAYSGGYNLPIGQADEMQRYVKENQT
RNKHINPNEWWKVYPSSVTEFKFLFVSGHFKGNYKAQLTRLNRKTNCNGAVLSVEELLIGGEMIKAGTLTLEEVRRKFNNGEINF

TN9 (Fok-ELDS)(SEQ ID NO:5):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNGGGKQALETVQRLLPVLCQDHGLTPDQVVAIAS
HDGGKQALETVQRLLPVLCQDHGLTPDQVVAIASNIGGKQALETVQRLLPVLCQDHGLTPDQVVAIASNIGGKQALETVQRLLPVLCQDHGLTPDQ
VVAIASHDGGKQALETVQRLLPVLCQDHGLTPDQVVAIASHDGGKQALETVQRLLPVLCQDHGLTPDQVVAIASNIGGKQALETVQRLLPVLCQDH
GLTPDQVVAIASNGGGKQALETVQRLLPVLCQDHGLTPDQVVAIASNIGGKQALETVQRLLPVLCQDHGLTPDQVVAIASNIGGKQALETVQRLLPVLC
QDHGLTPDQVVAIASNGGGKQALESIVAQLSRPDPALAALTNDHLVALACLGGRPAMDAVKKGLPHAPELIRRVNRRIGERTSHRVAQLVKSELEEKKS
ELRHKLKYVPHEYIELIEIARNPTQDRILEMKVMEFFMKVYGYRGEHLGGSPIDYGVIVDTKAYSGGYNLPIGQADEMERYVEENQT
RDKHLNPNEWWKVYPSSVTEFKFLFVSGHFKGNYKAQLTRLNHITNCNGAVLSVEELLIGGEMIKAGTLTLEEVRRKFNNGEINF

TN10 (Fok-ELDS)(SEQ ID NO:6):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASHDGGKQALETVQRLLPVLCQDHGLTPDQVVAIAS
NGGGKQALETVQRLLPVLCQDHGLTPDQVVAIASNIGGKQALETVQRLLPVLCQDHGLTPDQVVAIASNIGGKQALETVQRLLPVLCQDHGLTPDQ
VVAIASHDGGKQALETVQRLLPVLCQDHGLTPDQVVAIASHDGGKQALETVQRLLPVLCQDHGLTPDQVVAIASNIGGKQALETVQRLLPVLCQDH
GLTPDQVVAIASNGGGKQALETVQRLLPVLCQDHGLTPDQVVAIASNIGGKQALETVQRLLPVLCQDHGLTPDQVVAIASNIGGKQALETVQRLLPVLC
QDHGLTPDQVVAIASNGGGKQALESIVAQLSRPDPALAALTNDHLVALACLGGSRKPDGAIYTVGSPIDYGVIVDTKAYSGGYNLPIGQADEMERYVEENQT
ELRHKLKYVPHEYIELIEIARNPTQDRILEMKVMEFFMKVYGYRGEHLGGSPIDYGVIVDTKAYSGGYNLPIGQADEMERYVEENQT
RDKHLNPNEWWKVYPSSVTEFKFLFVSGHFKGNYKAQLTRLNHITNCNGAVLSVEELLIGGEMIKAGTLTLEEVRRKFNNGEINF

Figure 2 (continued)

TN12 (Fok-ELDS)(SEQ ID NO:7):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASHDGGKQALETVQRLLPVLCQDHGLTPDQVVAIAS
HDGGKQALETVQRLLPVLCQDHGLTPDQVVAIASNGGGKQALETVQRLLPVLCQDHGLTPDQVVAIASNGGGKQALETVQRLLPVLCQDHGLTPDQVVA
IASNGGGKQALETVQRLLPVLCQDHGLTPDQVVAIASHDGGKQALETVQRLLPVLCQDHGLTPDQVVAIASNIGGKQALETVQRLLPVLCQDHGLTPDQ
VVAIASNGGGKQALETVQRLLPVLCQDHGLTPDQVVAIASHDGGKQALETVQRLLPVLCQDHGLTPDQVVAIASNIGGKQALETVQRLLPVLCQDH
GLTPDQVVAIASNIGGKQALETVQRLLPVLCQDHGLTPDQVVAIASHDGGKQALETVQRLLPVLCQDHGLTPDQVVAIASHDGGKQALETVQRLLPVLC
QDHGLTPDQVVAIASHDGGKQALESIVAQLSRDPALAALTNDHLVALACLGGRPALELIRRVNRRIGERTSHRVAQLVKSELEEKKS
ELRHKLKYVPHEYIELIEIARNPTQDRILEMKVMEFFMKVYGYRGEHLGGSRKPDGAIYTVGSPIDYGVIVDTKAYSGGYNLPIGQADEMQRYVEENQT
RDKHLNPNEWWKVYPSSVTEFKFLFVSGHFKGNYKAQLTRLNHITNCNGAVLSVEELLIGGEMIKAGTLTLEEVRRKFNNGEINF

TN13 (Fok-KKRS)(SEQ ID NO:8):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASHDGGKQALETVQRLLPVLCQDHGLTPDQVVAIAS
NIGGKQALETVQRLLPVLCQDHGLTPDQVVAIASHDGGKQALETVQRLLPVLCQDHGLTPDQVVAIASNGGGKQALETVQRLLPVLCQDHGLTPDQVVA
IASNIGGKQALETVQRLLPVLCQDHGLTPDQVVAIASNGGGKQALETVQRLLPVLCQDHGLTPDQVVAIASNIGGKQALETVQRLLPVLCQDHGLT
PDQVVAIASNIGGKQALETVQRLLPVLCQDHGLTPDQVVAIASNGGGKQALETVQRLLPVLCQDHGLTPDQVVAIASNIGGKQALETVQRLLPVLCQDH
GLTPDQVVAIASNGGGKQALETVQRLLPVLCQDHGLTPDQVVAIASHDGGKQALETVQRLLPVLCQDHGLTPDQVVAIASHDGGKQALETVQRLLPVLC
QDHGLTPDQVVAIASNGGGKQALESIVAQLSRDPALAALTNDHLVALACLGGSRKPDGAIYTVGSPIDYGVIVDTKAYSGGYNLPIGQADEMQRYVKENQT
ELRHKLKYVPHEYIELIEIARNPTQDRILEMKVMEFFKFLFVSGHFKGNYKAQLTRLNRKTNCNGAVLSVEELLIGGEMIKAGTLTLEEVRRKFNNGEINF
RNKHINPNEWWKVYPSSVTEFKFLFVSGHFKGNYKAQLTRLNRKTNCNGAVLSVEELLIGGEMIKAGTLTLEEVRRKFNNGEINF

TN17 (Fok-KKRS)(SEQ ID NO:9):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASHDGGKQALETVQRLLPVLCQDHGLTPDQVVAIAS
NGGGKQALETVQRLLPVLCQDHGLTPDQVVAIASHDGGKQALETVQRLLPVLCQDHGLTPDQVVAIASNGGGKQALETVQRLLPVLCQDHGLTPDQVVA
IASHDGGKQALETVQRLLPVLCQDHGLTPDQVVAIASNGGGKQALETVQRLLPVLCQDHGLTPDQVVAIASNGGGKQALETVQRLLPVLCQDHGLTPDQ
VVAIASNGGGKQALETVQRLLPVLCQDHGLTPDQVVAIASNGGGKQALETVQRLLPVLCQDHGLTPDQVVAIASNIGGKQALETVQRLLPVLCQDH
GLTPDQVVAIASHDGGKQALETVQRLLPVLCQDHGLTPDQVVAIASHDGGKQALETVQRLLPVLCQDHGLTPDQVVAIASNGGGKQALESIVAQLS
RPDPALAALTNDHLVALACLGGRPAMDAVKKGLPHAPELIRRVNRRIGERTSHRVAQLVKSELEEKKSELRHKLKYVPHEYIELIEIARNPTQDRILEM
KVMEFFMKVYGYRGEHLGGSRKPDGAIYTVGSPIDYGVIVDTKAYSGGYNLPIGQADEMQRYVKENQTRNKHINPNEWWKVYPSSVTEFKFLFVSGHFK
GNYKAQLTRLNRKTNCNGAVLSVEELLIGGEMIKAGTLTLEEVRRKFNNGEINF

Figure 2 (continued)

TN26 (Fok-ELDS)(SEQ ID NO:10):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASHDGGKQALETVQRLLPVLCQDHGLTPDQVVAIAS
NGGGKQALETVQRLLPVLCQDHGLTPDQVVAIASHDGGKQALETVQRLLPVLCQDHGLTPDQVVAIASNGGGKQALETVQRLLPVLCQDHGLTPDQ
IASHDGGKQALETVQRLLPVLCQDHGLTPDQVVAIASNGGGKQALETVQRLLPVLCQDHGLTPDQVVAIASNIGGKQALETVQRLLPVLCQDHGLT
PDQVVAIASNGGGKQALETVQRLLPVLCQDHGLTPDQVVAIASNGGGKQALETVQRLLPVLCQDHGLTPDQVVAIASNIGGKQALETVQRLLPVLC
QDHGLTPDQVVAIASNGGGKQALETVQRLLPVLCQDHGLTPDQVVAIASNGGGKQALESIVAQLS
RPDPALAALTNDHLVALACLGGRPAMDAVKKGLPHAPELIRRVNRRIGERTSHRVAQLVKSELEKKSELRHKLKYVPHEYIELIEIARNPTQDRILEM
KVMEFFMKVYGYRGEHLGGSRKPDGAIYTVGSPIDYGVIVDTKAYSGGYNLPIGQADEMERYVEENQTRDKHLNPNEWWKVYPSSVTEFKFLFVSGHFK
GNYKAQLTRLNHITNCNGAVLSVEELLIGGEMIKAGTLTLEEVRRKFNNGEINF

TN27 (Fok-KKRS)(SEQ ID NO:11):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNIGGKQALETVQRLLPVLCQDHGLTPDQVVAIAS
HDGGKQALETVQRLLPVLCQDHGLTPDQVVAIASHDGGKQALETVQRLLPVLCQDHGLTPDQVVAIASNGGGKQALETVQRLLPVLCQDHGLTPDQ
IASNGGGKQALETVQRLLPVLCQDHGLTPDQVVAIASHDGGKQALETVQRLLPVLCQDHGLTPDQVVAIASNGGGKQALETVQRLLPVLCQDHGLT
PDQVVAIASNGGGKQALETVQRLLPVLCQDHGLTPDQVVAIASNIGGKQALETVQRLLPVLCQDHGLTPDQVVAIASNGGGKQALETVQRLLPVLC
QDHGLTPDQVVAIASNGGGKQALETVQRLLPVLCQDHGLTPDQVVAIASHDGGKQALESIVAQLS
RPDPALAALTNDHLVALACLGGRPAMDAVKKGLPHAPELIRRVNRRIGERTSHRVAQLVKSELEKKSELRHKLKYVPHEYIELIEIARNPTQDRILEM
KVMEFFMKVYGYRGEHLGGSRKPDGAIYTVGSPIDYGVIVDTKAYSGGYNLPIGQADEMQRYVKENQTRNKHINPNEWWKVYPSSVTEFKFLFVSGHFK
GNYKAQLTRLNRKTNCNGAVLSVEELLIGGEMIKAGTLTLEEVRRKFNNGEINF

TN28 (Fok-ELDS)(SEQ ID NO:12):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASHDGGKQALETVQRLLPVLCQDHGLTPDQVVAIAS
NGGGKQALETVQRLLPVLCQDHGLTPDQVVAIASHDGGKQALETVQRLLPVLCQDHGLTPDQVVAIASNGGGKQALETVQRLLPVLCQDHGLTPDQ
IASNGGGKQALETVQRLLPVLCQDHGLTPDQVVAIASNGGGKQALETVQRLLPVLCQDHGLTPDQVVAIASNIGGKQALETVQRLLPVLCQDHGLT
PDQVVAIASNGGGKQALETVQRLLPVLCQDHGLTPDQVVAIASNGGGKQALETVQRLLPVLCQDHGLTPDQVVAIASNIGGKQALETVQRLLPVLC
QDHGLTPDQVVAIASNGGGKQALETVQRLLPVLCQDHGLTPDQVVAIASNGGGKQALESIVAQLSRDPALAALTNDHLVALACLGGRPAMDAVKKGLP
HAPELIRRVNRRIGERTSHRVAQLVKSELEKKSELRHKLKYVPHEYIELIEIARNPTQDRILEMKVMEFFMKVYGYRGEHLGGSRKPDGAIYTVGSPI
DYGVIVDTKAYSGGYNLPIGQADEMERYVEENQTRDKHLNPNEWWKVYPSSVTEFKFLFVSGHFKGNYKAQLTRLNHITNCNGAVLSVEELLGGEMIK
AGTLTLEEVRRKFNNGEINF

Figure 2 (continued)

TN29 (FoK-KKRS) (SEQ ID NO:13):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNIGGKQALETVQRLLPVLCQDHGLTPDQVVAIAS
NNGGKQALETVQRLLPVLCQDHGLTPDQVVAIASHDGGKQALETVQRLLPVLCQDHGLTPDQVVAIASNIGGKQALETVQRLLPVLCQDHGLTPDQVVA
IASNGGKQALETVQRLLPVLCQDHGLTPDQVVAIASNNGGKQALETVQRLLPVLCQDHGLTPDQVVAIASNGGKQALETVQRLLPVLCQDHGLT
PDQVVAIASHDGGKQALETVQRLLPVLCQDHGLTPDQVVAIASHDGGKQALETVQRLLPVLCQDHGLTPDQVVAIASNIGGKQALETVQRLLPVLCQDH
GLTPDQVVAIASNGGGKQALETVQRLLPVLCQDHGLTPDQVVAIASHDGGKQALETVQRLLPVLCQDHGLTPDQVVAIASHDGGKQALETVQRLLPVLC
QDHGLTPDQVVAIASHDGGKQALETVQRLLPVLCQDHGLTPDQVVAIASNGGGKQALESIVAQLSRPDPALAALTNDHLVALACLGGRPAMDAVKKGLP
HAPELIRRVNRRIGERTSHRVAQIVKSELEEKKSELRHKLKYVPHEYIELIEIARNPTQDRILEMKVMEFFMKVYGYRGEHLGGSRKPDGAIYTVGSPI
DYGVIVDTKAYSGGYNLPIGQADEMQRYVKENQTRNKHINPNEWWKVYPSSVTEFKFLFVSGHFKGNYKAQLTRLNRKTNCNGAVLSVEELLIGGEMIK
AGTLTLEEVRRKFNNGEINF

Figure 2 (continued)

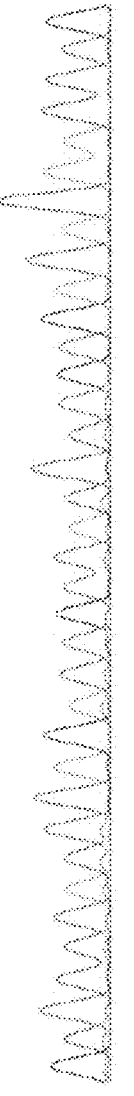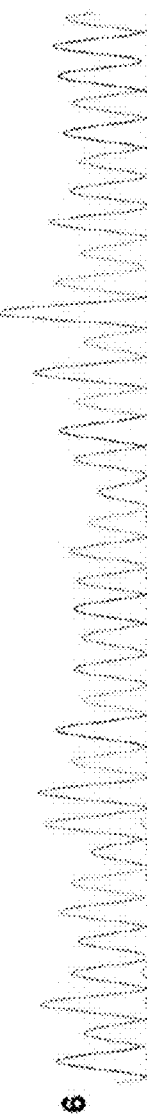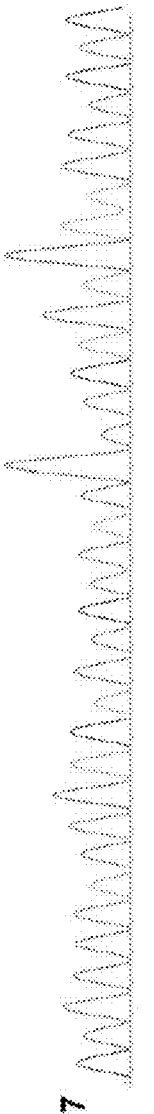
Figure 8

A

| | Target site (5'->3') | | |
|---|---|---|---|
| TN45 (Right TALEN) | tRACTGATGCCAGGATT (- strand) | SEQ ID NO: | 42 |
| TN50 (Left TALEN) | tGGAATTTGAAATATCC | SEQ ID NO: | 43 |
| | | | |
| Full target site | tGGAATTTGAAATATCCNNNNNNNNNNNNNNAATCCTGGCATCAGTTa | SEQ ID NO: | 44 |
| Human target site | tGGAATTTGAAATATCCGGGGCCCTCACAGAATCCTGGCATCAGTTa | SEQ ID NO: | 25 |
| Mouse target site | tGGAATTTGAAATATCCAGAGGGCCTCTACAGAATCCTGGCATCAGTTa | SEQ ID NO: | 45 |

B
RVDs

NI NI HD NG NI NG NN NI NG HD NI NN NN NI NG NG
NN NN NI NI NG NG NG NN NI NI NI NG NI NG HD HD

C

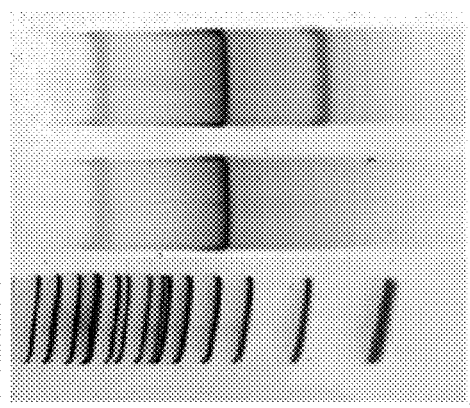

Figure 11

TN45 (Fok-KKRS) (SEQ ID NO:14):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNIGGKQALETVQRLLPVLCQDHGLTPDQVVAIAS
NIGGKQALETVQRLLPVLCQDHGLTPDQVVAIASHDGGKQALETVQRLLPVLCQDHGLTPDQVVAIASNGGKQALETVQRLLPVLCQDHGLTPDQVVA
IASNNGGKQALETVQRLLPVLCQDHGLTPDQVVAIASHDGGKQALETVQRLLPVLCQDHGLTPDQVVAIASNNGGKQALETVQRLLPVLCQDHGLT
PDQVVAIASNIGGKQALETVQRLLPVLCQDHGLTPDQVVAIASNGGKQALETVQRLLPVLCQDHGLTPDQVVAIASNGGKQALESIVAQLSRPD
GLTPDQVVAIASNIGGKQALETVQRLLPVLCQDHGLTPDQVVAIASNGGKQALETVQRLLPVLCQDHGLTPDQVVAIASNGGKQALESIVAQLSRPD
PALAALTNDHLVALACLGGRPAMDAVKKGLPHAPELIRRVNRRIGERTSHRVAQLVKSELEEKKSELRHKLKYVPHEYIELIEIARNPTQDRILEMKVM
EFFMKVYGYRGEHLGGSRKPDGAIYTVGSPIDYGVIVDTKAYSGGYNLPIGQADEMQRYVKENQTRNKHINPNEWWKVYPSSVTEFKFLFVSGHFKGNY
KAQLTRLNRKTNCNGAVLSVEELLIGGEMIKAGTLTLEEVRRKFNNGEINF

TN50 (Fok-ELDS) (SEQ ID NO:15):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNIGGKQALETVQRLLPVLCQDHGLTPDQVVAIAS
NNGGKQALETVQRLLPVLCQDHGLTPDQVVAIASNGGKQALETVQRLLPVLCQDHGLTPDQVVAIASNIGGKQALETVQRLLPVLCQDHGLTPDQ
VVAIASNNGGKQALETVQRLLPVLCQDHGLTPDQVVAIASNIGGKQALETVQRLLPVLCQDHGLTPDQVVAIASHDGGKQALETVQRLLPVLCQDH
PDQVVAIASNGGKQALETVQRLLPVLCQDHGLTPDQVVAIASHDGGKQALETVQRLLPVLCQDHGLTPDQVVAIASIVAQLSRPD
GLTPDQVVAIASHDGGKQALETVQRLLPVLCQDHGLTPDQVVAIASNGGKQALESIVAQLSRPD
PALAALTNDHLVALACLGGRPAMDAVKKGLPHAPELIRRVNRRIGERTSHRVAQLVKSELEEKKSELRHKLKYVPHEYIELIEIARNPTQDRILEMKVM
EFFMKVYGYRGEHLGGSRKPDGAIYTVGSPIDYGVIVDTKAYSGGYNLPIGQADEMERYVEENQTRDKHLNPNEWWKVYPSSVTEFKFLFVSGHFKGNY
KAQLTRLNHITNCNGAVLSVEELLIGGEMIKAGTLTLEEVRRKFNNGEINF

Figure 12

SEQUENCE LISTING

```
<160> NUMBER OF SEQ ID NOS: 93

<210> SEQ ID NO 1
<211> LENGTH: 976
<212> TYPE: PRT
<213> ORGANISM: Artificial Sequence
<220> FEATURE:
<223> OTHER INFORMATION: Synthetic

<400> SEQUENCE: 1

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Arg Gly Ser Val Arg Ser Thr Val Ala Gln His His Glu Ala Leu
            35                  40                  45

Val Gly His Gly Phe Thr His Ala His Ile Val Ala Leu Ser Gln His
        50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
    130                 135                 140
```

```
Asn Ala Leu Thr Gly Ala Pro Leu Asn Leu Thr Pro Asp Gln Val Val
145                 150                 155                 160

Ala Ile Ala Ser Asn Gly Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser Asn Gly Gly Gly Lys Gln Ala Leu Glu Thr
        195                 200                 205

Val Gln Arg Leu Leu Pro Val Leu Cys Gln Asp His Gly Leu Thr Pro
    210                 215                 220

Asp Gln Val Val Ala Ile Ala Ser Asn Gly Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser Asn Ile Gly Gly Lys Gln
            260                 265                 270

Ala Leu Glu Thr Val Gln Arg Leu Leu Pro Val Leu Cys Gln Asp His
        275                 280                 285

Gly Leu Thr Pro Asp Gln Val Val Ala Ile Ala Ser Asn Asn Gly Gly
    290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser His Asp
                325                 330                 335

Gly Gly Lys Gln Ala Leu Glu Thr Val Gln Arg Leu Leu Pro Val Leu
            340                 345                 350

Cys Gln Asp His Gly Leu Thr Pro Asp Gln Val Val Ala Ile Ala Ser
        355                 360                 365

Asn Gly Gly Gly Lys Gln Ala Leu Glu Thr Val Gln Arg Leu Leu Pro
    370                 375                 380

Val Leu Cys Gln Asp His Gly Leu Thr Pro Asp Gln Val Val Ala Ile
385                 390                 395                 400

Ala Ser His Asp Gly Gly Lys Gln Ala Leu Glu Thr Val Gln Arg Leu
                405                 410                 415

Leu Pro Val Leu Cys Gln Asp His Gly Leu Thr Pro Asp Gln Val Val
            420                 425                 430

Ala Ile Ala Ser His Asp Gly Gly Lys Gln Ala Leu Glu Thr Val Gln
        435                 440                 445

Arg Leu Leu Pro Val Leu Cys Gln Asp His Gly Leu Thr Pro Asp Gln
    450                 455                 460

Val Val Ala Ile Ala Ser Asn Gly Gly Gly Lys Gln Ala Leu Glu Thr
465                 470                 475                 480

Val Gln Arg Leu Leu Pro Val Leu Cys Gln Asp His Gly Leu Thr Pro
                485                 490                 495

Asp Gln Val Val Ala Ile Ala Ser Asn Ile Gly Gly Lys Gln Ala Leu
            500                 505                 510

Glu Thr Val Gln Arg Leu Leu Pro Val Leu Cys Gln Asp His Gly Leu
        515                 520                 525

Thr Pro Asp Gln Val Val Ala Ile Ala Ser His Asp Gly Gly Lys Gln
    530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Gly Gly Gly
```

```
                    565                 570                 575
Lys Gln Ala Leu Glu Thr Val Gln Arg Leu Leu Pro Val Leu Cys Gln
                580                 585                 590

Asp His Gly Leu Thr Pro Asp Gln Val Val Ala Ile Ala Ser His Asp
            595                 600                 605

Gly Gly Lys Gln Ala Leu Glu Thr Val Gln Arg Leu Leu Pro Val Leu
        610                 615                 620

Cys Gln Asp His Gly Leu Thr Pro Asp Gln Val Val Ala Ile Ala Ser
625                 630                 635                 640

Asn Ile Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
                660                 665                 670

Ala Ser Asn Asn Gly Gly Lys Gln Ala Leu Glu Thr Val Gln Arg Leu
                675                 680                 685

Leu Pro Val Leu Cys Gln Asp His Gly Leu Thr Pro Asp Gln Val Val
            690                 695                 700

Ala Ile Ala Ser Asn Ile Gly Gly Lys Gln Ala Leu Glu Ser Ile Val
705                 710                 715                 720

Ala Gln Leu Ser Arg Pro Asp Pro Ala Leu Ala Ala Leu Thr Asn Asp
                725                 730                 735

His Leu Val Ala Leu Ala Cys Leu Gly Gly Arg Pro Ala Met Asp Ala
            740                 745                 750

Val Lys Lys Gly Leu Pro His Ala Pro Glu Leu Ile Arg Arg Val Asn
        755                 760                 765

Arg Arg Ile Gly Glu Arg Thr Ser His Arg Val Ala Gln Leu Val Lys
    770                 775                 780

Ser Glu Leu Glu Glu Lys Lys Ser Glu Leu Arg His Lys Leu Lys Tyr
785                 790                 795                 800

Val Pro His Glu Tyr Ile Glu Leu Ile Glu Ile Ala Arg Asn Pro Thr
                805                 810                 815

Gln Asp Arg Ile Leu Glu Met Lys Val Met Glu Phe Phe Met Lys Val
            820                 825                 830

Tyr Gly Tyr Arg Gly Glu His Leu Gly Gly Ser Arg Lys Pro Asp Gly
        835                 840                 845

Ala Ile Tyr Thr Val Gly Ser Pro Ile Asp Tyr Gly Val Ile Val Asp
850                 855                 860

Thr Lys Ala Tyr Ser Gly Gly Tyr Asn Leu Pro Ile Gly Gln Ala Asp
865                 870                 875                 880

Glu Met Glu Arg Tyr Val Glu Asn Gln Thr Arg Asp Lys His Leu
                885                 890                 895

Asn Pro Asn Glu Trp Trp Lys Val Tyr Pro Ser Ser Val Thr Glu Phe
            900                 905                 910

Lys Phe Leu Phe Val Ser Gly His Phe Lys Gly Asn Tyr Lys Ala Gln
        915                 920                 925

Leu Thr Arg Leu Asn His Ile Thr Asn Cys Asn Gly Ala Val Leu Ser
    930                 935                 940

Val Glu Glu Leu Leu Ile Gly Gly Glu Met Ile Lys Ala Gly Thr Leu
945                 950                 955                 960

Thr Leu Glu Glu Val Arg Arg Lys Phe Asn Asn Gly Glu Ile Asn Phe
                965                 970                 975
```

<210> SEQ ID NO 2

<211> LENGTH: 942
<212> TYPE: PRT
<213> ORGANISM: Artificial Sequence
<220> FEATURE:
<223> OTHER INFORMATION: Synthetic

<400> SEQUENCE: 2

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
    130                 135                 140

Asn Ala Leu Thr Gly Ala Pro Leu Asn Leu Thr Pro Asp Gln Val Val
145                 150                 155                 160

Ala Ile Ala Ser Asn Ile Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser Asn Asn Gly Gly Lys Gln Ala Leu Glu Thr
        195                 200                 205

Val Gln Arg Leu Leu Pro Val Leu Cys Gln Asp His Gly Leu Thr Pro
    210                 215                 220

Asp Gln Val Val Ala Ile Ala Ser His Asp Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser Asn Gly Gly Gly Lys Gln
            260                 265                 270

Ala Leu Glu Thr Val Gln Arg Leu Leu Pro Val Leu Cys Gln Asp His
        275                 280                 285

Gly Leu Thr Pro Asp Gln Val Val Ala Ile Ala Ser His Asp Gly Gly
    290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser His Asp
                325                 330                 335

Gly Gly Lys Gln Ala Leu Glu Thr Val Gln Arg Leu Leu Pro Val Leu
            340                 345                 350

Cys Gln Asp His Gly Leu Thr Pro Asp Gln Val Val Ala Ile Ala Ser
        355                 360                 365

Asn Gly Gly Gly Lys Gln Ala Leu Glu Thr Val Gln Arg Leu Leu Pro
    370                 375                 380
```

```
Val Leu Cys Gln Asp His Gly Leu Thr Pro Asp Gln Val Val Ala Ile
385                 390                 395                 400

Ala Ser Asn Ile Gly Gly Lys Gln Ala Leu Glu Thr Val Gln Arg Leu
            405                 410                 415

Leu Pro Val Leu Cys Gln Asp His Gly Leu Thr Pro Asp Gln Val Val
        420                 425                 430

Ala Ile Ala Ser His Asp Gly Gly Lys Gln Ala Leu Glu Thr Val Gln
    435                 440                 445

Arg Leu Leu Pro Val Leu Cys Gln Asp His Gly Leu Thr Pro Asp Gln
450                 455                 460

Val Val Ala Ile Ala Ser Asn Gly Gly Lys Gln Ala Leu Glu Thr
465                 470                 475                 480

Val Gln Arg Leu Leu Pro Val Leu Cys Gln Asp His Gly Leu Thr Pro
            485                 490                 495

Asp Gln Val Val Ala Ile Ala Ser His Asp Gly Gly Lys Gln Ala Leu
        500                 505                 510

Glu Thr Val Gln Arg Leu Leu Pro Val Leu Cys Gln Asp His Gly Leu
    515                 520                 525

Thr Pro Asp Gln Val Val Ala Ile Ala Ser Asn Ile Gly Gly Lys Gln
530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Asn Gly Gly
            565                 570                 575

Lys Gln Ala Leu Glu Thr Val Gln Arg Leu Leu Pro Val Leu Cys Gln
        580                 585                 590

Asp His Gly Leu Thr Pro Asp Gln Val Val Ala Ile Ala Ser Asn Ile
    595                 600                 605

Gly Gly Lys Gln Ala Leu Glu Thr Val Gln Arg Leu Leu Pro Val Leu
610                 615                 620

Cys Gln Asp His Gly Leu Thr Pro Asp Gln Val Val Ala Ile Ala Ser
625                 630                 635                 640

His Asp Gly Gly Lys Gln Ala Leu Glu Thr Val Gln Arg Leu Leu Pro
            645                 650                 655

Val Leu Cys Gln Asp His Gly Leu Thr Pro Asp Gln Val Val Ala Ile
        660                 665                 670

Ala Ser Asn Gly Gly Gly Lys Gln Ala Leu Glu Ser Ile Val Ala Gln
    675                 680                 685

Leu Ser Arg Pro Asp Pro Ala Leu Ala Ala Leu Thr Asn Asp His Leu
690                 695                 700

Val Ala Leu Ala Cys Leu Gly Gly Arg Pro Ala Met Asp Ala Val Lys
705                 710                 715                 720

Lys Gly Leu Pro His Ala Pro Glu Leu Ile Arg Arg Val Asn Arg Arg
            725                 730                 735

Ile Gly Glu Arg Thr Ser His Arg Val Ala Gln Leu Val Lys Ser Glu
        740                 745                 750

Leu Glu Glu Lys Lys Ser Glu Leu Arg His Lys Leu Lys Tyr Val Pro
    755                 760                 765

His Glu Tyr Ile Glu Leu Ile Glu Ile Ala Arg Asn Pro Thr Gln Asp
770                 775                 780

Arg Ile Leu Glu Met Lys Val Met Glu Phe Phe Met Lys Val Tyr Gly
785                 790                 795                 800
```

```
Tyr Arg Gly Glu His Leu Gly Gly Ser Arg Lys Pro Asp Gly Ala Ile
                805                 810                 815

Tyr Thr Val Gly Ser Pro Ile Asp Tyr Gly Val Ile Val Asp Thr Lys
            820                 825                 830

Ala Tyr Ser Gly Gly Tyr Asn Leu Pro Ile Gly Gln Ala Asp Glu Met
            835                 840                 845

Glu Arg Tyr Val Glu Glu Asn Gln Thr Arg Asp Lys His Leu Asn Pro
850                 855                 860

Asn Glu Trp Trp Lys Val Tyr Pro Ser Ser Val Thr Glu Phe Lys Phe
865                 870                 875                 880

Leu Phe Val Ser Gly His Phe Lys Gly Asn Tyr Lys Ala Gln Leu Thr
                885                 890                 895

Arg Leu Asn His Ile Thr Asn Cys Asn Gly Ala Val Leu Ser Val Glu
                900                 905                 910

Glu Leu Leu Ile Gly Gly Glu Met Ile Lys Ala Gly Thr Leu Thr Leu
            915                 920                 925

Glu Glu Val Arg Arg Lys Phe Asn Asn Gly Glu Ile Asn Phe
            930                 935                 940

<210> SEQ ID NO 3
<211> LENGTH: 942
<212> TYPE: PRT
<213> ORGANISM: Artificial Sequence
<220> FEATURE:
<223> OTHER INFORMATION: Synthetic

<400> SEQUENCE: 3

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
130                 135                 140

Asn Ala Leu Thr Gly Ala Pro Leu Asn Leu Thr Pro Asp Gln Val Val
145                 150                 155                 160

Ala Ile Ala Ser Asn Ile Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser Asn Asn Gly Gly Lys Gln Ala Leu Glu Thr
        195                 200                 205

Val Gln Arg Leu Leu Pro Val Leu Cys Gln Asp His Gly Leu Thr Pro
    210                 215                 220
```

-continued

```
Asp Gln Val Val Ala Ile Ala Ser Asn Gly Gly Lys Gln Ala Leu
225                 230                 235                 240

Glu Thr Val Gln Arg Leu Leu Pro Val Leu Cys Gln Asp His Gly Leu
            245                 250                 255

Thr Pro Asp Gln Val Val Ala Ile Ala Ser Asn Ile Gly Gly Lys Gln
        260                 265                 270

Ala Leu Glu Thr Val Gln Arg Leu Leu Pro Val Leu Cys Gln Asp His
    275                 280                 285

Gly Leu Thr Pro Asp Gln Val Val Ala Ile Ala Ser Asn Ile Gly Gly
290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser His Asp
                325                 330                 335

Gly Gly Lys Gln Ala Leu Glu Thr Val Gln Arg Leu Leu Pro Val Leu
            340                 345                 350

Cys Gln Asp His Gly Leu Thr Pro Asp Gln Val Val Ala Ile Ala Ser
        355                 360                 365

His Asp Gly Gly Lys Gln Ala Leu Glu Thr Val Gln Arg Leu Leu Pro
    370                 375                 380

Val Leu Cys Gln Asp His Gly Leu Thr Pro Asp Gln Val Val Ala Ile
385                 390                 395                 400

Ala Ser Asn Ile Gly Gly Lys Gln Ala Leu Glu Thr Val Gln Arg Leu
                405                 410                 415

Leu Pro Val Leu Cys Gln Asp His Gly Leu Thr Pro Asp Gln Val Val
            420                 425                 430

Ala Ile Ala Ser His Asp Gly Gly Lys Gln Ala Leu Glu Thr Val Gln
        435                 440                 445

Arg Leu Leu Pro Val Leu Cys Gln Asp His Gly Leu Thr Pro Asp Gln
    450                 455                 460

Val Val Ala Ile Ala Ser Asn Ile Gly Gly Lys Gln Ala Leu Glu Thr
465                 470                 475                 480

Val Gln Arg Leu Leu Pro Val Leu Cys Gln Asp His Gly Leu Thr Pro
                485                 490                 495

Asp Gln Val Val Ala Ile Ala Ser Asn Asn Gly Gly Lys Gln Ala Leu
            500                 505                 510

Glu Thr Val Gln Arg Leu Leu Pro Val Leu Cys Gln Asp His Gly Leu
        515                 520                 525

Thr Pro Asp Gln Val Val Ala Ile Ala Ser Asn Asn Gly Gly Lys Gln
    530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Gly Gly
                565                 570                 575

Lys Gln Ala Leu Glu Thr Val Gln Arg Leu Leu Pro Val Leu Cys Gln
            580                 585                 590

Asp His Gly Leu Thr Pro Asp Gln Val Val Ala Ile Ala Ser Asn Gly
        595                 600                 605

Gly Gly Lys Gln Ala Leu Glu Thr Val Gln Arg Leu Leu Pro Val Leu
    610                 615                 620

Cys Gln Asp His Gly Leu Thr Pro Asp Gln Val Val Ala Ile Ala Ser
625                 630                 635                 640

Asn Asn Gly Gly Lys Gln Ala Leu Glu Thr Val Gln Arg Leu Leu Pro
```

```
                    645                 650                 655
Val Leu Cys Gln Asp His Gly Leu Thr Pro Asp Gln Val Val Ala Ile
                660                 665                 670

Ala Ser Asn Gly Gly Lys Gln Ala Leu Glu Ser Ile Val Ala Gln
            675                 680                 685

Leu Ser Arg Pro Asp Pro Ala Leu Ala Ala Leu Thr Asn Asp His Leu
        690                 695                 700

Val Ala Leu Ala Cys Leu Gly Gly Arg Pro Ala Met Asp Ala Val Lys
705                 710                 715                 720

Lys Gly Leu Pro His Ala Pro Glu Leu Ile Arg Arg Val Asn Arg Arg
                725                 730                 735

Ile Gly Glu Arg Thr Ser His Arg Val Ala Gln Leu Val Lys Ser Glu
            740                 745                 750

Leu Glu Glu Lys Lys Ser Glu Leu Arg His Lys Leu Lys Tyr Val Pro
        755                 760                 765

His Glu Tyr Ile Glu Leu Ile Glu Ile Ala Arg Asn Pro Thr Gln Asp
    770                 775                 780

Arg Ile Leu Glu Met Lys Val Met Glu Phe Phe Met Lys Val Tyr Gly
785                 790                 795                 800

Tyr Arg Gly Glu His Leu Gly Gly Ser Arg Lys Pro Asp Gly Ala Ile
                805                 810                 815

Tyr Thr Val Gly Ser Pro Ile Asp Tyr Gly Val Ile Val Asp Thr Lys
            820                 825                 830

Ala Tyr Ser Gly Gly Tyr Asn Leu Pro Ile Gly Gln Ala Asp Glu Met
        835                 840                 845

Gln Arg Tyr Val Lys Glu Asn Gln Thr Arg Asn Lys His Ile Asn Pro
    850                 855                 860

Asn Glu Trp Trp Lys Val Tyr Pro Ser Ser Val Thr Glu Phe Lys Phe
865                 870                 875                 880

Leu Phe Val Ser Gly His Phe Lys Gly Asn Tyr Lys Ala Gln Leu Thr
                885                 890                 895

Arg Leu Asn Arg Lys Thr Asn Cys Asn Gly Ala Val Leu Ser Val Glu
            900                 905                 910

Glu Leu Leu Ile Gly Gly Glu Met Ile Lys Ala Gly Thr Leu Thr Leu
        915                 920                 925

Glu Glu Val Arg Arg Lys Phe Asn Asn Gly Glu Ile Asn Phe
    930                 935                 940

<210> SEQ ID NO 4
<211> LENGTH: 976
<212> TYPE: PRT
<213> ORGANISM: Artificial Sequence
<220> FEATURE:
<223> OTHER INFORMATION: Synthetic

<400> SEQUENCE: 4

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Arg Gly Ser Val Arg Ser Thr Val Ala Gln His His Glu Ala Leu
            35                  40                  45

Val Gly His Gly Phe Thr His Ala His Ile Val Ala Leu Ser Gln His
        50                  55                  60

Pro Ala Ala Leu Gly Thr Val Ala Val Thr Tyr Gln His Ile Ile Thr
```

```
            65                  70                  75                  80
Ala Leu Pro Glu Ala Thr His Glu Asp Ile Val Gly Val Gly Lys Gln
                    85                  90                  95

Trp Ser Gly Ala Arg Ala Leu Glu Ala Leu Leu Thr Asp Ala Gly Glu
                100                 105                 110

Leu Arg Gly Pro Pro Leu Gln Leu Asp Thr Gly Gln Leu Val Lys Ile
                115                 120                 125

Ala Lys Arg Gly Gly Val Thr Ala Met Glu Ala Val His Ala Ser Arg
130                 135                 140

Asn Ala Leu Thr Gly Ala Pro Leu Asn Leu Thr Pro Asp Gln Val Val
145                 150                 155                 160

Ala Ile Ala Ser His Asp Gly Gly Lys Gln Ala Leu Glu Thr Val Gln
                165                 170                 175

Arg Leu Leu Pro Val Leu Cys Gln Asp His Gly Leu Thr Pro Asp Gln
                180                 185                 190

Val Val Ala Ile Ala Ser His Asp Gly Gly Lys Gln Ala Leu Glu Thr
                195                 200                 205

Val Gln Arg Leu Leu Pro Val Leu Cys Gln Asp His Gly Leu Thr Pro
210                 215                 220

Asp Gln Val Val Ala Ile Ala Ser Asn Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser Asn Gly Gly Lys Gln
                260                 265                 270

Ala Leu Glu Thr Val Gln Arg Leu Leu Pro Val Leu Cys Gln Asp His
            275                 280                 285

Gly Leu Thr Pro Asp Gln Val Val Ala Ile Ala Ser Asn Ile Gly Gly
            290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser Asn Asn
                325                 330                 335

Gly Gly Lys Gln Ala Leu Glu Thr Val Gln Arg Leu Leu Pro Val Leu
                340                 345                 350

Cys Gln Asp His Gly Leu Thr Pro Asp Gln Val Val Ala Ile Ala Ser
                355                 360                 365

Asn Gly Gly Lys Gln Ala Leu Glu Thr Val Gln Arg Leu Leu Pro
370                 375                 380

Val Leu Cys Gln Asp His Gly Leu Thr Pro Asp Gln Val Val Ala Ile
385                 390                 395                 400

Ala Ser Asn Ile Gly Gly Lys Gln Ala Leu Glu Thr Val Gln Arg Leu
                405                 410                 415

Leu Pro Val Leu Cys Gln Asp His Gly Leu Thr Pro Asp Gln Val Val
                420                 425                 430

Ala Ile Ala Ser Asn Ile Gly Gly Lys Gln Ala Leu Glu Thr Val Gln
            435                 440                 445

Arg Leu Leu Pro Val Leu Cys Gln Asp His Gly Leu Thr Pro Asp Gln
            450                 455                 460

Val Val Ala Ile Ala Ser His Asp Gly Gly Lys Gln Ala Leu Glu Thr
465                 470                 475                 480

Val Gln Arg Leu Leu Pro Val Leu Cys Gln Asp His Gly Leu Thr Pro
                485                 490                 495
```

```
Asp Gln Val Val Ala Ile Ala Ser His Asp Gly Gly Lys Gln Ala Leu
                500                 505                 510

Glu Thr Val Gln Arg Leu Leu Pro Val Leu Cys Gln Asp His Gly Leu
        515                 520                 525

Thr Pro Asp Gln Val Val Ala Ile Ala Ser Asn Ile Gly Gly Lys Gln
530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser His Asp Gly Gly
                565                 570                 575

Lys Gln Ala Leu Glu Thr Val Gln Arg Leu Leu Pro Val Leu Cys Gln
        580                 585                 590

Asp His Gly Leu Thr Pro Asp Gln Val Val Ala Ile Ala Ser Asn Ile
            595                 600                 605

Gly Gly Lys Gln Ala Leu Glu Thr Val Gln Arg Leu Leu Pro Val Leu
        610                 615                 620

Cys Gln Asp His Gly Leu Thr Pro Asp Gln Val Val Ala Ile Ala Ser
625                 630                 635                 640

Asn Asn Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
        660                 665                 670

Ala Ser Asn Asn Gly Gly Lys Gln Ala Leu Glu Thr Val Gln Arg Leu
            675                 680                 685

Leu Pro Val Leu Cys Gln Asp His Gly Leu Thr Pro Asp Gln Val Val
        690                 695                 700

Ala Ile Ala Ser Asn Gly Gly Gly Lys Gln Ala Leu Glu Ser Ile Val
705                 710                 715                 720

Ala Gln Leu Ser Arg Pro Asp Pro Ala Leu Ala Ala Leu Thr Asn Asp
                725                 730                 735

His Leu Val Ala Leu Ala Cys Leu Gly Gly Arg Pro Ala Met Asp Ala
        740                 745                 750

Val Lys Lys Gly Leu Pro His Ala Pro Glu Leu Ile Arg Arg Val Asn
            755                 760                 765

Arg Arg Ile Gly Glu Arg Thr Ser His Arg Val Ala Gln Leu Val Lys
        770                 775                 780

Ser Glu Leu Glu Glu Lys Lys Ser Glu Leu Arg His Lys Leu Lys Tyr
785                 790                 795                 800

Val Pro His Glu Tyr Ile Glu Leu Ile Glu Ile Ala Arg Asn Pro Thr
                805                 810                 815

Gln Asp Arg Ile Leu Glu Met Lys Val Met Glu Phe Phe Met Lys Val
        820                 825                 830

Tyr Gly Tyr Arg Gly Glu His Leu Gly Gly Ser Arg Lys Pro Asp Gly
            835                 840                 845

Ala Ile Tyr Thr Val Gly Ser Pro Ile Asp Tyr Gly Val Ile Val Asp
850                 855                 860

Thr Lys Ala Tyr Ser Gly Gly Tyr Asn Leu Pro Ile Gly Gln Ala Asp
865                 870                 875                 880

Glu Met Gln Arg Tyr Val Lys Glu Asn Gln Thr Arg Asn Lys His Ile
                885                 890                 895

Asn Pro Asn Glu Trp Trp Lys Val Tyr Pro Ser Ser Val Thr Glu Phe
        900                 905                 910
```

```
Lys Phe Leu Phe Val Ser Gly His Phe Lys Gly Asn Tyr Lys Ala Gln
            915                 920                 925

Leu Thr Arg Leu Asn Arg Lys Thr Asn Cys Asn Gly Ala Val Leu Ser
        930                 935                 940

Val Glu Glu Leu Leu Ile Gly Gly Glu Met Ile Lys Ala Gly Thr Leu
945                 950                 955                 960

Thr Leu Glu Glu Val Arg Arg Lys Phe Asn Asn Gly Glu Ile Asn Phe
                965                 970                 975

<210> SEQ ID NO 5
<211> LENGTH: 976
<212> TYPE: PRT
<213> ORGANISM: Artificial Sequence
<220> FEATURE:
<223> OTHER INFORMATION: Synthetic

<400> SEQUENCE: 5

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
                20                  25                  30

Gly Arg Gly Ser Val Arg Ser Thr Val Ala Gln His His Glu Ala Leu
            35                  40                  45

Val Gly His Gly Phe Thr His Ala His Ile Val Ala Leu Ser Gln His
        50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
130                 135                 140

Asn Ala Leu Thr Gly Ala Pro Leu Asn Leu Thr Pro Asp Gln Val Val
145                 150                 155                 160

Ala Ile Ala Ser Asn Asn Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser His Asp Gly Gly Lys Gln Ala Leu Glu Thr
        195                 200                 205

Val Gln Arg Leu Leu Pro Val Leu Cys Gln Asp His Gly Leu Thr Pro
    210                 215                 220

Asp Gln Val Val Ala Ile Ala Ser Asn Ile Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser Asn Ile Gly Gly Lys Gln
            260                 265                 270

Ala Leu Glu Thr Val Gln Arg Leu Leu Pro Val Leu Cys Gln Asp His
        275                 280                 285

Gly Leu Thr Pro Asp Gln Val Val Ala Ile Ala Ser Asn Ile Gly Gly
    290                 295                 300
```

```
Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser Asn Ile
                325                 330                 335

Gly Gly Lys Gln Ala Leu Glu Thr Val Gln Arg Leu Leu Pro Val Leu
            340                 345                 350

Cys Gln Asp His Gly Leu Thr Pro Asp Gln Val Val Ala Ile Ala Ser
        355                 360                 365

Asn Ile Gly Gly Lys Gln Ala Leu Glu Thr Val Gln Arg Leu Leu Pro
370                 375                 380

Val Leu Cys Gln Asp His Gly Leu Thr Pro Asp Gln Val Val Ala Ile
385                 390                 395                 400

Ala Ser His Asp Gly Gly Lys Gln Ala Leu Glu Thr Val Gln Arg Leu
                405                 410                 415

Leu Pro Val Leu Cys Gln Asp His Gly Leu Thr Pro Asp Gln Val Val
                420                 425                 430

Ala Ile Ala Ser His Asp Gly Gly Lys Gln Ala Leu Glu Thr Val Gln
            435                 440                 445

Arg Leu Leu Pro Val Leu Cys Gln Asp His Gly Leu Thr Pro Asp Gln
450                 455                 460

Val Val Ala Ile Ala Ser His Asp Gly Gly Lys Gln Ala Leu Glu Thr
465                 470                 475                 480

Val Gln Arg Leu Leu Pro Val Leu Cys Gln Asp His Gly Leu Thr Pro
                485                 490                 495

Asp Gln Val Val Ala Ile Ala Ser Asn Ile Gly Gly Lys Gln Ala Leu
            500                 505                 510

Glu Thr Val Gln Arg Leu Leu Pro Val Leu Cys Gln Asp His Gly Leu
        515                 520                 525

Thr Pro Asp Gln Val Val Ala Ile Ala Ser Asn Ile Gly Gly Lys Gln
530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Ile Gly Gly
                565                 570                 575

Lys Gln Ala Leu Glu Thr Val Gln Arg Leu Leu Pro Val Leu Cys Gln
                580                 585                 590

Asp His Gly Leu Thr Pro Asp Gln Val Val Ala Ile Ala Ser Asn Ile
            595                 600                 605

Gly Gly Lys Gln Ala Leu Glu Thr Val Gln Arg Leu Leu Pro Val Leu
        610                 615                 620

Cys Gln Asp His Gly Leu Thr Pro Asp Gln Val Val Ala Ile Ala Ser
625                 630                 635                 640

Asn Gly Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
                660                 665                 670

Ala Ser Asn Ile Gly Gly Lys Gln Ala Leu Glu Thr Val Gln Arg Leu
            675                 680                 685

Leu Pro Val Leu Cys Gln Asp His Gly Leu Thr Pro Asp Gln Val Val
        690                 695                 700

Ala Ile Ala Ser Asn Gly Gly Gly Lys Gln Ala Leu Glu Ser Ile Val
705                 710                 715                 720

Ala Gln Leu Ser Arg Pro Asp Pro Ala Leu Ala Ala Leu Thr Asn Asp
```

```
                725                 730                 735
His Leu Val Ala Leu Ala Cys Leu Gly Gly Arg Pro Ala Met Asp Ala
            740                 745                 750

Val Lys Lys Gly Leu Pro His Ala Pro Glu Leu Ile Arg Arg Val Asn
        755                 760                 765

Arg Arg Ile Gly Glu Arg Thr Ser His Arg Val Ala Gln Leu Val Lys
    770                 775                 780

Ser Glu Leu Glu Lys Lys Ser Glu Leu Arg His Lys Leu Lys Tyr
785                 790                 795                 800

Val Pro His Glu Tyr Ile Glu Leu Ile Glu Ile Ala Arg Asn Pro Thr
                805                 810                 815

Gln Asp Arg Ile Leu Glu Met Lys Val Met Glu Phe Phe Met Lys Val
            820                 825                 830

Tyr Gly Tyr Arg Gly Glu His Leu Gly Gly Ser Arg Lys Pro Asp Gly
        835                 840                 845

Ala Ile Tyr Thr Val Gly Ser Pro Ile Asp Tyr Gly Val Ile Val Asp
    850                 855                 860

Thr Lys Ala Tyr Ser Gly Gly Tyr Asn Leu Pro Ile Gly Gln Ala Asp
865                 870                 875                 880

Glu Met Glu Arg Tyr Val Glu Asn Gln Thr Arg Asp Lys His Leu
                885                 890                 895

Asn Pro Asn Glu Trp Trp Lys Val Tyr Pro Ser Ser Val Thr Glu Phe
            900                 905                 910

Lys Phe Leu Phe Val Ser Gly His Phe Lys Gly Asn Tyr Lys Ala Gln
        915                 920                 925

Leu Thr Arg Leu Asn His Ile Thr Asn Cys Asn Gly Ala Val Leu Ser
    930                 935                 940

Val Glu Glu Leu Leu Ile Gly Gly Glu Met Ile Lys Ala Gly Thr Leu
945                 950                 955                 960

Thr Leu Glu Glu Val Arg Arg Lys Phe Asn Asn Gly Glu Ile Asn Phe
                965                 970                 975

<210> SEQ ID NO 6
<211> LENGTH: 976
<212> TYPE: PRT
<213> ORGANISM: Artificial Sequence
<220> FEATURE:
<223> OTHER INFORMATION: Synthetic

<400> SEQUENCE: 6

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
```

```
                115                 120                 125
Ala Lys Arg Gly Gly Val Thr Ala Met Glu Ala Val His Ala Ser Arg
            130                 135                 140
Asn Ala Leu Thr Gly Ala Pro Leu Asn Leu Thr Pro Asp Gln Val Val
145                 150                 155                 160
Ala Ile Ala Ser Asn Gly Gly Gly Lys Gln Ala Leu Glu Thr Val Gln
                165                 170                 175
Arg Leu Leu Pro Val Leu Cys Gln Asp His Gly Leu Thr Pro Asp Gln
            180                 185                 190
Val Val Ala Ile Ala Ser Asn Gly Gly Gly Lys Gln Ala Leu Glu Thr
        195                 200                 205
Val Gln Arg Leu Leu Pro Val Leu Cys Gln Asp His Gly Leu Thr Pro
    210                 215                 220
Asp Gln Val Val Ala Ile Ala Ser Asn Asn Gly Gly Lys Gln Ala Leu
225                 230                 235                 240
Glu Thr Val Gln Arg Leu Leu Pro Val Leu Cys Gln Asp His Gly Leu
                245                 250                 255
Thr Pro Asp Gln Val Val Ala Ile Ala Ser His Asp Gly Gly Lys Gln
            260                 265                 270
Ala Leu Glu Thr Val Gln Arg Leu Leu Pro Val Leu Cys Gln Asp His
        275                 280                 285
Gly Leu Thr Pro Asp Gln Val Val Ala Ile Ala Ser Asn Ile Gly Gly
    290                 295                 300
Lys Gln Ala Leu Glu Thr Val Gln Arg Leu Leu Pro Val Leu Cys Gln
305                 310                 315                 320
Asp His Gly Leu Thr Pro Asp Gln Val Val Ala Ile Ala Ser Asn Ile
                325                 330                 335
Gly Gly Lys Gln Ala Leu Glu Thr Val Gln Arg Leu Leu Pro Val Leu
            340                 345                 350
Cys Gln Asp His Gly Leu Thr Pro Asp Gln Val Val Ala Ile Ala Ser
        355                 360                 365
Asn Ile Gly Gly Lys Gln Ala Leu Glu Thr Val Gln Arg Leu Leu Pro
    370                 375                 380
Val Leu Cys Gln Asp His Gly Leu Thr Pro Asp Gln Val Val Ala Ile
385                 390                 395                 400
Ala Ser Asn Ile Gly Gly Lys Gln Ala Leu Glu Thr Val Gln Arg Leu
                405                 410                 415
Leu Pro Val Leu Cys Gln Asp His Gly Leu Thr Pro Asp Gln Val Val
            420                 425                 430
Ala Ile Ala Ser Asn Ile Gly Gly Lys Gln Ala Leu Glu Thr Val Gln
        435                 440                 445
Arg Leu Leu Pro Val Leu Cys Gln Asp His Gly Leu Thr Pro Asp Gln
    450                 455                 460
Val Val Ala Ile Ala Ser His Asp Gly Gly Lys Gln Ala Leu Glu Thr
465                 470                 475                 480
Val Gln Arg Leu Leu Pro Val Leu Cys Gln Asp His Gly Leu Thr Pro
                485                 490                 495
Asp Gln Val Val Ala Ile Ala Ser His Asp Gly Gly Lys Gln Ala Leu
            500                 505                 510
Glu Thr Val Gln Arg Leu Leu Pro Val Leu Cys Gln Asp His Gly Leu
        515                 520                 525
Thr Pro Asp Gln Val Val Ala Ile Ala Ser His Asp Gly Gly Lys Gln
    530                 535                 540
```

```
Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Ile Gly Gly
                565                 570                 575

Lys Gln Ala Leu Glu Thr Val Gln Arg Leu Leu Pro Val Leu Cys Gln
            580                 585                 590

Asp His Gly Leu Thr Pro Asp Gln Val Val Ala Ile Ala Ser Asn Ile
        595                 600                 605

Gly Gly Lys Gln Ala Leu Glu Thr Val Gln Arg Leu Leu Pro Val Leu
    610                 615                 620

Cys Gln Asp His Gly Leu Thr Pro Asp Gln Val Val Ala Ile Ala Ser
625                 630                 635                 640

Asn Ile Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
            660                 665                 670

Ala Ser Asn Ile Gly Gly Lys Gln Ala Leu Glu Thr Val Gln Arg Leu
        675                 680                 685

Leu Pro Val Leu Cys Gln Asp His Gly Leu Thr Pro Asp Gln Val Val
    690                 695                 700

Ala Ile Ala Ser Asn Gly Gly Lys Gln Ala Leu Glu Ser Ile Val
705                 710                 715                 720

Ala Gln Leu Ser Arg Pro Asp Pro Ala Leu Ala Ala Leu Thr Asn Asp
                725                 730                 735

His Leu Val Ala Leu Ala Cys Leu Gly Gly Arg Pro Ala Met Asp Ala
            740                 745                 750

Val Lys Lys Gly Leu Pro His Ala Pro Glu Leu Ile Arg Arg Val Asn
        755                 760                 765

Arg Arg Ile Gly Glu Arg Thr Ser His Arg Val Ala Gln Leu Val Lys
    770                 775                 780

Ser Glu Leu Glu Glu Lys Lys Ser Glu Leu Arg His Lys Leu Lys Tyr
785                 790                 795                 800

Val Pro His Glu Tyr Ile Glu Leu Ile Glu Ile Ala Arg Asn Pro Thr
                805                 810                 815

Gln Asp Arg Ile Leu Glu Met Lys Val Met Glu Phe Phe Met Lys Val
            820                 825                 830

Tyr Gly Tyr Arg Gly Glu His Leu Gly Gly Ser Arg Lys Pro Asp Gly
        835                 840                 845

Ala Ile Tyr Thr Val Gly Ser Pro Ile Asp Tyr Gly Val Ile Val Asp
    850                 855                 860

Thr Lys Ala Tyr Ser Gly Gly Tyr Asn Leu Pro Ile Gly Gln Ala Asp
865                 870                 875                 880

Glu Met Glu Arg Tyr Val Glu Glu Asn Gln Thr Arg Asp Lys His Leu
                885                 890                 895

Asn Pro Asn Glu Trp Trp Lys Val Tyr Pro Ser Ser Val Thr Glu Phe
            900                 905                 910

Lys Phe Leu Phe Val Ser Gly His Phe Lys Gly Asn Tyr Lys Ala Gln
        915                 920                 925

Leu Thr Arg Leu Asn His Ile Thr Asn Cys Asn Gly Ala Val Leu Ser
    930                 935                 940

Val Glu Glu Leu Leu Ile Gly Gly Glu Met Ile Lys Ala Gly Thr Leu
945                 950                 955                 960
```

Thr Leu Glu Glu Val Arg Arg Lys Phe Asn Asn Gly Glu Ile Asn Phe
                965                 970                 975

<210> SEQ ID NO 7
<211> LENGTH: 976
<212> TYPE: PRT
<213> ORGANISM: Artificial Sequence
<220> FEATURE:
<223> OTHER INFORMATION: Synthetic

<400> SEQUENCE: 7

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
    130                 135                 140

Asn Ala Leu Thr Gly Ala Pro Leu Asn Leu Thr Pro Asp Gln Val Val
145                 150                 155                 160

Ala Ile Ala Ser His Asp Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser His Asp Gly Gly Lys Gln Ala Leu Glu Thr
        195                 200                 205

Val Gln Arg Leu Leu Pro Val Leu Cys Gln Asp His Gly Leu Thr Pro
    210                 215                 220

Asp Gln Val Val Ala Ile Ala Ser Asn Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser Asn Gly Gly Lys Gln
            260                 265                 270

Ala Leu Glu Thr Val Gln Arg Leu Leu Pro Val Leu Cys Gln Asp His
        275                 280                 285

Gly Leu Thr Pro Asp Gln Val Val Ala Ile Ala Ser Asn Gly Gly Gly
    290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser Asn Gly
                325                 330                 335

Gly Gly Lys Gln Ala Leu Glu Thr Val Gln Arg Leu Leu Pro Val Leu
            340                 345                 350

```
Cys Gln Asp His Gly Leu Thr Pro Asp Gln Val Val Ala Ile Ala Ser
            355                 360                 365
Asn Gly Gly Lys Gln Ala Leu Glu Thr Val Gln Arg Leu Leu Pro
    370                 375                 380
Val Leu Cys Gln Asp His Gly Leu Thr Pro Asp Gln Val Val Ala Ile
385                 390                 395                 400
Ala Ser Asn Asn Gly Gly Lys Gln Ala Leu Glu Thr Val Gln Arg Leu
                405                 410                 415
Leu Pro Val Leu Cys Gln Asp His Gly Leu Thr Pro Asp Gln Val Val
                420                 425                 430
Ala Ile Ala Ser His Asp Gly Gly Lys Gln Ala Leu Glu Thr Val Gln
            435                 440                 445
Arg Leu Leu Pro Val Leu Cys Gln Asp His Gly Leu Thr Pro Asp Gln
        450                 455                 460
Val Val Ala Ile Ala Ser Asn Ile Gly Gly Lys Gln Ala Leu Glu Thr
465                 470                 475                 480
Val Gln Arg Leu Leu Pro Val Leu Cys Gln Asp His Gly Leu Thr Pro
                485                 490                 495
Asp Gln Val Val Ala Ile Ala Ser Asn Ile Gly Gly Lys Gln Ala Leu
            500                 505                 510
Glu Thr Val Gln Arg Leu Leu Pro Val Leu Cys Gln Asp His Gly Leu
        515                 520                 525
Thr Pro Asp Gln Val Val Ala Ile Ala Ser Asn Ile Gly Gly Lys Gln
    530                 535                 540
Ala Leu Glu Thr Val Gln Arg Leu Leu Pro Val Leu Cys Gln Asp His
545                 550                 555                 560
Gly Leu Thr Pro Asp Gln Val Val Ala Ile Ala Ser Asn Ile Gly Gly
                565                 570                 575
Lys Gln Ala Leu Glu Thr Val Gln Arg Leu Leu Pro Val Leu Cys Gln
            580                 585                 590
Asp His Gly Leu Thr Pro Asp Gln Val Val Ala Ile Ala Ser Asn Ile
        595                 600                 605
Gly Gly Lys Gln Ala Leu Glu Thr Val Gln Arg Leu Leu Pro Val Leu
    610                 615                 620
Cys Gln Asp His Gly Leu Thr Pro Asp Gln Val Val Ala Ile Ala Ser
625                 630                 635                 640
His Asp Gly Gly Lys Gln Ala Leu Glu Thr Val Gln Arg Leu Leu Pro
                645                 650                 655
Val Leu Cys Gln Asp His Gly Leu Thr Pro Asp Gln Val Val Ala Ile
            660                 665                 670
Ala Ser His Asp Gly Gly Lys Gln Ala Leu Glu Thr Val Gln Arg Leu
        675                 680                 685
Leu Pro Val Leu Cys Gln Asp His Gly Leu Thr Pro Asp Gln Val Val
    690                 695                 700
Ala Ile Ala Ser His Asp Gly Gly Lys Gln Ala Leu Glu Ser Ile Val
705                 710                 715                 720
Ala Gln Leu Ser Arg Pro Asp Pro Ala Leu Ala Ala Leu Thr Asn Asp
                725                 730                 735
His Leu Val Ala Leu Ala Cys Leu Gly Gly Arg Pro Ala Met Asp Ala
            740                 745                 750
Val Lys Lys Gly Leu Pro His Ala Pro Glu Leu Ile Arg Arg Val Asn
        755                 760                 765
Arg Arg Ile Gly Glu Arg Thr Ser His Arg Val Ala Gln Leu Val Lys
```

```
Ser Glu Leu Glu Glu Lys Lys Ser Glu Leu Arg His Lys Leu Lys Tyr
785                 790                 795                 800

Val Pro His Glu Tyr Ile Glu Leu Ile Glu Ile Ala Arg Asn Pro Thr
            805                 810                 815

Gln Asp Arg Ile Leu Glu Met Lys Val Met Glu Phe Phe Met Lys Val
        820                 825                 830

Tyr Gly Tyr Arg Gly Glu His Leu Gly Gly Ser Arg Lys Pro Asp Gly
    835                 840                 845

Ala Ile Tyr Thr Val Gly Ser Pro Ile Asp Tyr Gly Val Ile Val Asp
850                 855                 860

Thr Lys Ala Tyr Ser Gly Gly Tyr Asn Leu Pro Ile Gly Gln Ala Asp
865                 870                 875                 880

Glu Met Glu Arg Tyr Val Glu Glu Asn Gln Thr Arg Asp Lys His Leu
            885                 890                 895

Asn Pro Asn Glu Trp Trp Lys Val Tyr Pro Ser Ser Val Thr Glu Phe
        900                 905                 910

Lys Phe Leu Phe Val Ser Gly His Phe Lys Gly Asn Tyr Lys Ala Gln
    915                 920                 925

Leu Thr Arg Leu Asn His Ile Thr Asn Cys Asn Gly Ala Val Leu Ser
930                 935                 940

Val Glu Glu Leu Leu Ile Gly Gly Glu Met Ile Lys Ala Gly Thr Leu
945                 950                 955                 960

Thr Leu Glu Glu Val Arg Arg Lys Phe Asn Asn Gly Glu Ile Asn Phe
            965                 970                 975

<210> SEQ ID NO 8
<211> LENGTH: 976
<212> TYPE: PRT
<213> ORGANISM: Artificial Sequence
<220> FEATURE:
<223> OTHER INFORMATION: Synthetic

<400> SEQUENCE: 8

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
    130                 135                 140

Asn Ala Leu Thr Gly Ala Pro Leu Asn Leu Thr Pro Asp Gln Val Val
145                 150                 155                 160

Ala Ile Ala Ser His Asp Gly Gly Lys Gln Ala Leu Glu Thr Val Gln
```

```
            165                 170                 175
Arg Leu Leu Pro Val Leu Cys Gln Asp His Gly Leu Thr Pro Asp Gln
            180                 185                 190

Val Val Ala Ile Ala Ser Asn Ile Gly Gly Lys Gln Ala Leu Glu Thr
            195                 200                 205

Val Gln Arg Leu Leu Pro Val Leu Cys Gln Asp His Gly Leu Thr Pro
            210                 215                 220

Asp Gln Val Val Ala Ile Ala Ser His Asp Gly Gly Lys Gln Ala Leu
225                 230                 235                 240

Glu Thr Val Gln Arg Leu Leu Pro Val Leu Cys Gln Asp His Gly Leu
            245                 250                 255

Thr Pro Asp Gln Val Val Ala Ile Ala Ser His Asp Gly Gly Lys Gln
            260                 265                 270

Ala Leu Glu Thr Val Gln Arg Leu Leu Pro Val Leu Cys Gln Asp His
            275                 280                 285

Gly Leu Thr Pro Asp Gln Val Val Ala Ile Ala Ser Asn Ile Gly Gly
            290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser Asn Asn
            325                 330                 335

Gly Gly Lys Gln Ala Leu Glu Thr Val Gln Arg Leu Leu Pro Val Leu
            340                 345                 350

Cys Gln Asp His Gly Leu Thr Pro Asp Gln Val Val Ala Ile Ala Ser
            355                 360                 365

Asn Ile Gly Gly Lys Gln Ala Leu Glu Thr Val Gln Arg Leu Leu Pro
            370                 375                 380

Val Leu Cys Gln Asp His Gly Leu Thr Pro Asp Gln Val Val Ala Ile
385                 390                 395                 400

Ala Ser Asn Asn Gly Gly Lys Gln Ala Leu Glu Thr Val Gln Arg Leu
            405                 410                 415

Leu Pro Val Leu Cys Gln Asp His Gly Leu Thr Pro Asp Gln Val Val
            420                 425                 430

Ala Ile Ala Ser Asn Gly Gly Gly Lys Gln Ala Leu Glu Thr Val Gln
            435                 440                 445

Arg Leu Leu Pro Val Leu Cys Gln Asp His Gly Leu Thr Pro Asp Gln
            450                 455                 460

Val Val Ala Ile Ala Ser Asn Ile Gly Gly Lys Gln Ala Leu Glu Thr
465                 470                 475                 480

Val Gln Arg Leu Leu Pro Val Leu Cys Gln Asp His Gly Leu Thr Pro
            485                 490                 495

Asp Gln Val Val Ala Ile Ala Ser Asn Ile Gly Gly Lys Gln Ala Leu
            500                 505                 510

Glu Thr Val Gln Arg Leu Leu Pro Val Leu Cys Gln Asp His Gly Leu
            515                 520                 525

Thr Pro Asp Gln Val Val Ala Ile Ala Ser His Asp Gly Gly Lys Gln
            530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Ile Gly Gly
            565                 570                 575

Lys Gln Ala Leu Glu Thr Val Gln Arg Leu Leu Pro Val Leu Cys Gln
            580                 585                 590
```

```
Asp His Gly Leu Thr Pro Asp Gln Val Val Ala Ile Ala Ser Asn Asn
        595                 600                 605
Gly Gly Lys Gln Ala Leu Glu Thr Val Gln Arg Leu Leu Pro Val Leu
610                 615                 620
Cys Gln Asp His Gly Leu Thr Pro Asp Gln Val Val Ala Ile Ala Ser
625                 630                 635                 640
Asn Gly Gly Lys Gln Ala Leu Glu Thr Val Gln Arg Leu Leu Pro
                645                 650                 655
Val Leu Cys Gln Asp His Gly Leu Thr Pro Asp Gln Val Val Ala Ile
                660                 665                 670
Ala Ser His Asp Gly Gly Lys Gln Ala Leu Glu Thr Val Gln Arg Leu
            675                 680                 685
Leu Pro Val Leu Cys Gln Asp His Gly Leu Thr Pro Asp Gln Val Val
        690                 695                 700
Ala Ile Ala Ser Asn Gly Gly Lys Gln Ala Leu Glu Ser Ile Val
705                 710                 715                 720
Ala Gln Leu Ser Arg Pro Asp Pro Ala Leu Ala Ala Leu Thr Asn Asp
                725                 730                 735
His Leu Val Ala Leu Ala Cys Leu Gly Gly Arg Pro Ala Met Asp Ala
                740                 745                 750
Val Lys Lys Gly Leu Pro His Ala Pro Glu Leu Ile Arg Arg Val Asn
            755                 760                 765
Arg Arg Ile Gly Glu Arg Thr Ser His Arg Val Ala Gln Leu Val Lys
        770                 775                 780
Ser Glu Leu Glu Glu Lys Lys Ser Glu Leu Arg His Lys Leu Lys Tyr
785                 790                 795                 800
Val Pro His Glu Tyr Ile Glu Leu Ile Glu Ile Ala Arg Asn Pro Thr
                805                 810                 815
Gln Asp Arg Ile Leu Glu Met Lys Val Met Glu Phe Phe Met Lys Val
                820                 825                 830
Tyr Gly Tyr Arg Gly Glu His Leu Gly Gly Ser Arg Lys Pro Asp Gly
            835                 840                 845
Ala Ile Tyr Thr Val Gly Ser Pro Ile Asp Tyr Gly Val Ile Val Asp
        850                 855                 860
Thr Lys Ala Tyr Ser Gly Gly Tyr Asn Leu Pro Ile Gly Gln Ala Asp
865                 870                 875                 880
Glu Met Gln Arg Tyr Val Lys Glu Asn Gln Thr Arg Asn Lys His Ile
                885                 890                 895
Asn Pro Asn Glu Trp Trp Lys Val Tyr Pro Ser Ser Val Thr Glu Phe
                900                 905                 910
Lys Phe Leu Phe Val Ser Gly His Phe Lys Gly Asn Tyr Lys Ala Gln
            915                 920                 925
Leu Thr Arg Leu Asn Arg Lys Thr Asn Cys Asn Gly Ala Val Leu Ser
        930                 935                 940
Val Glu Glu Leu Leu Ile Gly Gly Glu Met Ile Lys Ala Gly Thr Leu
945                 950                 955                 960
Thr Leu Glu Glu Val Arg Arg Lys Phe Asn Asn Gly Glu Ile Asn Phe
                965                 970                 975

<210> SEQ ID NO 9
<211> LENGTH: 1044
<212> TYPE: PRT
<213> ORGANISM: Artificial Sequence
<220> FEATURE:
```

<223> OTHER INFORMATION: Synthetic

<400> SEQUENCE: 9

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
130                 135                 140

Asn Ala Leu Thr Gly Ala Pro Leu Asn Leu Thr Pro Asp Gln Val Val
145                 150                 155                 160

Ala Ile Ala Ser Asn Asn Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser Asn Gly Gly Gly Lys Gln Ala Leu Glu Thr
        195                 200                 205

Val Gln Arg Leu Leu Pro Val Leu Cys Gln Asp His Gly Leu Thr Pro
    210                 215                 220

Asp Gln Val Val Ala Ile Ala Ser His Asp Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser Asn Ile Gly Gly Lys Gln
            260                 265                 270

Ala Leu Glu Thr Val Gln Arg Leu Leu Pro Val Leu Cys Gln Asp His
        275                 280                 285

Gly Leu Thr Pro Asp Gln Val Val Ala Ile Ala Ser His Asp Gly Gly
    290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser His Asp
                325                 330                 335

Gly Gly Lys Gln Ala Leu Glu Thr Val Gln Arg Leu Leu Pro Val Leu
            340                 345                 350

Cys Gln Asp His Gly Leu Thr Pro Asp Gln Val Val Ala Ile Ala Ser
        355                 360                 365

Asn Ile Gly Gly Lys Gln Ala Leu Glu Thr Val Gln Arg Leu Leu Pro
    370                 375                 380

Val Leu Cys Gln Asp His Gly Leu Thr Pro Asp Gln Val Val Ala Ile
385                 390                 395                 400
```

```
Ala Ser Asn Asn Gly Gly Lys Gln Ala Leu Glu Thr Val Gln Arg Leu
                405                 410                 415
Leu Pro Val Leu Cys Gln Asp His Gly Leu Thr Pro Asp Gln Val Val
        420                 425                 430
Ala Ile Ala Ser Asn Ile Gly Gly Lys Gln Ala Leu Glu Thr Val Gln
435                 440                 445
Arg Leu Leu Pro Val Leu Cys Gln Asp His Gly Leu Thr Pro Asp Gln
    450                 455                 460
Val Val Ala Ile Ala Ser Asn Asn Gly Gly Lys Gln Ala Leu Glu Thr
465                 470                 475                 480
Val Gln Arg Leu Leu Pro Val Leu Cys Gln Asp His Gly Leu Thr Pro
            485                 490                 495
Asp Gln Val Val Ala Ile Ala Ser Asn Gly Gly Lys Gln Ala Leu
            500                 505                 510
Glu Thr Val Gln Arg Leu Leu Pro Val Leu Cys Gln Asp His Gly Leu
        515                 520                 525
Thr Pro Asp Gln Val Val Ala Ile Ala Ser Asn Ile Gly Gly Lys Gln
    530                 535                 540
Ala Leu Glu Thr Val Gln Arg Leu Leu Pro Val Leu Cys Gln Asp His
545                 550                 555                 560
Gly Leu Thr Pro Asp Gln Val Val Ala Ile Ala Ser Asn Ile Gly Gly
            565                 570                 575
Lys Gln Ala Leu Glu Thr Val Gln Arg Leu Leu Pro Val Leu Cys Gln
            580                 585                 590
Asp His Gly Leu Thr Pro Asp Gln Val Val Ala Ile Ala Ser His Asp
        595                 600                 605
Gly Gly Lys Gln Ala Leu Glu Thr Val Gln Arg Leu Leu Pro Val Leu
    610                 615                 620
Cys Gln Asp His Gly Leu Thr Pro Asp Gln Val Val Ala Ile Ala Ser
625                 630                 635                 640
Asn Ile Gly Gly Lys Gln Ala Leu Glu Thr Val Gln Arg Leu Leu Pro
            645                 650                 655
Val Leu Cys Gln Asp His Gly Leu Thr Pro Asp Gln Val Val Ala Ile
            660                 665                 670
Ala Ser Asn Asn Gly Gly Lys Gln Ala Leu Glu Thr Val Gln Arg Leu
        675                 680                 685
Leu Pro Val Leu Cys Gln Asp His Gly Leu Thr Pro Asp Gln Val Val
    690                 695                 700
Ala Ile Ala Ser Asn Gly Gly Gly Lys Gln Ala Leu Glu Thr Val Gln
705                 710                 715                 720
Arg Leu Leu Pro Val Leu Cys Gln Asp His Gly Leu Thr Pro Asp Gln
            725                 730                 735
Val Val Ala Ile Ala Ser His Asp Gly Gly Lys Gln Ala Leu Glu Thr
            740                 745                 750
Val Gln Arg Leu Leu Pro Val Leu Cys Gln Asp His Gly Leu Thr Pro
        755                 760                 765
Asp Gln Val Val Ala Ile Ala Ser Asn Gly Gly Gly Lys Gln Ala Leu
    770                 775                 780
Glu Ser Ile Val Ala Gln Leu Ser Arg Pro Asp Pro Ala Leu Ala Ala
785                 790                 795                 800
Leu Thr Asn Asp His Leu Val Ala Leu Ala Cys Leu Gly Gly Arg Pro
            805                 810                 815
Ala Met Asp Ala Val Lys Lys Gly Leu Pro His Ala Pro Glu Leu Ile
```

```
                    820                 825                 830
Arg Arg Val Asn Arg Arg Ile Gly Glu Arg Thr Ser His Arg Val Ala
            835                 840                 845

Gln Leu Val Lys Ser Glu Leu Glu Glu Lys Ser Glu Leu Arg His
        850                 855                 860

Lys Leu Lys Tyr Val Pro His Glu Tyr Ile Glu Leu Ile Glu Ile Ala
865                 870                 875                 880

Arg Asn Pro Thr Gln Asp Arg Ile Leu Glu Met Lys Val Met Glu Phe
                885                 890                 895

Phe Met Lys Val Tyr Gly Tyr Arg Gly Glu His Leu Gly Gly Ser Arg
            900                 905                 910

Lys Pro Asp Gly Ala Ile Tyr Thr Val Gly Ser Pro Ile Asp Tyr Gly
        915                 920                 925

Val Ile Val Asp Thr Lys Ala Tyr Ser Gly Gly Tyr Asn Leu Pro Ile
        930                 935                 940

Gly Gln Ala Asp Glu Met Gln Arg Tyr Val Lys Glu Asn Gln Thr Arg
945                 950                 955                 960

Asn Lys His Ile Asn Pro Asn Glu Trp Trp Lys Val Tyr Pro Ser Ser
                965                 970                 975

Val Thr Glu Phe Lys Phe Leu Phe Val Ser Gly His Phe Lys Gly Asn
            980                 985                 990

Tyr Lys Ala Gln Leu Thr Arg Leu Asn Arg Lys Thr Asn Cys Asn Gly
        995                 1000                1005

Ala Val Leu Ser Val Glu Glu Leu Leu Ile Gly Gly Glu Met Ile
    1010                1015                1020

Lys Ala Gly Thr Leu Thr Leu Glu Glu Val Arg Arg Lys Phe Asn
    1025                1030                1035

Asn Gly Glu Ile Asn Phe
    1040

<210> SEQ ID NO 10
<211> LENGTH: 1044
<212> TYPE: PRT
<213> ORGANISM: Artificial Sequence
<220> FEATURE:
<223> OTHER INFORMATION: Synthetic

<400> SEQUENCE: 10

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
```

```
             130                 135                 140
Asn Ala Leu Thr Gly Ala Pro Leu Asn Leu Thr Pro Asp Gln Val Val
145                 150                 155                 160

Ala Ile Ala Ser His Asp Gly Gly Lys Gln Ala Leu Glu Thr Val Gln
                165                 170                 175

Arg Leu Leu Pro Val Leu Cys Gln Asp His Gly Leu Thr Pro Asp Gln
                180                 185                 190

Val Val Ala Ile Ala Ser Asn Gly Gly Lys Gln Ala Leu Glu Thr
                195                 200                 205

Val Gln Arg Leu Leu Pro Val Leu Cys Gln Asp His Gly Leu Thr Pro
210                 215                 220

Asp Gln Val Val Ala Ile Ala Ser Asn Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser His Asp Gly Gly Lys Gln
                260                 265                 270

Ala Leu Glu Thr Val Gln Arg Leu Leu Pro Val Leu Cys Gln Asp His
                275                 280                 285

Gly Leu Thr Pro Asp Gln Val Val Ala Ile Ala Ser His Asp Gly Gly
                290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser Asn Gly
                325                 330                 335

Gly Gly Lys Gln Ala Leu Glu Thr Val Gln Arg Leu Leu Pro Val Leu
                340                 345                 350

Cys Gln Asp His Gly Leu Thr Pro Asp Gln Val Val Ala Ile Ala Ser
                355                 360                 365

Asn Gly Gly Gly Lys Gln Ala Leu Glu Thr Val Gln Arg Leu Leu Pro
                370                 375                 380

Val Leu Cys Gln Asp His Gly Leu Thr Pro Asp Gln Val Val Ala Ile
385                 390                 395                 400

Ala Ser Asn Asn Gly Gly Lys Gln Ala Leu Glu Thr Val Gln Arg Leu
                405                 410                 415

Leu Pro Val Leu Cys Gln Asp His Gly Leu Thr Pro Asp Gln Val Val
                420                 425                 430

Ala Ile Ala Ser Asn Ile Gly Gly Lys Gln Ala Leu Glu Thr Val Gln
                435                 440                 445

Arg Leu Leu Pro Val Leu Cys Gln Asp His Gly Leu Thr Pro Asp Gln
                450                 455                 460

Val Val Ala Ile Ala Ser Asn Gly Gly Gly Lys Gln Ala Leu Glu Thr
465                 470                 475                 480

Val Gln Arg Leu Leu Pro Val Leu Cys Gln Asp His Gly Leu Thr Pro
                485                 490                 495

Asp Gln Val Val Ala Ile Ala Ser Asn Asn Gly Gly Lys Gln Ala Leu
                500                 505                 510

Glu Thr Val Gln Arg Leu Leu Pro Val Leu Cys Gln Asp His Gly Leu
                515                 520                 525

Thr Pro Asp Gln Val Val Ala Ile Ala Ser Asn Gly Gly Gly Lys Gln
                530                 535                 540

Ala Leu Glu Thr Val Gln Arg Leu Leu Pro Val Leu Cys Gln Asp His
545                 550                 555                 560
```

Gly Leu Thr Pro Asp Gln Val Ala Ile Ala Ser Asn Gly Gly
                565                 570                 575

Lys Gln Ala Leu Glu Thr Val Gln Arg Leu Leu Pro Val Leu Cys Gln
            580                 585                 590

Asp His Gly Leu Thr Pro Asp Gln Val Val Ala Ile Ala Ser Asn Asn
        595                 600                 605

Gly Gly Lys Gln Ala Leu Glu Thr Val Gln Arg Leu Leu Pro Val Leu
    610                 615                 620

Cys Gln Asp His Gly Leu Thr Pro Asp Gln Val Val Ala Ile Ala Ser
625                 630                 635                 640

Asn Asn Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
            660                 665                 670

Ala Ser Asn Ile Gly Gly Lys Gln Ala Leu Glu Thr Val Gln Arg Leu
        675                 680                 685

Leu Pro Val Leu Cys Gln Asp His Gly Leu Thr Pro Asp Gln Val Val
    690                 695                 700

Ala Ile Ala Ser Asn Asn Gly Gly Lys Gln Ala Leu Glu Thr Val Gln
705                 710                 715                 720

Arg Leu Leu Pro Val Leu Cys Gln Asp His Gly Leu Thr Pro Asp Gln
                725                 730                 735

Val Val Ala Ile Ala Ser Asn Gly Gly Lys Gln Ala Leu Glu Thr
            740                 745                 750

Val Gln Arg Leu Leu Pro Val Leu Cys Gln Asp His Gly Leu Thr Pro
        755                 760                 765

Asp Gln Val Val Ala Ile Ala Ser Asn Gly Gly Lys Gln Ala Leu
    770                 775                 780

Glu Ser Ile Val Ala Gln Leu Ser Arg Pro Asp Pro Ala Leu Ala Ala
785                 790                 795                 800

Leu Thr Asn Asp His Leu Val Ala Leu Ala Cys Leu Gly Gly Arg Pro
                805                 810                 815

Ala Met Asp Ala Val Lys Lys Gly Leu Pro His Ala Pro Glu Leu Ile
            820                 825                 830

Arg Arg Val Asn Arg Arg Ile Gly Glu Arg Thr Ser His Arg Val Ala
        835                 840                 845

Gln Leu Val Lys Ser Glu Leu Glu Glu Lys Lys Ser Glu Leu Arg His
    850                 855                 860

Lys Leu Lys Tyr Val Pro His Glu Tyr Ile Glu Leu Ile Glu Ile Ala
865                 870                 875                 880

Arg Asn Pro Thr Gln Asp Arg Ile Leu Glu Met Lys Val Met Glu Phe
                885                 890                 895

Phe Met Lys Val Tyr Gly Tyr Arg Gly Glu His Leu Gly Gly Ser Arg
            900                 905                 910

Lys Pro Asp Gly Ala Ile Tyr Thr Val Gly Ser Pro Ile Asp Tyr Gly
        915                 920                 925

Val Ile Val Asp Thr Lys Ala Tyr Ser Gly Gly Tyr Asn Leu Pro Ile
    930                 935                 940

Gly Gln Ala Asp Glu Met Glu Arg Tyr Val Glu Glu Asn Gln Thr Arg
945                 950                 955                 960

Asp Lys His Leu Asn Pro Asn Glu Trp Trp Lys Val Tyr Pro Ser Ser
                965                 970                 975

Val Thr Glu Phe Lys Phe Leu Phe Val Ser Gly His Phe Lys Gly Asn
                980                 985                 990

Tyr Lys Ala Gln Leu Thr Arg Leu Asn His Ile Thr Asn Cys Asn Gly
            995                 1000                1005

Ala Val Leu Ser Val Glu Glu Leu Leu Ile Gly Gly Glu Met Ile
        1010                1015                1020

Lys Ala Gly Thr Leu Thr Leu Glu Glu Val Arg Arg Lys Phe Asn
        1025                1030                1035

Asn Gly Glu Ile Asn Phe
        1040

<210> SEQ ID NO 11
<211> LENGTH: 1044
<212> TYPE: PRT
<213> ORGANISM: Artificial Sequence
<220> FEATURE:
<223> OTHER INFORMATION: Synthetic

<400> SEQUENCE: 11

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
    130                 135                 140

Asn Ala Leu Thr Gly Ala Pro Leu Asn Leu Thr Pro Asp Gln Val Val
145                 150                 155                 160

Ala Ile Ala Ser Asn Ile Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser His Asp Gly Gly Lys Gln Ala Leu Glu Thr
        195                 200                 205

Val Gln Arg Leu Leu Pro Val Leu Cys Gln Asp His Gly Leu Thr Pro
    210                 215                 220

Asp Gln Val Val Ala Ile Ala Ser His Asp Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser Asn Gly Gly Lys Gln
            260                 265                 270

Ala Leu Glu Thr Val Gln Arg Leu Leu Pro Val Leu Cys Gln Asp His
        275                 280                 285

-continued

```
Gly Leu Thr Pro Asp Gln Val Val Ala Ile Ala Ser Asn Asn Gly Gly
290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser His Asp
                325                 330                 335

Gly Gly Lys Gln Ala Leu Glu Thr Val Gln Arg Leu Leu Pro Val Leu
                340                 345                 350

Cys Gln Asp His Gly Leu Thr Pro Asp Gln Val Val Ala Ile Ala Ser
                355                 360                 365

Asn Gly Gly Lys Gln Ala Leu Glu Thr Val Gln Arg Leu Leu Pro
370                 375                 380

Val Leu Cys Gln Asp His Gly Leu Thr Pro Asp Gln Val Val Ala Ile
385                 390                 395                 400

Ala Ser His Asp Gly Gly Lys Gln Ala Leu Glu Thr Val Gln Arg Leu
                405                 410                 415

Leu Pro Val Leu Cys Gln Asp His Gly Leu Thr Pro Asp Gln Val Val
                420                 425                 430

Ala Ile Ala Ser Asn Gly Gly Gly Lys Gln Ala Leu Glu Thr Val Gln
                435                 440                 445

Arg Leu Leu Pro Val Leu Cys Gln Asp His Gly Leu Thr Pro Asp Gln
                450                 455                 460

Val Val Ala Ile Ala Ser Asn Asn Gly Gly Lys Gln Ala Leu Glu Thr
465                 470                 475                 480

Val Gln Arg Leu Leu Pro Val Leu Cys Gln Asp His Gly Leu Thr Pro
                485                 490                 495

Asp Gln Val Val Ala Ile Ala Ser Asn Asn Gly Gly Lys Gln Ala Leu
                500                 505                 510

Glu Thr Val Gln Arg Leu Leu Pro Val Leu Cys Gln Asp His Gly Leu
                515                 520                 525

Thr Pro Asp Gln Val Val Ala Ile Ala Ser His Asp Gly Gly Lys Gln
                530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Ile Gly Gly
                565                 570                 575

Lys Gln Ala Leu Glu Thr Val Gln Arg Leu Leu Pro Val Leu Cys Gln
                580                 585                 590

Asp His Gly Leu Thr Pro Asp Gln Val Val Ala Ile Ala Ser Asn Asn
                595                 600                 605

Gly Gly Lys Gln Ala Leu Glu Thr Val Gln Arg Leu Leu Pro Val Leu
                610                 615                 620

Cys Gln Asp His Gly Leu Thr Pro Asp Gln Val Val Ala Ile Ala Ser
625                 630                 635                 640

Asn Ile Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
                660                 665                 670

Ala Ser Asn Gly Gly Gly Lys Gln Ala Leu Glu Thr Val Gln Arg Leu
                675                 680                 685

Leu Pro Val Leu Cys Gln Asp His Gly Leu Thr Pro Asp Gln Val Val
                690                 695                 700

Ala Ile Ala Ser Asn Gly Gly Gly Lys Gln Ala Leu Glu Thr Val Gln
```

```
                705                 710                 715                 720
Arg Leu Leu Pro Val Leu Cys Gln Asp His Gly Leu Thr Pro Asp Gln
                    725                 730                 735
Val Val Ala Ile Ala Ser Asn Gly Gly Gly Lys Gln Ala Leu Glu Thr
                740                 745                 750
Val Gln Arg Leu Leu Pro Val Leu Cys Gln Asp His Gly Leu Thr Pro
            755                 760                 765
Asp Gln Val Val Ala Ile Ala Ser His Asp Gly Gly Lys Gln Ala Leu
        770                 775                 780
Glu Ser Ile Val Ala Gln Leu Ser Arg Pro Asp Pro Ala Leu Ala Ala
785                 790                 795                 800
Leu Thr Asn Asp His Leu Val Ala Leu Ala Cys Leu Gly Gly Arg Pro
                    805                 810                 815
Ala Met Asp Ala Val Lys Lys Gly Leu Pro His Ala Pro Glu Leu Ile
                820                 825                 830
Arg Arg Val Asn Arg Arg Ile Gly Glu Arg Thr Ser His Arg Val Ala
            835                 840                 845
Gln Leu Val Lys Ser Glu Leu Glu Glu Lys Lys Ser Glu Leu Arg His
        850                 855                 860
Lys Leu Lys Tyr Val Pro His Glu Tyr Ile Glu Leu Ile Glu Ile Ala
865                 870                 875                 880
Arg Asn Pro Thr Gln Asp Arg Ile Leu Glu Met Lys Val Met Glu Phe
                    885                 890                 895
Phe Met Lys Val Tyr Gly Tyr Arg Gly Glu His Leu Gly Gly Ser Arg
                900                 905                 910
Lys Pro Asp Gly Ala Ile Tyr Thr Val Gly Ser Pro Ile Asp Tyr Gly
            915                 920                 925
Val Ile Val Asp Thr Lys Ala Tyr Ser Gly Gly Tyr Asn Leu Pro Ile
        930                 935                 940
Gly Gln Ala Asp Glu Met Gln Arg Tyr Val Lys Glu Asn Gln Thr Arg
945                 950                 955                 960
Asn Lys His Ile Asn Pro Asn Glu Trp Trp Lys Val Tyr Pro Ser Ser
                    965                 970                 975
Val Thr Glu Phe Lys Phe Leu Phe Val Ser Gly His Phe Lys Gly Asn
                980                 985                 990
Tyr Lys Ala Gln Leu Thr Arg Leu Asn Arg Lys Thr Asn Cys Asn Gly
            995                 1000                1005
Ala Val Leu Ser Val Glu Glu Leu Leu Ile Gly Gly Glu Met Ile
        1010                1015                1020
Lys Ala Gly Thr Leu Thr Leu Glu Glu Val Arg Arg Lys Phe Asn
        1025                1030                1035
Asn Gly Glu Ile Asn Phe
    1040

<210> SEQ ID NO 12
<211> LENGTH: 1010
<212> TYPE: PRT
<213> ORGANISM: Artificial Sequence
<220> FEATURE:
<223> OTHER INFORMATION: Synthetic

<400> SEQUENCE: 12

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
```

```
                 20                  25                  30
Gly Arg Gly Ser Val Arg Ser Thr Val Ala Gln His His Glu Ala Leu
             35                  40                  45
Val Gly His Gly Phe Thr His Ala His Ile Val Ala Leu Ser Gln His
         50                  55                  60
Pro Ala Ala Leu Gly Thr Val Ala Val Thr Tyr Gln His Ile Ile Thr
 65                  70                  75                  80
Ala Leu Pro Glu Ala Thr His Glu Asp Ile Val Gly Val Gly Lys Gln
                 85                  90                  95
Trp Ser Gly Ala Arg Ala Leu Glu Ala Leu Leu Thr Asp Ala Gly Glu
             100                 105                 110
Leu Arg Gly Pro Pro Leu Gln Leu Asp Thr Gly Gln Leu Val Lys Ile
         115                 120                 125
Ala Lys Arg Gly Gly Val Thr Ala Met Glu Ala Val His Ala Ser Arg
130                 135                 140
Asn Ala Leu Thr Gly Ala Pro Leu Asn Leu Thr Pro Asp Gln Val Val
145                 150                 155                 160
Ala Ile Ala Ser His Asp Gly Gly Lys Gln Ala Leu Glu Thr Val Gln
                 165                 170                 175
Arg Leu Leu Pro Val Leu Cys Gln Asp His Gly Leu Thr Pro Asp Gln
             180                 185                 190
Val Val Ala Ile Ala Ser Asn Gly Gly Lys Gln Ala Leu Glu Thr
         195                 200                 205
Val Gln Arg Leu Leu Pro Val Leu Cys Gln Asp His Gly Leu Thr Pro
         210                 215                 220
Asp Gln Val Val Ala Ile Ala Ser Asn Ile Gly Gly Lys Gln Ala Leu
225                 230                 235                 240
Glu Thr Val Gln Arg Leu Leu Pro Val Leu Cys Gln Asp His Gly Leu
                 245                 250                 255
Thr Pro Asp Gln Val Val Ala Ile Ala Ser Asn Gly Gly Lys Gln
             260                 265                 270
Ala Leu Glu Thr Val Gln Arg Leu Leu Pro Val Leu Cys Gln Asp His
         275                 280                 285
Gly Leu Thr Pro Asp Gln Val Val Ala Ile Ala Ser Asn Ile Gly Gly
         290                 295                 300
Lys Gln Ala Leu Glu Thr Val Gln Arg Leu Leu Pro Val Leu Cys Gln
305                 310                 315                 320
Asp His Gly Leu Thr Pro Asp Gln Val Val Ala Ile Ala Ser Asn Asn
                 325                 330                 335
Gly Gly Lys Gln Ala Leu Glu Thr Val Gln Arg Leu Leu Pro Val Leu
             340                 345                 350
Cys Gln Asp His Gly Leu Thr Pro Asp Gln Val Val Ala Ile Ala Ser
         355                 360                 365
Asn Ile Gly Gly Lys Gln Ala Leu Glu Thr Val Gln Arg Leu Leu Pro
         370                 375                 380
Val Leu Cys Gln Asp His Gly Leu Thr Pro Asp Gln Val Val Ala Ile
385                 390                 395                 400
Ala Ser Asn Gly Gly Lys Gln Ala Leu Glu Thr Val Gln Arg Leu
                 405                 410                 415
Leu Pro Val Leu Cys Gln Asp His Gly Leu Thr Pro Asp Gln Val Val
             420                 425                 430
Ala Ile Ala Ser Asn Asn Gly Gly Lys Gln Ala Leu Glu Thr Val Gln
         435                 440                 445
```

```
Arg Leu Leu Pro Val Leu Cys Gln Asp His Gly Leu Thr Pro Asp Gln
    450                 455                 460

Val Val Ala Ile Ala Ser Asn Ile Gly Gly Lys Gln Ala Leu Glu Thr
465                 470                 475                 480

Val Gln Arg Leu Leu Pro Val Leu Cys Gln Asp His Gly Leu Thr Pro
                485                 490                 495

Asp Gln Val Val Ala Ile Ala Ser Asn Asn Gly Gly Lys Gln Ala Leu
            500                 505                 510

Glu Thr Val Gln Arg Leu Leu Pro Val Leu Cys Gln Asp His Gly Leu
        515                 520                 525

Thr Pro Asp Gln Val Val Ala Ile Ala Ser Asn Ile Gly Gly Lys Gln
    530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Gly Gly Gly
                565                 570                 575

Lys Gln Ala Leu Glu Thr Val Gln Arg Leu Leu Pro Val Leu Cys Gln
            580                 585                 590

Asp His Gly Leu Thr Pro Asp Gln Val Val Ala Ile Ala Ser Asn Gly
        595                 600                 605

Gly Gly Lys Gln Ala Leu Glu Thr Val Gln Arg Leu Leu Pro Val Leu
    610                 615                 620

Cys Gln Asp His Gly Leu Thr Pro Asp Gln Val Val Ala Ile Ala Ser
625                 630                 635                 640

Asn Ile Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
            660                 665                 670

Ala Ser Asn Gly Gly Gly Lys Gln Ala Leu Glu Thr Val Gln Arg Leu
        675                 680                 685

Leu Pro Val Leu Cys Gln Asp His Gly Leu Thr Pro Asp Gln Val Val
    690                 695                 700

Ala Ile Ala Ser His Asp Gly Gly Lys Gln Ala Leu Glu Thr Val Gln
705                 710                 715                 720

Arg Leu Leu Pro Val Leu Cys Gln Asp His Gly Leu Thr Pro Asp Gln
                725                 730                 735

Val Val Ala Ile Ala Ser Asn Gly Gly Gly Lys Gln Ala Leu Glu Ser
            740                 745                 750

Ile Val Ala Gln Leu Ser Arg Pro Asp Pro Ala Leu Ala Ala Leu Thr
        755                 760                 765

Asn Asp His Leu Val Ala Leu Ala Cys Leu Gly Gly Arg Pro Ala Met
    770                 775                 780

Asp Ala Val Lys Lys Gly Leu Pro His Ala Pro Glu Leu Ile Arg Arg
785                 790                 795                 800

Val Asn Arg Arg Ile Gly Glu Arg Thr Ser His Arg Val Ala Gln Leu
                805                 810                 815

Val Lys Ser Glu Leu Glu Glu Lys Lys Ser Glu Leu Arg His Lys Leu
            820                 825                 830

Lys Tyr Val Pro His Glu Tyr Ile Glu Leu Ile Glu Ile Ala Arg Asn
        835                 840                 845

Pro Thr Gln Asp Arg Ile Leu Glu Met Lys Val Met Glu Phe Phe Met
    850                 855                 860
```

```
Lys Val Tyr Gly Tyr Arg Gly Glu His Leu Gly Gly Ser Arg Lys Pro
865                 870                 875                 880

Asp Gly Ala Ile Tyr Thr Val Gly Ser Pro Ile Asp Tyr Gly Val Ile
            885                 890                 895

Val Asp Thr Lys Ala Tyr Ser Gly Gly Tyr Asn Leu Pro Ile Gly Gln
        900                 905                 910

Ala Asp Glu Met Glu Arg Tyr Val Glu Glu Asn Gln Thr Arg Asp Lys
    915                 920                 925

His Leu Asn Pro Asn Glu Trp Trp Lys Val Tyr Pro Ser Ser Val Thr
930                 935                 940

Glu Phe Lys Phe Leu Phe Val Ser Gly His Phe Lys Gly Asn Tyr Lys
945                 950                 955                 960

Ala Gln Leu Thr Arg Leu Asn His Ile Thr Asn Cys Asn Gly Ala Val
            965                 970                 975

Leu Ser Val Glu Glu Leu Leu Ile Gly Gly Glu Met Ile Lys Ala Gly
        980                 985                 990

Thr Leu Thr Leu Glu Glu Val Arg Arg Lys Phe Asn Asn Gly Glu Ile
        995                1000                1005

Asn Phe
   1010

<210> SEQ ID NO 13
<211> LENGTH: 1010
<212> TYPE: PRT
<213> ORGANISM: Artificial Sequence
<220> FEATURE:
<223> OTHER INFORMATION: Synthetic

<400> SEQUENCE: 13

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
130                 135                 140

Asn Ala Leu Thr Gly Ala Pro Leu Asn Leu Thr Pro Asp Gln Val Val
145                 150                 155                 160

Ala Ile Ala Ser Asn Ile Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser Asn Asn Gly Gly Lys Gln Ala Leu Glu Thr
        195                 200                 205
```

```
Val Gln Arg Leu Leu Pro Val Leu Cys Gln Asp His Gly Leu Thr Pro
    210                 215                 220
Asp Gln Val Val Ala Ile Ala Ser His Asp Gly Lys Gln Ala Leu
225                 230                 235                 240
Glu Thr Val Gln Arg Leu Leu Pro Val Leu Cys Gln Asp His Gly Leu
                245                 250                 255
Thr Pro Asp Gln Val Val Ala Ile Ala Ser Asn Ile Gly Gly Lys Gln
            260                 265                 270
Ala Leu Glu Thr Val Gln Arg Leu Leu Pro Val Leu Cys Gln Asp His
        275                 280                 285
Gly Leu Thr Pro Asp Gln Val Val Ala Ile Ala Ser Asn Ile Gly Gly
    290                 295                 300
Lys Gln Ala Leu Glu Thr Val Gln Arg Leu Leu Pro Val Leu Cys Gln
305                 310                 315                 320
Asp His Gly Leu Thr Pro Asp Gln Val Val Ala Ile Ala Ser Asn Gly
                325                 330                 335
Gly Gly Lys Gln Ala Leu Glu Thr Val Gln Arg Leu Leu Pro Val Leu
            340                 345                 350
Cys Gln Asp His Gly Leu Thr Pro Asp Gln Val Val Ala Ile Ala Ser
        355                 360                 365
Asn Asn Gly Gly Lys Gln Ala Leu Glu Thr Val Gln Arg Leu Leu Pro
    370                 375                 380
Val Leu Cys Gln Asp His Gly Leu Thr Pro Asp Gln Val Val Ala Ile
385                 390                 395                 400
Ala Ser His Asp Gly Gly Lys Gln Ala Leu Glu Thr Val Gln Arg Leu
                405                 410                 415
Leu Pro Val Leu Cys Gln Asp His Gly Leu Thr Pro Asp Gln Val Val
            420                 425                 430
Ala Ile Ala Ser Asn Asn Gly Gly Lys Gln Ala Leu Glu Thr Val Gln
        435                 440                 445
Arg Leu Leu Pro Val Leu Cys Gln Asp His Gly Leu Thr Pro Asp Gln
    450                 455                 460
Val Val Ala Ile Ala Ser Asn Asn Gly Gly Lys Gln Ala Leu Glu Thr
465                 470                 475                 480
Val Gln Arg Leu Leu Pro Val Leu Cys Gln Asp His Gly Leu Thr Pro
                485                 490                 495
Asp Gln Val Val Ala Ile Ala Ser His Asp Gly Gly Lys Gln Ala Leu
            500                 505                 510
Glu Thr Val Gln Arg Leu Leu Pro Val Leu Cys Gln Asp His Gly Leu
        515                 520                 525
Thr Pro Asp Gln Val Val Ala Ile Ala Ser His Asp Gly Gly Lys Gln
    530                 535                 540
Ala Leu Glu Thr Val Gln Arg Leu Leu Pro Val Leu Cys Gln Asp His
545                 550                 555                 560
Gly Leu Thr Pro Asp Gln Val Val Ala Ile Ala Ser Asn Ile Gly Gly
                565                 570                 575
Lys Gln Ala Leu Glu Thr Val Gln Arg Leu Leu Pro Val Leu Cys Gln
            580                 585                 590
Asp His Gly Leu Thr Pro Asp Gln Val Val Ala Ile Ala Ser Asn Gly
        595                 600                 605
Gly Gly Lys Gln Ala Leu Glu Thr Val Gln Arg Leu Leu Pro Val Leu
    610                 615                 620
Cys Gln Asp His Gly Leu Thr Pro Asp Gln Val Val Ala Ile Ala Ser
```

```
            625                 630                 635                 640
His Asp Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
            660                 665                 670

Ala Ser His Asp Gly Lys Gln Ala Leu Glu Thr Val Gln Arg Leu
        675                 680                 685

Leu Pro Val Leu Cys Gln Asp His Gly Leu Thr Pro Asp Gln Val Val
690                 695                 700

Ala Ile Ala Ser His Asp Gly Gly Lys Gln Ala Leu Glu Thr Val Gln
705                 710                 715                 720

Arg Leu Leu Pro Val Leu Cys Gln Asp His Gly Leu Thr Pro Asp Gln
                725                 730                 735

Val Val Ala Ile Ala Ser Asn Gly Gly Lys Gln Ala Leu Glu Ser
            740                 745                 750

Ile Val Ala Gln Leu Ser Arg Pro Asp Pro Ala Leu Ala Ala Leu Thr
        755                 760                 765

Asn Asp His Leu Val Ala Leu Ala Cys Leu Gly Gly Arg Pro Ala Met
770                 775                 780

Asp Ala Val Lys Lys Gly Leu Pro His Ala Pro Glu Leu Ile Arg Arg
785                 790                 795                 800

Val Asn Arg Arg Ile Gly Glu Arg Thr Ser His Arg Val Ala Gln Leu
                805                 810                 815

Val Lys Ser Glu Leu Glu Glu Lys Lys Ser Glu Leu Arg His Lys Leu
            820                 825                 830

Lys Tyr Val Pro His Glu Tyr Ile Glu Leu Ile Glu Ile Ala Arg Asn
        835                 840                 845

Pro Thr Gln Asp Arg Ile Leu Glu Met Lys Val Met Glu Phe Phe Met
850                 855                 860

Lys Val Tyr Gly Tyr Arg Gly Glu His Leu Gly Gly Ser Arg Lys Pro
865                 870                 875                 880

Asp Gly Ala Ile Tyr Thr Val Gly Ser Pro Ile Asp Tyr Gly Val Ile
                885                 890                 895

Val Asp Thr Lys Ala Tyr Ser Gly Gly Tyr Asn Leu Pro Ile Gly Gln
            900                 905                 910

Ala Asp Glu Met Gln Arg Tyr Val Lys Glu Asn Gln Thr Arg Asn Lys
        915                 920                 925

His Ile Asn Pro Asn Glu Trp Trp Lys Val Tyr Pro Ser Ser Val Thr
930                 935                 940

Glu Phe Lys Phe Leu Phe Val Ser Gly His Phe Lys Gly Asn Tyr Lys
945                 950                 955                 960

Ala Gln Leu Thr Arg Leu Asn Arg Lys Thr Asn Cys Asn Gly Ala Val
                965                 970                 975

Leu Ser Val Glu Glu Leu Leu Ile Gly Gly Glu Met Ile Lys Ala Gly
            980                 985                 990

Thr Leu Thr Leu Glu Glu Val Arg  Arg Lys Phe Asn Asn  Gly Glu Ile
        995                 1000                1005

Asn Phe
    1010

<210> SEQ ID NO 14
<211> LENGTH: 942
<212> TYPE: PRT
<213> ORGANISM: Artificial Sequence
```

<220> FEATURE:
<223> OTHER INFORMATION: Synthetic

<400> SEQUENCE: 14

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
130                 135                 140

Asn Ala Leu Thr Gly Ala Pro Leu Asn Leu Thr Pro Asp Gln Val Val
145                 150                 155                 160

Ala Ile Ala Ser Asn Ile Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser Asn Ile Gly Gly Lys Gln Ala Leu Glu Thr
        195                 200                 205

Val Gln Arg Leu Leu Pro Val Leu Cys Gln Asp His Gly Leu Thr Pro
210                 215                 220

Asp Gln Val Val Ala Ile Ala Ser His Asp Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser Asn Gly Gly Lys Gln
            260                 265                 270

Ala Leu Glu Thr Val Gln Arg Leu Leu Pro Val Leu Cys Gln Asp His
        275                 280                 285

Gly Leu Thr Pro Asp Gln Val Val Ala Ile Ala Ser Asn Asn Gly Gly
290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser Asn Ile
                325                 330                 335

Gly Gly Lys Gln Ala Leu Glu Thr Val Gln Arg Leu Leu Pro Val Leu
            340                 345                 350

Cys Gln Asp His Gly Leu Thr Pro Asp Gln Val Val Ala Ile Ala Ser
        355                 360                 365

Asn Gly Gly Gly Lys Gln Ala Leu Glu Thr Val Gln Arg Leu Leu Pro
370                 375                 380

Val Leu Cys Gln Asp His Gly Leu Thr Pro Asp Gln Val Val Ala Ile
385                 390                 395                 400
```

```
Ala Ser Asn Asn Gly Gly Lys Gln Ala Leu Glu Thr Val Gln Arg Leu
            405                 410                 415

Leu Pro Val Leu Cys Gln Asp His Gly Leu Thr Pro Asp Gln Val Val
        420                 425                 430

Ala Ile Ala Ser His Asp Gly Gly Lys Gln Ala Leu Glu Thr Val Gln
        435                 440                 445

Arg Leu Leu Pro Val Leu Cys Gln Asp His Gly Leu Thr Pro Asp Gln
    450                 455                 460

Val Val Ala Ile Ala Ser His Asp Gly Gly Lys Gln Ala Leu Glu Thr
465                 470                 475                 480

Val Gln Arg Leu Leu Pro Val Leu Cys Gln Asp His Gly Leu Thr Pro
            485                 490                 495

Asp Gln Val Val Ala Ile Ala Ser Asn Ile Gly Gly Lys Gln Ala Leu
        500                 505                 510

Glu Thr Val Gln Arg Leu Leu Pro Val Leu Cys Gln Asp His Gly Leu
        515                 520                 525

Thr Pro Asp Gln Val Val Ala Ile Ala Ser Asn Asn Gly Gly Lys Gln
    530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Asn Gly Gly
            565                 570                 575

Lys Gln Ala Leu Glu Thr Val Gln Arg Leu Leu Pro Val Leu Cys Gln
        580                 585                 590

Asp His Gly Leu Thr Pro Asp Gln Val Val Ala Ile Ala Ser Asn Ile
        595                 600                 605

Gly Gly Lys Gln Ala Leu Glu Thr Val Gln Arg Leu Leu Pro Val Leu
    610                 615                 620

Cys Gln Asp His Gly Leu Thr Pro Asp Gln Val Val Ala Ile Ala Ser
625                 630                 635                 640

Asn Gly Gly Gly Lys Gln Ala Leu Glu Thr Val Gln Arg Leu Leu Pro
            645                 650                 655

Val Leu Cys Gln Asp His Gly Leu Thr Pro Asp Gln Val Val Ala Ile
        660                 665                 670

Ala Ser Asn Gly Gly Gly Lys Gln Ala Leu Glu Ser Ile Val Ala Gln
        675                 680                 685

Leu Ser Arg Pro Asp Pro Ala Leu Ala Ala Leu Thr Asn Asp His Leu
    690                 695                 700

Val Ala Leu Ala Cys Leu Gly Gly Arg Pro Ala Met Asp Ala Val Lys
705                 710                 715                 720

Lys Gly Leu Pro His Ala Pro Glu Leu Ile Arg Arg Val Asn Arg Arg
            725                 730                 735

Ile Gly Glu Arg Thr Ser His Arg Val Ala Gln Leu Val Lys Ser Glu
        740                 745                 750

Leu Glu Glu Lys Lys Ser Glu Leu Arg His Lys Leu Lys Tyr Val Pro
        755                 760                 765

His Glu Tyr Ile Glu Leu Ile Glu Ile Ala Arg Asn Pro Thr Gln Asp
    770                 775                 780

Arg Ile Leu Glu Met Lys Val Met Glu Phe Phe Met Lys Val Tyr Gly
785                 790                 795                 800

Tyr Arg Gly Glu His Leu Gly Gly Ser Arg Lys Pro Asp Gly Ala Ile
            805                 810                 815
```

```
Tyr Thr Val Gly Ser Pro Ile Asp Tyr Val Ile Val Asp Thr Lys
            820                 825                 830

Ala Tyr Ser Gly Gly Tyr Asn Leu Pro Ile Gly Gln Ala Asp Glu Met
        835                 840                 845

Gln Arg Tyr Val Lys Glu Asn Gln Thr Arg Asn Lys His Ile Asn Pro
850                 855                 860

Asn Glu Trp Trp Lys Val Tyr Pro Ser Ser Val Thr Glu Phe Lys Phe
865                 870                 875                 880

Leu Phe Val Ser Gly His Phe Lys Gly Asn Tyr Lys Ala Gln Leu Thr
                885                 890                 895

Arg Leu Asn Arg Lys Thr Asn Cys Asn Gly Ala Val Leu Ser Val Glu
            900                 905                 910

Glu Leu Leu Ile Gly Gly Glu Met Ile Lys Ala Gly Thr Leu Thr Leu
            915                 920                 925

Glu Glu Val Arg Arg Lys Phe Asn Asn Gly Glu Ile Asn Phe
        930                 935                 940

<210> SEQ ID NO 15
<211> LENGTH: 942
<212> TYPE: PRT
<213> ORGANISM: Artificial Sequence
<220> FEATURE:
<223> OTHER INFORMATION: Synthetic

<400> SEQUENCE: 15

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
130                 135                 140

Asn Ala Leu Thr Gly Ala Pro Leu Asn Leu Thr Pro Asp Gln Val Val
145                 150                 155                 160

Ala Ile Ala Ser Asn Asn Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser Asn Asn Gly Gly Lys Gln Ala Leu Glu Thr
        195                 200                 205

Val Gln Arg Leu Leu Pro Val Leu Cys Gln Asp His Gly Leu Thr Pro
    210                 215                 220

Asp Gln Val Val Ala Ile Ala Ser Asn Ile Gly Gly Lys Gln Ala Leu
225                 230                 235                 240
```

```
Glu Thr Val Gln Arg Leu Leu Pro Val Leu Cys Gln Asp His Gly Leu
            245                 250                 255

Thr Pro Asp Gln Val Val Ala Ile Ala Ser Asn Ile Gly Gly Lys Gln
        260                 265                 270

Ala Leu Glu Thr Val Gln Arg Leu Leu Pro Val Leu Cys Gln Asp His
            275                 280                 285

Gly Leu Thr Pro Asp Gln Val Val Ala Ile Ala Ser Asn Gly Gly Gly
        290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser Asn Gly
                325                 330                 335

Gly Gly Lys Gln Ala Leu Glu Thr Val Gln Arg Leu Leu Pro Val Leu
            340                 345                 350

Cys Gln Asp His Gly Leu Thr Pro Asp Gln Val Val Ala Ile Ala Ser
            355                 360                 365

Asn Gly Gly Gly Lys Gln Ala Leu Glu Thr Val Gln Arg Leu Leu Pro
        370                 375                 380

Val Leu Cys Gln Asp His Gly Leu Thr Pro Asp Gln Val Val Ala Ile
385                 390                 395                 400

Ala Ser Asn Asn Gly Gly Lys Gln Ala Leu Glu Thr Val Gln Arg Leu
                405                 410                 415

Leu Pro Val Leu Cys Gln Asp His Gly Leu Thr Pro Asp Gln Val Val
            420                 425                 430

Ala Ile Ala Ser Asn Ile Gly Gly Lys Gln Ala Leu Glu Thr Val Gln
            435                 440                 445

Arg Leu Leu Pro Val Leu Cys Gln Asp His Gly Leu Thr Pro Asp Gln
        450                 455                 460

Val Val Ala Ile Ala Ser Asn Ile Gly Gly Lys Gln Ala Leu Glu Thr
465                 470                 475                 480

Val Gln Arg Leu Leu Pro Val Leu Cys Gln Asp His Gly Leu Thr Pro
                485                 490                 495

Asp Gln Val Val Ala Ile Ala Ser Asn Ile Gly Gly Lys Gln Ala Leu
            500                 505                 510

Glu Thr Val Gln Arg Leu Leu Pro Val Leu Cys Gln Asp His Gly Leu
            515                 520                 525

Thr Pro Asp Gln Val Val Ala Ile Ala Ser Asn Gly Gly Gly Lys Gln
        530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Ile Gly Gly
                565                 570                 575

Lys Gln Ala Leu Glu Thr Val Gln Arg Leu Leu Pro Val Leu Cys Gln
            580                 585                 590

Asp His Gly Leu Thr Pro Asp Gln Val Val Ala Ile Ala Ser Asn Gly
            595                 600                 605

Gly Gly Lys Gln Ala Leu Glu Thr Val Gln Arg Leu Leu Pro Val Leu
        610                 615                 620

Cys Gln Asp His Gly Leu Thr Pro Asp Gln Val Val Ala Ile Ala Ser
625                 630                 635                 640

His Asp Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
```

```
                    660                 665                 670
Ala Ser His Asp Gly Gly Lys Gln Ala Leu Glu Ser Ile Val Ala Gln
                675                 680                 685

Leu Ser Arg Pro Asp Pro Ala Leu Ala Ala Leu Thr Asn Asp His Leu
            690                 695                 700

Val Ala Leu Ala Cys Leu Gly Gly Arg Pro Ala Met Asp Ala Val Lys
705                 710                 715                 720

Lys Gly Leu Pro His Ala Pro Glu Leu Ile Arg Arg Val Asn Arg Arg
                725                 730                 735

Ile Gly Glu Arg Thr Ser His Arg Val Ala Gln Leu Val Lys Ser Glu
            740                 745                 750

Leu Glu Glu Lys Lys Ser Glu Leu Arg His Lys Leu Lys Tyr Val Pro
        755                 760                 765

His Glu Tyr Ile Glu Leu Ile Glu Ile Ala Arg Asn Pro Thr Gln Asp
    770                 775                 780

Arg Ile Leu Glu Met Lys Val Met Glu Phe Phe Met Lys Val Tyr Gly
785                 790                 795                 800

Tyr Arg Gly Glu His Leu Gly Gly Ser Arg Lys Pro Asp Gly Ala Ile
                805                 810                 815

Tyr Thr Val Gly Ser Pro Ile Asp Tyr Gly Val Ile Val Asp Thr Lys
            820                 825                 830

Ala Tyr Ser Gly Gly Tyr Asn Leu Pro Ile Gly Gln Ala Asp Glu Met
        835                 840                 845

Glu Arg Tyr Val Glu Glu Asn Gln Thr Arg Asp Lys His Leu Asn Pro
    850                 855                 860

Asn Glu Trp Trp Lys Val Tyr Pro Ser Ser Val Thr Glu Phe Lys Phe
865                 870                 875                 880

Leu Phe Val Ser Gly His Phe Lys Gly Asn Tyr Lys Ala Gln Leu Thr
                885                 890                 895

Arg Leu Asn His Ile Thr Asn Cys Asn Gly Ala Val Leu Ser Val Glu
            900                 905                 910

Glu Leu Leu Ile Gly Gly Glu Met Ile Lys Ala Gly Thr Leu Thr Leu
        915                 920                 925

Glu Glu Val Arg Arg Lys Phe Asn Asn Gly Glu Ile Asn Phe
    930                 935                 940

<210> SEQ ID NO 16
<211> LENGTH: 49
<212> TYPE: DNA
<213> ORGANISM: Homo sapiens

<400> SEQUENCE: 16
tttagctcct actcagactg ttactctggt gacacaacct gtggttact                49

<210> SEQ ID NO 17
<211> LENGTH: 53
<212> TYPE: DNA
<213> ORGANISM: Homo sapiens

<400> SEQUENCE: 17
tttagctcct actcagactg ttactctggt gacacaacct gtggttacta agg           53

<210> SEQ ID NO 18
<211> LENGTH: 46
<212> TYPE: DNA
<213> ORGANISM: Homo sapiens
```

-continued

<400> SEQUENCE: 18
agctcctact cagactgtta ctctggtgac acaacctgtg gttact                          46

<210> SEQ ID NO 19
<211> LENGTH: 50
<212> TYPE: DNA
<213> ORGANISM: Homo sapiens

<400> SEQUENCE: 19
agctcctact cagactgtta ctctggtgac acaacctgtg gttactaagg                      50

<210> SEQ ID NO 20
<211> LENGTH: 50
<212> TYPE: DNA
<213> ORGANISM: Homo sapiens

<400> SEQUENCE: 20
gcaaaaaccc aaaatatttt agctcctact cagactgtta ctctggtgac                      50

<210> SEQ ID NO 21
<211> LENGTH: 52
<212> TYPE: DNA
<213> ORGANISM: Homo sapiens

<400> SEQUENCE: 21
ttgcaaaaac ccaaaatatt ttagctccta ctcagactgt tactctggtg ac                   52

<210> SEQ ID NO 22
<211> LENGTH: 55
<212> TYPE: DNA
<213> ORGANISM: Homo sapiens

<400> SEQUENCE: 22 ccttttttgca aaaacccaaa atattttagc tcctactcag actgttactc tggtg              55

<210> SEQ ID NO 23
<211> LENGTH: 56
<212> TYPE: DNA
<213> ORGANISM: Homo sapiens

<400> SEQUENCE: 23
ccaaactaga aatgccatct tccttgatgt tggaggtacc tgctctggca gatttc              56

<210> SEQ ID NO 24
<211> LENGTH: 51
<212> TYPE: DNA
<213> ORGANISM: Homo sapiens

<400> SEQUENCE: 24
ctatagatga gattatctgc ccatgactgg cgcagggatg gccgcattgc t                    51

<210> SEQ ID NO 25
<211> LENGTH: 48
<212> TYPE: DNA
<213> ORGANISM: Homo sapiens

<400> SEQUENCE: 25
tggaatttga aatatccggg ggcctctaca gaatcctggc atcagtta                        48

<210> SEQ ID NO 26
<211> LENGTH: 15
<212> TYPE: DNA
<213> ORGANISM: Homo sapiens

```
<400> SEQUENCE: 26
attttagctc ctact                                                    15

<210> SEQ ID NO 27
<211> LENGTH: 17
<212> TYPE: DNA
<213> ORGANISM: Homo sapiens

<400> SEQUENCE: 27
tttagctcct actcaga                                                  17

<210> SEQ ID NO 28
<211> LENGTH: 16
<212> TYPE: DNA
<213> ORGANISM: Homo sapiens

<400> SEQUENCE: 28
agctcctact cagact                                                   16

<210> SEQ ID NO 29
<211> LENGTH: 15
<212> TYPE: DNA
<213> ORGANISM: Homo sapiens

<400> SEQUENCE: 29
cctactcaga ctgtt                                                    15

<210> SEQ ID NO 30
<211> LENGTH: 17
<212> TYPE: DNA
<213> ORGANISM: Homo sapiens

<400> SEQUENCE: 30
aaccacaggt tgtgtca                                                  17

<210> SEQ ID NO 31
<211> LENGTH: 16
<212> TYPE: DNA
<213> ORGANISM: Homo sapiens

<400> SEQUENCE: 31
agtaaccaca ggttgt                                                   16

<210> SEQ ID NO 32
<211> LENGTH: 17
<212> TYPE: DNA
<213> ORGANISM: Homo sapiens

<400> SEQUENCE: 32
ccttagtaac cacaggt                                                  17

<210> SEQ ID NO 33
<211> LENGTH: 17
<212> TYPE: DNA
<213> ORGANISM: Homo sapiens

<400> SEQUENCE: 33
gcaaaaaccc aaaatat                                                  17

<210> SEQ ID NO 34
<211> LENGTH: 17
<212> TYPE: DNA
```

<213> ORGANISM: Homo sapiens

<400> SEQUENCE: 34
ttgcaaaaac ccaaaat                                                    17

<210> SEQ ID NO 35
<211> LENGTH: 17
<212> TYPE: DNA
<213> ORGANISM: Homo sapiens

<400> SEQUENCE: 35
cctttttgca aaaccc                                                     17

<210> SEQ ID NO 36
<211> LENGTH: 17
<212> TYPE: DNA
<213> ORGANISM: Homo sapiens

<400> SEQUENCE: 36
caccagagta acagtct                                                    17

<210> SEQ ID NO 37
<211> LENGTH: 19
<212> TYPE: DNA
<213> ORGANISM: Homo sapiens

<400> SEQUENCE: 37
gtcaccagag taacagtct                                                  19

<210> SEQ ID NO 38
<211> LENGTH: 18
<212> TYPE: DNA
<213> ORGANISM: Homo sapiens

<400> SEQUENCE: 38
ccaaactaga aatgccat                                                   18

<210> SEQ ID NO 39
<211> LENGTH: 19
<212> TYPE: DNA
<213> ORGANISM: Homo sapiens

<400> SEQUENCE: 39
gaaatctgcc agagcaggt                                                  19

<210> SEQ ID NO 40
<211> LENGTH: 18
<212> TYPE: DNA
<213> ORGANISM: Homo sapiens

<400> SEQUENCE: 40
ctatagatga gattatct                                                   18

<210> SEQ ID NO 41
<211> LENGTH: 18
<212> TYPE: DNA
<213> ORGANISM: Homo sapiens

<400> SEQUENCE: 41
agcaatgcgg ccatccct                                                   18

<210> SEQ ID NO 42
<211> LENGTH: 17

-continued

```
<212> TYPE: DNA
<213> ORGANISM: Homo sapiens

<400> SEQUENCE: 42
taactgatgc caggatt                                              17

<210> SEQ ID NO 43
<211> LENGTH: 17
<212> TYPE: DNA
<213> ORGANISM: Homo sapiens

<400> SEQUENCE: 43
tggaatttga aatatcc                                              17

<210> SEQ ID NO 44
<211> LENGTH: 48
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(31)
<223> OTHER INFORMATION: n is a, c, g, or t

<400> SEQUENCE: 44
tggaatttga aatatccnnn nnnnnnnnnn naatcctggc atcagtta             48

<210> SEQ ID NO 45
<211> LENGTH: 48
<212> TYPE: DNA
<213> ORGANISM: Mus musculus

<400> SEQUENCE: 45
tggaatttga aatatccaga ggcctctaca gaatcctggc atcagtta             48

<210> SEQ ID NO 46
<211> LENGTH: 55
<212> TYPE: DNA
<213> ORGANISM: Homo sapiens

<400> SEQUENCE: 46
tattttagct cctactcaga ctgttactct ggtgacacaa cctgtggtta ctaag     55

<210> SEQ ID NO 47
<211> LENGTH: 8
<212> TYPE: PRT
<213> ORGANISM: Homo sapiens

<400> SEQUENCE: 47

Leu Leu Leu Arg Leu Leu Leu Trp
1               5

<210> SEQ ID NO 48
<211> LENGTH: 14
<212> TYPE: PRT
<213> ORGANISM: Homo sapiens

<400> SEQUENCE: 48

Ser Tyr Ser Asp Cys Tyr Ser Gly Asp Thr Thr Cys Gly Tyr
1               5                   10

<210> SEQ ID NO 49
<211> LENGTH: 15
<212> TYPE: PRT
```

-continued

<213> ORGANISM: Homo sapiens

<400> SEQUENCE: 49

Pro Thr Gln Thr Val Thr Leu Val Thr Gln Pro Val Val Thr Lys
1               5                   10                  15

<210> SEQ ID NO 50
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (27)..(27)
<223> OTHER INFORMATION: n is a, c, g, or t

<400> SEQUENCE: 50
tattttagct cctactcaga ctgttanctc tggtgacaca acctgtggtt actaag         56

<210> SEQ ID NO 51
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 51

Leu Leu Leu Arg Leu Leu Xaa Leu Val Thr Gln Pro Val Val Thr Lys
1               5                   10                  15

<210> SEQ ID NO 52
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (27)..(28)
<223> OTHER INFORMATION: n is a, c, g, or t

<400> SEQUENCE: 52
tattttagct cctactcaga ctgttannct ctggtgacac aacctgtggt tactaag        57

<210> SEQ ID NO 53
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: Xaa can be any naturally occurring amino acid

<400> SEQUENCE: 53

Ser Tyr Ser Asp Cys Xaa Xaa Leu Val Thr Gln Pro Val Val Thr Lys
1               5                   10                  15

<210> SEQ ID NO 54
<211> LENGTH: 15
<212> TYPE: DNA
<213> ORGANISM: Homo sapiens

```
<400> SEQUENCE: 54
attttagctc ctact                                                    15

<210> SEQ ID NO 55
<211> LENGTH: 17
<212> TYPE: DNA
<213> ORGANISM: Homo sapiens

<400> SEQUENCE: 55
tttagctcct actcaga                                                  17

<210> SEQ ID NO 56
<211> LENGTH: 16
<212> TYPE: DNA
<213> ORGANISM: Homo sapiens

<400> SEQUENCE: 56
agctcctact cagact                                                   16

<210> SEQ ID NO 57
<211> LENGTH: 15
<212> TYPE: DNA
<213> ORGANISM: Homo sapiens

<400> SEQUENCE: 57
cctactcaga ctgtt                                                    15

<210> SEQ ID NO 58
<211> LENGTH: 61
<212> TYPE: DNA
<213> ORGANISM: Homo sapiens

<400> SEQUENCE: 58
aaaatatttt agctcctact cagactgtta ctctggtgac acaacctgtg gttactaagg   60
a                                                                   61

<210> SEQ ID NO 59
<211> LENGTH: 61
<212> TYPE: DNA
<213> ORGANISM: Homo sapiens

<400> SEQUENCE: 59
tccttagtaa ccacaggttg tgtcaccaga gtaacagtct gagtaggagc taaaatattt   60
t                                                                   61

<210> SEQ ID NO 60
<211> LENGTH: 25
<212> TYPE: DNA
<213> ORGANISM: Artificial Sequence
<220> FEATURE:
<223> OTHER INFORMATION: Synthetic

<400> SEQUENCE: 60
gagtttggct caaattgtta ctctt                                         25

<210> SEQ ID NO 61
<211> LENGTH: 25
<212> TYPE: DNA
<213> ORGANISM: Artificial Sequence
<220> FEATURE:
<223> OTHER INFORMATION: Synthetic

<400> SEQUENCE: 61
```
gggaaatggt ctaggagagt aaagt                                           25

<210> SEQ ID NO 62
<211> LENGTH: 34
<212> TYPE: DNA
<213> ORGANISM: Artificial Sequence
<220> FEATURE:
<223> OTHER INFORMATION: Synthetic

<400> SEQUENCE: 62
agactgttac tcttggtgac acaacctgtg ttac                                 34

<210> SEQ ID NO 63
<211> LENGTH: 59
<212> TYPE: DNA
<213> ORGANISM: Homo sapiens

<400> SEQUENCE: 63
aaaaacccaa aatatttag ctcctactca gactgttact ctggtgacac aacctgtgg       59

<210> SEQ ID NO 64
<211> LENGTH: 56
<212> TYPE: DNA
<213> ORGANISM: Artificial Sequence
<220> FEATURE:
<223> OTHER INFORMATION: Synthetic

<400> SEQUENCE: 64
aaaaacccaa aatatttag ctcctactca gactgttact gtgacacaac ctgtgg          56

<210> SEQ ID NO 65
<211> LENGTH: 38
<212> TYPE: DNA
<213> ORGANISM: Artificial Sequence
<220> FEATURE:
<223> OTHER INFORMATION: Synthetic

<400> SEQUENCE: 65
aaaaacccaa aatatttag ctcctactca gactgtgg                              38

<210> SEQ ID NO 66
<211> LENGTH: 57
<212> TYPE: DNA
<213> ORGANISM: Artificial Sequence
<220> FEATURE:
<223> OTHER INFORMATION: Synthetic

<400> SEQUENCE: 66
aaaaacccaa aatatttag ctcctactca gactgttact cttgacacaa cctgtgg         57

<210> SEQ ID NO 67
<211> LENGTH: 49
<212> TYPE: DNA
<213> ORGANISM: Artificial Sequence
<220> FEATURE:
<223> OTHER INFORMATION: Synthetic

<400> SEQUENCE: 67
aaaacccaaa atattttagc tcctactcag actgttacac aacctgtgg                 49

<210> SEQ ID NO 68
<211> LENGTH: 57
<212> TYPE: DNA
<213> ORGANISM: Artificial Sequence
<220> FEATURE:

<223> OTHER INFORMATION: Synthetic

<400> SEQUENCE: 68
aaaaacccaa aatattttag ctcctactca gactgttact ggtgacacaa cctgtgg    57

<210> SEQ ID NO 69
<211> LENGTH: 241
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (42)..(224)
<223> OTHER INFORMATION: n is a, c, g, or t

<400> SEQUENCE: 69
aaaaacccaa aatattttag ctcctactca gactgttact cnnnnnnnnn nnnnnnnnnn    60
nnnnnnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn nnnnnnnnnn nnnnnnnnnn nnnnggtgac acaacctgtg   240
g                                                                   241

<210> SEQ ID NO 70
<211> LENGTH: 57
<212> TYPE: DNA
<213> ORGANISM: Artificial Sequence
<220> FEATURE:
<223> OTHER INFORMATION: Synthetic

<400> SEQUENCE: 70
aaaaccccaa aattttttag ctccttctca gacttttttct ggtgacacaa cctgtgg    57

<210> SEQ ID NO 71
<211> LENGTH: 60
<212> TYPE: DNA
<213> ORGANISM: Artificial Sequence
<220> FEATURE:
<223> OTHER INFORMATION: Synthetic

<400> SEQUENCE: 71
aaaaacccaa aatattttag ctcctactca gactgttact cttggtgaca caacctgtgg    60

<210> SEQ ID NO 72
<211> LENGTH: 53
<212> TYPE: DNA
<213> ORGANISM: Artificial Sequence
<220> FEATURE:
<223> OTHER INFORMATION: Synthetic

<400> SEQUENCE: 72
aaaaacccaa aatattttag ctcctactca gactgttact ctgcaacctg tgg    53

<210> SEQ ID NO 73
<211> LENGTH: 56
<212> TYPE: DNA
<213> ORGANISM: Artificial Sequence
<220> FEATURE:
<223> OTHER INFORMATION: Synthetic

<400> SEQUENCE: 73
aaaaacccaa aatattttag ctcctactca gactgttacg gtgacacaac ctgtgg    56

```
<210> SEQ ID NO 74
<211> LENGTH: 59
<212> TYPE: DNA
<213> ORGANISM: Artificial Sequence
<220> FEATURE:
<223> OTHER INFORMATION: Synthetic

<400> SEQUENCE: 74
aaaaacccaa aatattttag ctcctactca gactgttact ctggtgacac aacctgtgg      59

<210> SEQ ID NO 75
<211> LENGTH: 34
<212> TYPE: DNA
<213> ORGANISM: Homo sapiens

<400> SEQUENCE: 75
agactgttac tctggtgaca caacctgtgg ttac                                 34

<210> SEQ ID NO 76
<211> LENGTH: 30
<212> TYPE: DNA
<213> ORGANISM: Artificial Sequence
<220> FEATURE:
<223> OTHER INFORMATION: Synthetic

<400> SEQUENCE: 76
agactgtttg gtgacacaac ctgtggttac                                      30

<210> SEQ ID NO 77
<211> LENGTH: 33
<212> TYPE: DNA
<213> ORGANISM: Artificial Sequence
<220> FEATURE:
<223> OTHER INFORMATION: Synthetic

<400> SEQUENCE: 77
agactgttac tctgtgacac aacctgtggt tac                                  33

<210> SEQ ID NO 78
<211> LENGTH: 25
<212> TYPE: DNA
<213> ORGANISM: Artificial Sequence
<220> FEATURE:
<223> OTHER INFORMATION: Synthetic

<400> SEQUENCE: 78
agactgtgac acaacctgtg gttac                                           25

<210> SEQ ID NO 79
<211> LENGTH: 29
<212> TYPE: DNA
<213> ORGANISM: Artificial Sequence
<220> FEATURE:
<223> OTHER INFORMATION: Synthetic

<400> SEQUENCE: 79
agactgttac tgacacaacc tgtggttac                                       29

<210> SEQ ID NO 80
<211> LENGTH: 31
<212> TYPE: DNA
<213> ORGANISM: Artificial Sequence
<220> FEATURE:
<223> OTHER INFORMATION: Synthetic

<400> SEQUENCE: 80
```
agactgttac tctgacacaa cctgtggtta c          31

<210> SEQ ID NO 81
<211> LENGTH: 31
<212> TYPE: DNA
<213> ORGANISM: Artificial Sequence
<220> FEATURE:
<223> OTHER INFORMATION: Synthetic

<400> SEQUENCE: 81
agactgttac tgtgacacaa cctgtggtta c          31

<210> SEQ ID NO 82
<211> LENGTH: 31
<212> TYPE: DNA
<213> ORGANISM: Artificial Sequence
<220> FEATURE:
<223> OTHER INFORMATION: Synthetic

<400> SEQUENCE: 82
agactgttac tctgacacaa cctgtggtta c          31

<210> SEQ ID NO 83
<211> LENGTH: 34
<212> TYPE: DNA
<213> ORGANISM: Homo sapiens

<400> SEQUENCE: 83
agactgttac tctggtgaca caacctgtgg ttac          34

<210> SEQ ID NO 84
<211> LENGTH: 31
<212> TYPE: DNA
<213> ORGANISM: Artificial Sequence
<220> FEATURE:
<223> OTHER INFORMATION: Synthetic

<400> SEQUENCE: 84
agactgttac tgtgacacaa cctgtggtta c          31

<210> SEQ ID NO 85
<211> LENGTH: 13
<212> TYPE: DNA
<213> ORGANISM: Artificial Sequence
<220> FEATURE:
<223> OTHER INFORMATION: Synthetic

<400> SEQUENCE: 85
agactgtggt tac          13

<210> SEQ ID NO 86
<211> LENGTH: 32
<212> TYPE: DNA
<213> ORGANISM: Artificial Sequence
<220> FEATURE:
<223> OTHER INFORMATION: Synthetic

<400> SEQUENCE: 86
agactgttac tcttgacaca acctgtggtt ac          32

<210> SEQ ID NO 87
<211> LENGTH: 25
<212> TYPE: DNA
<213> ORGANISM: Artificial Sequence
<220> FEATURE:
<223> OTHER INFORMATION: Synthetic

<400> SEQUENCE: 87
agactgttac acaacctgtg gttac                                              25

<210> SEQ ID NO 88
<211> LENGTH: 32
<212> TYPE: DNA
<213> ORGANISM: Artificial Sequence
<220> FEATURE:
<223> OTHER INFORMATION: Synthetic

<400> SEQUENCE: 88
agactgttac tggtgacaca acctgtggtt ac                                      32

<210> SEQ ID NO 89
<211> LENGTH: 216
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(195)
<223> OTHER INFORMATION: n is a, c, g, or t

<400> SEQUENCE: 89
agactgttac tcnnnnnnnn nnnnnnnnnn nnnnnnnnnn nnnnnnnnnn nnnnnnnnnn         60
nnnnnnnnnn nnnnnnnnnn nnnnnnnnnn nnnnnnnnnn nnnnnnnnnn nnnnnnnnnn        120
nnnnnnnnnn nnnnnnnnnn nnnnnnnnnn nnnnnnnnnn nnnnnnnnnn nnnnnnnnnn        180
nnnnnnnnnn nnnnnggtga cacaacctgt ggttac                                  216

<210> SEQ ID NO 90
<211> LENGTH: 32
<212> TYPE: DNA
<213> ORGANISM: Artificial Sequence
<220> FEATURE:
<223> OTHER INFORMATION: Synthetic

<400> SEQUENCE: 90
agactgttac tggtgacaca acctgtggtt ac                                      32

<210> SEQ ID NO 91
<211> LENGTH: 28
<212> TYPE: DNA
<213> ORGANISM: Artificial Sequence
<220> FEATURE:
<223> OTHER INFORMATION: Synthetic

<400> SEQUENCE: 91
agactgttac tctgcaacct gtggttac                                           28

<210> SEQ ID NO 92
<211> LENGTH: 31
<212> TYPE: DNA
<213> ORGANISM: Artificial Sequence
<220> FEATURE:
<223> OTHER INFORMATION: Synthetic

<400> SEQUENCE: 92
agactgttac ggtgacacaa cctgtggtta c                                       31

<210> SEQ ID NO 93
<211> LENGTH: 33
<212> TYPE: DNA

```
<213> ORGANISM: Homo sapiens

<400> SEQUENCE: 93
agactgttac tctggtgaca caacctgtgt tac                                    33
```

GENETIC CORRECTION OF MUTATED GENES

CROSS REFERENCE TO RELATED APPLICATION

This application is a divisional of U.S. patent application Ser. No. 14/397,420, filed Oct. 27, 2014, which is a national phase filing under 35 U.S.C. § 371 of International Application No. PCT/US2013/038536, filed Apr. 26, 2013, which claims priority to U.S. Provisional Application No. 61/639,227, filed Apr. 27, 2012, which are incorporated herein by reference in their entirety.

STATEMENT OF GOVERNMENT INTEREST

This invention was made with government support under federal grant number DP2-OD008586 awarded by NIH. The U.S. Government has certain rights to this invention.

SEQUENCE LISTING

The sequence listing is filed with the application in electronic format only and is incorporated by reference herein. The sequence listing text file "WO00_ASFILED_SequenceListing-Text" was created on Apr. 26, 2013 and is 141,796 bytes in size.

TECHNICAL FIELD

The present disclosure relates to the field of genome engineering and genomic alteration of the mutated gene using transcription activator-like effector nucleases (TALENs).

BACKGROUND

Hereditary genetic diseases have devastating effects on children in the United States. These diseases currently have no cure and can only be managed by attempts to alleviate the symptoms. For decades, the field of gene therapy has promised a cure to these diseases, such as Duchenne muscular dystrophy (DMD), by introducing new genetic material into patient's cells. In contrast to gene addition, genome editing with engineered site-specific endonucleases selectively replace or correct disrupted genes. Technical hurdles regarding the safe and efficient delivery of therapeutic genes to cells and patients have limited these approaches. Scientists have only been able to add new genetic material to cells without any control over where it is inserted into the genome. This strategy has let to a myriad of unforeseen negative consequences that can all be attributed to the inability to correct the existing mutated gene sequences. Current experimental gene therapy strategies for genetic diseases, such as DMD, use repeated administration of transient gene delivery vehicles or rely on permanent integration of foreign genetic material into the genomic DNA. Both of these methods have serious safety concerns. Furthermore, these strategies have been limited by an inability to deliver the large and complex gene sequences.

SUMMARY

The present disclosure is directed to a transcription activator-like effector nuclease (TALEN) protein that may bind to a dystrophin gene. The dystrophin gene may comprise a premature stop codon and the TALEN protein may bind upstream or downstream from the premature stop codon. The TALEN protein may bind to a nucleotide sequence comprising one of SEQ ID NOs: 16-46, 50, 52, 58, and 59, and the complement thereof. The TALEN protein may comprise a nuclease. The nuclease may comprise FokI. The TALEN protein may comprise 15-19 repeat variable diresidue (RVD) modules. The TALEN protein may comprise an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 15. The TALEN protein may bind to a region in exon 51 of the dystrophin gene. The TALEN protein may bind to a nucleotide sequence comprising one of SEQ ID NOs: 16-24, 26-41, 46, 50, 52, 58, and 59, and the complement thereof. The TALEN protein may comprise a nuclease. The nuclease may comprise FokI. The TALEN protein may comprise 15-19 RVD modules. The TALEN protein may comprise an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13. The TALEN protein may bind to a nucleotide sequence comprising SEQ ID NO: 19, or the complement thereof. The TALEN protein may comprise an amino acid sequence selected from the group consisting of SEQ ID NOs: 2 and 4. The TALEN protein may bind to a region in the 5' UTR of the dystrophin gene. The TALEN protein may bind to a nucleotide sequence comprising one of SEQ ID NOs: 25 and 42-45 and the complement thereof. The TALEN protein may comprise a nuclease. The nuclease may comprise FokI. The TALEN protein may comprise 15-19 RVD modules. The TALEN protein may comprise an amino acid sequence selected from the group consisting of SEQ ID NOs: 14 and 15. The dystrophin gene may be a human dystrophin gene.

The present disclosure is directed to an isolated polynucleotide comprising a nucleotide sequence encoding said TALEN protein and a vector comprising said isolated polynucleotide. The present disclosure is directed to a cell comprising said isolated polynucleotide or said vector.

The present disclosure is directed to a composition comprising two or more of said TALENs, wherein a first TALEN binds to a first binding region and a second TALEN binds to a second binding region, wherein the first binding region and second binding region are located within a target region and the first binding region and second binding region are not the same. The first binding region and the second binding region may be separated by at least one nucleotide. The first binding region and the second binding region may be separated by 5-25 base pairs.

The present disclosure is directed to a method of treating a subject in need thereof having a mutant dystrophin gene, the method comprising administering to the subject said TALEN protein, said isolated polynucleotide, said vector, said cell or said composition. The subject may be suffering from Duchenne muscular dystrophy.

The present disclosure is directed to a method of correcting a mutant dystrophin gene in a cell, the method comprising administering to a cell containing a mutant dystrophin gene said TALEN protein, said isolated polynucleotide, said vector, or said composition. The correction of the mutant dystrophin gene may comprise homology-directed repair. The method may further comprise administering to the cell a donor DNA. The mutant dystrophin gene may comprise a frameshift mutation which causes a premature stop codon and a truncated gene product. The correction of the mutant dystrophin gene may comprise nuclease mediated non-homologous end joining.

The present disclosure is directed to a method of correcting a mutant gene in a cell, the method comprising administering to a cell containing a mutant gene a first TALEN and a second TALEN, wherein the first TALEN binds to a first binding region and a second TALEN binds to a second binding region, wherein the first binding region and second binding region are located within a target region and the first binding region and second binding region are not the same, wherein the correction of the mutant dystrophin gene may comprise nuclease mediated non-homologous end joining, and wherein the correction restores the mutant gene.

The present disclosure is directed to a method of correcting a mutant dystrophin gene in a cell, the method comprising administering to a cell containing a mutant dystrophin gene a first TALEN and a second TALEN, wherein the first TALEN binds to a first binding region and a second TALEN binds to a second binding region, wherein the first binding region and second binding region are located within a target region and the first binding region and second binding region are not the same. The mutant dystrophin gene may comprise a premature stop codon and the target region is upstream or downstream of the premature stop codon. The correction of the mutant dystrophin gene may comprise nuclease mediated non-homologous end joining. The first binding region a the second binding region may be separated by at least one nucleotide. The first binding region and the second binding region may be separated by 5-25 base pairs. The method may not involve co-administration of exogenous DNA. The correction of the mutant dystrophin gene may comprise homology-directed repair. The method may further comprise administering to the cell a donor DNA.

The present disclosure is directed to a kit comprising said TALEN protein, said isolated polynucleotide, said vector, said cell or said composition.

The present disclosure is directed to a kit for correcting a mutant dystrophin gene, the kit comprising said TALEN protein, said isolated polynucleotide, said vector, said cell or said composition.

BRIEF DESCRIPTION OF THE DRAWINGS

FIG. 2 shows the full amino acid sequences of engineered TALENs targeted to exon 51 of the dystrophin gene. Fok ELD-S/KKR-S refers to the FokI nuclease domain that was fused to the TALEN DNA-binding domains. The RVD sequence are underlined.

FIG. 8 shows chromatograms of clones from FIG. 7.

FIG. 11 shows TALENs targeting the 5' UTR of the mouse and human dystrophin gene for integrating a gene, such as the dystrophin or miniaturized dystrophin cDNA, under the control of the dystrophin promoter. (A) The target site of TN45/50 in the human and mouse dystrophin 5' UTR. (B) The RVD components of TN45/50. (C) Combinations of TALENs were co-transfected into HEK293T cells to screen for highly active TALEN pans. Gene modification frequency was monitored at day 3 and day 10 to assess stable gene modification. (D) 10 micrograms each plasmid encoding each TN45 and TN50 were electroporated into human skeletal myoblasts from a DMD patients. TALEN-mediated modification of the target locus was determined by the Surveyor assay three days after transaction.

FIG. 12 shows the full amino acid sequences of engineered TALENs targeted to the 5'UTR of the dystrophin gene. Fok ELDS/KKRS refers to the FokI nuclease domain that was fused to the TALE DNA-binding domains.

DETAILED DESCRIPTION

Figure 1:
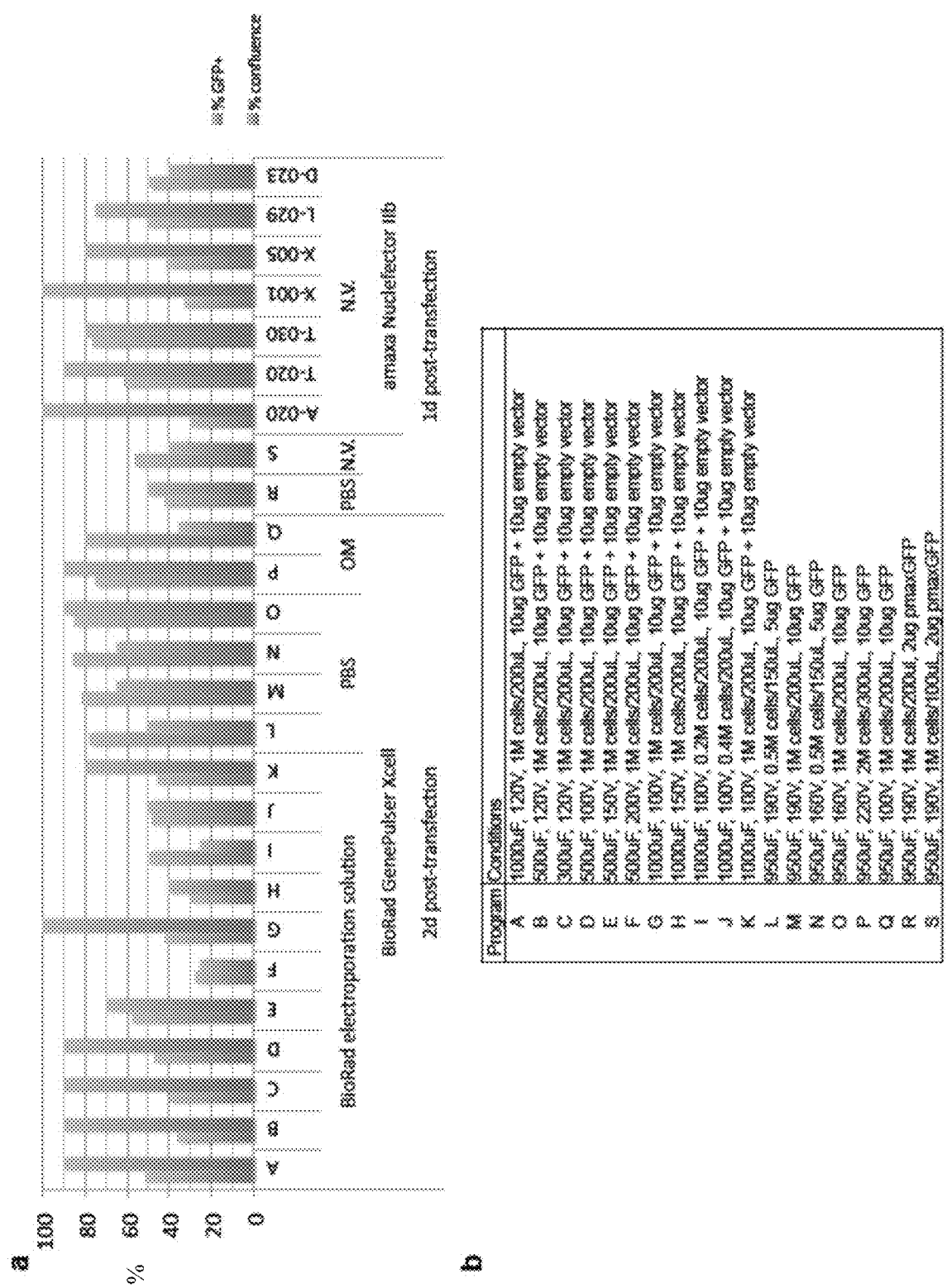
FIG. 1 shows the optimization of electroporation conditions for myoblasts, (a) DMD myoblast cells (cell line 1) were electroporated using BioRad Gene Pulser Xcell or Amaxa Nucleofector IIb devices using the indicated programs. Several different buffers were tested, including BioRad electroporation solution, Sigma phosphate-buffered saline product # D8537 (PBS), Invitrogen OptiMEM I (OM), or Amaxa Nucleofector solution V (N.V.). Conditions using the GenePulser device used infinite resistance. For nucleofection, 1 million cells/100 µL nucleofection solution and 2 µg of GFP vector were used according to the manufacturer's specifications. Electroporation using the GenePulser device with program O in PBS solution was selected as the optimal conditions for electroporsting myoblasts. (b) Conditions used to optimize BioRad Gene Pulser Xcell electroporation.

As described herein, certain methods and engineered transcription activator-like effector nuclease (TALEN)-related compositions been discovered to be useful for correcting or reducing the effects of mutations in genes involved in genetic diseases, for example, the dystrophin gene for phenotypic correction of DMD. The present disclosure is directed to genome editing with TALENs with a repair template or donor DNA, which can replace the entire gene or the region containing the mutation and restore the expression of a full-functional or partially-functional protein. The present disclosure is also directed to genome editing with TALENs without a repair template, which can efficiently correct the reading frame and restore the expression of a functional protein involved in a genetic disease. The disclosed TALENs and methods may involve using nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active TALENs with an efficient gene editing method for the treatment of genetic diseases caused by mutations in nonessential coding regions that cause frameshifts or premature stop codons, with no TALEN-mediated off-target changes to the protein-coding regions of the genome.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Binding region" as used herein refers to the region within the target region that is recognized and bound by a TALEN. The TALE DNA-binding domain of the TALEN recognizes and binds to the binding region. For example, the binding region in the dystrophin gene may include a nucleotide sequence found within a target region of SEQ ID NO: 16-25, 44, or 45, or a complement thereof. The binding region may include a nucleotide sequence of SEQ ID No: 26-43, or a complement thereof.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimize.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Correcting", "genome editing" and "restoring" as used herein refers to changing a mutant gene that encodes a truncated protein or no protein at all, such that a full-length functional or partially full-length functional protein expression is obtained. Correcting or restoring a mutant gene may include replacing the region of the gene that has the mutation or replacing the entire mutant gene with a copy of the gene that does not have the mutation with a repair mechanism such as HDR. Correcting or restoring a mutant gene may also include repairing a frameshift mutation that causes a premature stop codon by generating a double stranded break in the gene that is then repaired using NHEJ. NHEJ may add or delete at least one base pair during repair which may restore the proper reading frame and eliminate the premature stop codon.

"Donor DNA", "donor template" and "repair template" as used interchangeably herein refers to a double-stranded DNA fragment or molecule that includes at least a portion of the gene of interest. The donor DNA may encode a full-functional protein or a partially-functional protein.

"Duchenne Muscular Dystrophy" and "DMD" as used interchangeably herein refers to a recessive, fatal, X-linked disorder that results in muscle degeneration and eventual death. DMD is a common hereditary monogenic disease and occurs in 1 in 3500 males. DMD is the result of inherited or spontaneous mutations that cause nonsense or frame shift mutations in the dystrophin gene. The majority of dystrophin mutations that cause DMD are deletions of exons that disrupt the reading frame and cause premature translation termination in the dystrophin gene. DMD patients typically lose the ability to physically support themselves during childhood, become progressively weaker during the teenage years, and die in their twenties.

"Dystrophin" as used herein refers to a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane that is responsible for regulating muscle cell integrity and function. The dystrophin gene or "DMD gene" as used interchangeably herein is 2.2 megabases at locus Xp21. The primary transcription measures about 2,400 kb with the mature mRNA being about 14 kb. 79 exons code for the protein which is over 3500 amino acids.

"Exon 51" as used herein refers to the $51^{st}$ exon of the dystrophin gene. Exon 51 is frequently adjacent to frame-disruptin deletions in DMD patients and has been targeted in clinical trials for oligonucleotide-based exon skipping. A clinical trial for the exon 51 skipping compound eteplirsen recently reported a significant functional benefit across 48 weeks, with an average of 47% dystrophin positive fibers compared to baseline. Mutations in exon 51 are ideally suited for permanent correction by NHEJ-based genome editing.

"Frameshift" or "frameshift mutation" as used interchangeably herein refers to a type of gene mutation wherein the addition or deletion of one or more nucleotides causes a shift in the reading frame of the codons in the mRNA. The shift in reading frame may lead to the alteration in the amino acid sequence at protein translation, such as a missense mutation or a premature stop codon.

"Functional" and "full-functional" as used herein describes protein that has biological activity. A "functional gene" refers to a gene transcribed to mRNA, which is translated to a functional protein.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genetic disease" as used herein refers to a disease, partially or completely, directly or indirectly, caused by one or more abnormalities in the genome, especially a condition that is present from birth. The abnormality may be a mutation, an insertion or a deletion. The abnormality may affect the coding sequence of the gene or its regulatory sequence. The genetic disease may be, but not limited to DMD, cystic fibrosis, Huntingdon's chorea, familial hypercholesterolemia (LDL receptor defect), hepatoblastoma, Wilson's disease, congenital hepatic porphyria, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, and Tay-Sachs disease.

"Homology-directed repair" or "HDR" as used interchangeably herein refers to a mechanism in cells to repair double strand DNA lesions when a homologous piece of DNA is present in the nucleus, mostly in G2 and S phase of the cell cycle. HDR used a donor DNA template to guide repair and may be used to create specific sequence changes to the genome, including the targeted addition of whole genes. If a donor template is provided along with the TALENs, then the cellular machinery will repair the break by homologous recombination, which is enhanced several orders of magnitude in the presence of DNA cleavage. When the homologous DNA piece is absent, non-homologous end joining may take place instead.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Mutant gene" or "mutated gene" as used interchangeably herein refers to a gene that has undergone a detectable mutation. A mutant gene has undergone a change, such as the loss, gain, or exchange of genetic material, which affects the normal transmission and expression of the gene. A "disrupted gene" as used herein refers to a mutant gene that has a mutation that causes a premature stop codon. The disrupted gene product is truncated relative to a full-length undisrupted gene product.

"Non-homologous end joining (NHEJ) pathway" as used herein refers to a pathway that repairs double-strand breaks in DNA by directly ligating the break ends without the need for a homologous template. The template-independent re-ligation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called micro-homologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible.

"Nuclease mediated NHEJ" as used herein refers to NHEJ that is initiated after a nuclease, such as a TALEN, cuts double stranded DNA.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hyposanthine, isocytosine and isoguanine. Nucleic acids may be obtained by chemical synthesis methods or by recombinant methods.

"Operably linked" used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Partially-functional" as used herein describes a protein that is encoded by a mutant gene and has less biological activity than a functional protein but more than a non-functional protein.

"Premature stop codon" or "out-of-frame stop codon" as used interchangeably herein refers to nonsense mutation in a sequence of DNA, which results in a stop codon at location not normally found in the wild-type gene. A premature stop codon may cause a protein to be truncated or shorter compared to the full-length version of the protein.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Repeat variable diresidue" or "RVD" as used interchangeably herein refers to a pair of adjacent amino acid residues within the DNA recognition motif (also known as "RVD module"), which includes 33-35 amino acids, of the TALE DNA-binding domain. The RVD determines the nucleotide specificity of the RVD module. RVD modules may be combined to produce an RVD array. The "RVD areas length" an used herein refers to the number of RVD modules that corresponds to the length of the nucleotide sequence within the target region that is recognized by the TALEN, i.e., the binding region.

"Spacers" and "spacer region" as used interchangeably herein refers to the region within the target region that is between, but not a part of, the binding regions for two TALENs.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Target gene" as used herein refers to any nucleotide sequence encoding a known or putative gene product. The target gene may be a mutated gene involved in a genetic disease.

"Target region" as used herein refers to the region of the target gene to which two or more TALENs are designed to bind and cleave. The target region includes the binding regions for the TALENS and the spacer regions which occurs between the binding regions. The two TALENs bind to different binding regions within the target region, after which the target region is cleaved. For example, the target region in the dystrophin gene may include a nucleotide sequence of SEQ ID NO: 16-25, 44-46, 50, 52, 58, or 59, or a complement thereof. The target region in the dystrophin gene may include one or more of SEQ ID NO: 26-43, or a complement thereof. Each of SEQ ID NO: 26-43, or a complement thereof, may represent a binding region.

"Transcription activator-like effector" or "TALE" as used herein refers to a protein structure that recognizes and binds to a particular DNA sequence. The "TALE DNA-binding domain" refers to a DNA-binding domain that includes an array of tandem 33-35 amino acid repeats, also known as RVD modules, each of which specifically recognizes a single base pair of DNA. RVD modules may be arranged in any order to assemble an array that recognizes a defined sequence.

A binding specificity of a TALE DNA-binding domain is determined by the RVD array followed by a single truncated repeat of 20 amino acids. A TALE DNA-binding domain may have 12 to 27 RVD modules, each of which contains an RVD and recognizes a single base pair of DNA. Specific RVDs have been identified that recognize each of the four possible DNA nucleotides (A, T, C, and G). Because the TALE DNA-binding domains are modular, repeats that recognize the four different DNA nucleotides may be linked together to recognize any particular DNA sequence. These targeted DNA-binding domains may then be combined with catalytic domains to create functional enzymes, including artificial transcription factors, methyltransferases, integrases, nucleases, and recombinases.

"Transcription activator-like effector nucleases" or "TALENs" as used interchangeably herein refers to engineered fusion proteins of the catalytic domain of a nuclease, such as endonuclease FokI, and a designed TALE DNA-binding domain that may be targeted to a custom DNA sequence. A "TALEN monomer" refers to an engineered fusion protein with a catalytic nuclease domain and a designed TALE DNA-binding domain. Two TALEN monomers may be designed to target and cleave a target region.

TALENs may be used to introduce site-specific double strand breaks at targeted genomic loci. Site-specific double-strand breaks are created when two independent TALENs bind to nearby DNA sequences, thereby permitting dimerization of FokI and cleavage of the target DNA. TALENs have advanced genome editing due to their high rate of successful and efficient genetic modification. This DNA cleavage may stimulate the natural DNA-repair machinery, leading to one of two possible repair pathways: homology-directed repair (HDR) or the non-homologous end joining (NHEJ) pathway. For example, a TALEN directed towards the dystrophin gene may include an amino acid sequence of any one of SEQ ID NO: 1-15.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. For example, the vector may encode a TALEN protein comprising the amino acid sequence of one of SEQ ID NO: 1-15.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. TALENs

Provided herein are TALENs for use in genome editing and treating genetic diseases. The TALENs may be designed to target any gene involved in a genetic disease. The TALENs may include a nuclease and a TALE DNA-binding domain that binds to the target gene. The target gene may have a mutation such as a frameshift mutation or a nonsense mutation. If the target gene has a mutation that causes a premature stop codon, the TALEN may be designed to recognize and bind a nucleotide sequence upstream or downstream from the premature stop codon.

The TALE DNA-binding domain may have an RVD array length between 1-30 modules, between 1-25 modules, between 1-20 modules, between 1-15 modules, between 5-30 modules, between 5-25 modules, between 5-20 modules, between 5-15 modules, between 7-25 modules, between 7-23 modules, between 7-20 modules, between 10-30 modules, between 10-25 modules, between 10-20 modules, between 10-15 modules, between 15-30 modules, between 15-25 modules, between 15-20, between 15-19 modules, between 16-26 modules, between 16-41 modules, between 20-30 modules, or between 20-25 modules in length. The RVD array length may be 5 modules, 8 modules, 10 modules, 11 modules, 12 modules, 13 modules, 14 modules, 15 modules, 16 modules, 17 modules, 18 modules, 19 modules, 20 modules, 22 modules, 25 modules or 30 modules.

a. Dystrophin

Dystrophin is a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane. The dystrophin gene is 2.2 megabases at locus Xp21. The primary transcription measures about 2,400 kb with the mature mRNA being about 14 kb. 79 exons code for the protein which is over 3500 amino acids. Normal skeleton muscle tissue contains only small amounts of dystrophin but its absence of abnormal expression leads to the development of severe rind incurable symptoms. Some mutations in the dystrophin gene lead to the production of defective dystrophin and severe dystrophic phototype in affected patients. Some mutations in the dystrophin gene lead to partially-functional dystrophin protein and a much milder dystrophic phenotype in affected patients.

DMD is the result of inherited or spontaneous mutations that cause nonsense or frame shift mutations in the dystrophin gene. Naturally occurring mutations and their consequences are relatively well understood for DMD. It is known that in-frame deletions that occur in the exon 45-55 region contained within the rod domain can produce highly functional dystrophin proteins, and many carriers are asymptomatic or display mild symptoms. Furthermore, more than 60% of patients may theoretically be treated by targeting exons in this region of the dystrophin gene. Efforts have been made to restore the disrupted dystrophin reading frame in DMD patients by skipping non-essential exons during mRNA splicing to produce internally deleted but functional dystrophin proteins. The deletion of internal dystrophin exons retain the proper reading frame but cause the less severe Becker muscular dystrophy.

b. TALENs for Dystrophin

TALENs specific for dystrophin gene are disclosed herein. The TALENs may include a nuclease and a TALE DNA-binding domain that binds to the dystrophin gene. The TALENs may bind and recognize a target region. TALEN target regions may be chosen immediately upstream of possible out-of-frame stop codons such that insertions or deletions during the repair process restore the dystrophin reading frame in either disrupted frame.

The TALE domain may bind to a nucleic acid sequence of SEQ ID NOs: 16-46, 50, 52, 58, or 59, or a complement thereof. The TALEN may include an amino acid sequence selected from the group consisting of SEQ ID NO: 1-15, or a complement thereof. The nuclease may be FokI. For example, the disclosed TALENs were engineered to mediate highly efficient gene editing at exon 51 and the 5' UTR of the dystrophin gene. These TALENs restored dystrophin protein expression in cells from DMD patients, including skeletal myoblasts and dermal fibroblasts that were reprogrammed to the myogenic lineage by MyoD, with no TALEN-mediated off-target changes to the protein-coding regions of the genome. The TALENs may have varying RVD array sequences and lengths. Examples of RVD arrays may be found in Table 2. The TALENS may have binding regions separated by varying spacer regions. Examples of spacer regions may be found in Table 3 as indicated as the nucleotide sequence that was not underlined.

(1) Exon 51

Exon 51 is frequently adjacent to frame-disrupting deletions in DMD and occurs in approximately 20% of all DMD patients. This class of DMD mutations is ideally suited for permanent correction by NHEJ-based genome editing and HDR. TALENs described herein have been developed for targeted modification of exon 51 in the human dystrophin gene. These TALENs were transfected into human DMD cells and mediated efficient gene modifications and conversion to the correct reading frame. Protein restoration was concomitant with frame restoration and detected in a bulk population of TALEN-treated cells.

The TALE DNA-binding domain of these TALENs may bind to a nucleic acid sequence of SEQ ID NOs: 16-24, 26-41, 46, 50, 52, 58, or 59, or a complement thereof. The TALEN protein may include an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13, or a complement thereof. The nuclease may be FokI.

(2) 5' UTR

TALENs described herein have been developed for targeted modification of the 5' untranslated region (UTR) of the human dystrophin gene. TALENs engineered to target the 5' UTR of the dystrophin gene allows the integration of a replacement dystrophin gene, such as a full-functional dystrophin gene or a minidystrophin expression cassette, to be under the control of the endogenous promoter and regulatory sequences in the normal chromosomal context. Targeting the gene region upstream of the dystrophin coding sequence thereby allows tissue-specific expression of the dystrophin protein at physiologic expression levels. This approach may be used to treat all of the possible mutations within the dystrophin-encoding sequence.

These TALENs may include a nuclease and a TALE DNA-binding domain that binds to 5' UTR of the human dystrophin gene. The TALE DNA-binding domain may bind to a nucleic acid sequence of SEQ ID NOs: 25 or 42-45, or a complement thereof. The TALEN protein may include an amino acid sequence selected from the group consisting of SEQ ID NO: 14 and SEQ ID NO: 15, or a complement thereof. The nuclease may be FokI.

3. Compositions

The present disclosure also provides compositions of two or more TALENs, as described above. These compositions may be used in genome editing. The composition includes a first TALEN, which binds to a first binding region, and a second TALEN, which binds to a second binding region. The first binding region and second binding region are located within a target region or the target gene. The first binding region and second binding region are not the same;

the first TALEN binds to a binding region that is different binding region from where the second TALEN binds. The binding regions are separated by at least one base pair. The spacer region between the binding regions of the target region may be between 1-30 bp, between 1-25 bp, between 1-20 bp, between 1-15 bp, between 5-30 bp, between 5-25 bp, between 5-20 bp, between 5-15 bp, between 7-25 bp, between 7-23 bp, between 7-20 bp, between 10-30 bp, between 10-25 bp, between 10-20 bp, between 10-15 bp, between 14-25 bp, between 14-19 bp, between 15-30 bp, between 15-25 bp, between 15-20 bp, between 20-30 bp, or between 20-25 bp, in length. The spacer region may be 5 bp, 10 bp, 11 bp, 12 bp, 13 bp, 14 bp, 15 bp, 16 bp, 17 bp, 18 bp, 19 bp, 20 bp, 21 bp, 22 bp, 23 bp, 24 bp, 25 bp, or 30 bp in length.

The two or more TALEN protein may be selected from TALEN proteins that include an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15, or a complement thereof. The composition may include two TALEN proteins having respectively the amino acid sequence of: SEQ ID NO: 1 and SEQ ID NO: 3; SEQ ID NO: 1 and SEQ ID NO: 4; SEQ ID NO: 1 and SEQ ID NO: 8; SEQ ID NO: 1 and SEQ ID NO: 9; SEQ ID NO: 1 and SEQ ID NO: 11; SEQ ID NO: 1 and SEQ ID NO: 13; SEQ ID NO: 2 and SEQ ID NO: 3; SEQ ID NO: 2 and SEQ ID NO: 4; SEQ ID NO: 2 and SEQ ID NO: 8; SEQ ID NO: 2 and SEQ ID NO: 9; SEQ ID NO: 2 and SEQ ID NO: 11; SEQ ID NO: 2 and SEQ ID NO: 13; SEQ ID NO: 5 and SEQ ID NO: 3; SEQ ID NO: 5 and SEQ ID NO: 4; SEQ ID NO: 5 and SEQ ID NO: 8; SEQ ID NO: 5 and SEQ ID NO: 9; SEQ ID NO: 5 and SEQ ID NO: 11; SEQ ID NO: 5 and SEQ ID NO: 13; SEQ ID NO: 6 and SEQ ID NO: 3; SEQ ID NO: 6 and SEQ ID NO: 4; SEQ ID NO: 6 and SEQ ID NO: 8; SEQ ID NO: 6 and SEQ ID NO: 9; SEQ ID NO: 6 and SEQ ID NO: 11; SEQ ID NO: 6 and SEQ ID NO: 13; SEQ ID NO: 7 and SEQ ID NO: 3; SEQ ID NO: 7 and SEQ ID NO: 4; SEQ ID NO: 7 and SEQ ID NO: 8; SEQ ID NO: 7 and SEQ ID NO: 9; SEQ ID NO: 7 and SEQ ID NO: 11; SEQ ID NO: 7 and SEQ ID NO: 13; SEQ ID NO. 10 and SEQ ID NO: 3; SEQ ID NO: 10 and SEQ ID NO: 4; SEQ ID NO: 10 and SEQ ID NO: 8; SEQ ID NO: 10 and SEQ ID NO: 9; SEQ ID NO: 10 und SEQ ID NO: 11; SEQ ID NO: 10 and SEQ ID NO: 13; SEQ ID NO: 12 and SEQ ID NO: 3; SEQ ID NO: 12 and SEQ ID NO: 4; SEQ ID NO: 12 and SEQ ID NO: 8; SEQ ID NO: 12 and SEQ ID NO: 9; SEQ ID NO: 12 and SEQ ID NO: 11; SEQ ID NO: 12 and SEQ ID NO: 13; or SEQ ID NO: 14 and SEQ ID NO: 15.

4. Methods of Correcting a Mutant Gene and Treating a Subject

The parent disclosure also provides methods of correcting a mutant gene in a cell and treating a subject suffering from a genetic disease, such as DMD. The method may include administering to a cell or subject a TALEN protein, a polynucleotide or vector encoding said TALEN protein, or composition of TALENs as described above. The method may include administering a first TALEN, which binds to a first binding region, and a second TALEN, which binds to a second binding region. The first binding region and second binding region are located within a target region or the target gene. The first binding region and second binding region are not the same; the first TALEN binds to a binding region that is different binding region from where the second TALEN binds. The binding regions are separated by at least one base pair. The spacer region between the binding regions of the target region may be between 1-30 bp, between 1-25 bp, between 1-20 bp, between 1-15 bp, between 5-30 bp, between 5-25 bp, between 5-20 bp, between 5-15 bp, between 7-25 bp, between 7-23 bp, between 7-20 bp, between 10-30 bp, between 10-25 hp, between 10-20 bp, between 10-15 bp, between 14-25 bp, between 14-19 bp, between 15-30 bp, between 15-25 bp, between 15-20 bp between 20-30 bp, or between 20-25 bp in length. The spacer region may be 5 bp, 10 bp, 11 bp, 12 bp, 13 bp, 14 bp, 13 bp, 16 bp, 17 bp, 18 bp, 19 bp, 20 bp, 21 bp, 22 bp, 23 bp, 24 bp, 25 bp, or 30 bp in length. The two or more TALEN protein may be selected from the TALEN proteins described above. The method may involve homology-directed repair or non-homologous end joining.

a. Homology-Directed Repair

As described herein, the inventors show restoration of protein expression from an endogenous mutated gene using a method involving homology-directed repair. The method as described above further includes administering a donor template to the cell. The donor template may include a nucleotide sequence encoding a full-functional protein or a partially-functional protein. For example, the donor template may include a miniaturized dystrophin construct, termed minidystrophin ("minidys") or a full-functional dystrophin construct for restoring a mutant dystrophin gene.

b. Nuclease Mediated Non-Homologous End Joining

As described herein, the inventors show restoration of protein expression from art endogenous mutated gene through template-free NHEJ-mediated DNA repair. In contrast to a transient method targeting the target gene RNA, the correction of the target gene reading frame in the genome by transiently expressed TALENs may lead to permanently restored target gene expression by each modified cell and all of its progeny.

Nuclease mediated NHEJ gene correction may correct the mutated target gene and offers several potential advantages over the HDR pathway. For example, NHEJ does not require a donor template, which may cause nonspecific insertional mutagenesis. In contrast to HDR, NHEJ operates efficiently in all stages of the cell cycle and therefore may be effectively exploited in both cycling and post-mitotic cells, such as muscle fibers. This provides a robust, permanent gene restoration alternative to oligonucleotide-based exon skipping or pharmacologic forced read-through of stop cottons and could theoretically require as few as one drug treatment. NHEJ-based gene correction using TALENs, as well as other engineered nucleases including meganucleases and zinc finger nucleases, may be combined with other existing ex vivo and in vivo platforms for cell- and gene-based therapies, in addition to the plasmid electroporation approach described here. For example, delivery of TALENs by mRNA-based gene transfer or as purified cell permeable proteins could enable a DNA-tree genome editing approach that would circumvent any possibility of insertional mutagenesis.

c. Duchenne Muscular Dystrophy

The method, as described above, may be used for correcting the dystrophin gene and recovering full-functional or partially-functional protein expression of said mutated dystrophin gene. In some aspects and embodiments the disclosure provides a method for reducing the effects (e.g., clinical symptoms/indications) of DMD in a patient. In some aspects and embodiments the disclosure provides a method for treating DMD in a patient. In some aspects and embodiments the disclosure provides a method for preventing DMD in a patient. In some aspects and embodiments the disclosure provides a method for preventing further progression of DMD in a patient.

5. Constructs and Plasmids

The genetic constructs may comprise a nucleic acid sequence that encodes the TALEN disclosed herein. The genetic construct, such as a plasmid, may comprise a nucleic acid that encodes the TALEN. The genetic construct may be present in the cell as a functioning extrachromosomal molecule. The genetic construct may be a linear minichromosome including centromere, telomeres or plasmids or cosmids.

The genetic construct may also be part of a genome of a recombinant viral vector, including recombinant lentivirus, recombinant adenovirus, and recombinant adenovirus associated virus. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer an initiation codon, a stop codon, or a polyadenylation signal.

The nucleic acid sequences may make up a genetic construct that may be a vector. The vector may be capable of expressing the TALEN in the cell of a mammal. The vector may be recombinant. The vector may comprise heterologous nucleic acid encoding the TALEN. The vector may be a plasmid. The vector may be useful for transfecting cells with nucleic acid encoding the TALEN, which the transformed host cell is cultured and maintained under conditions wherein expression of the TALEN takes place.

Coding sequences may be optimized for stability and high levels of expression. In some instances, codons are selected to reduce secondary structure formation of the RNA such as that formed due to intramolecular bonding.

The vector may comprise heterologous nucleic acid encoding the TALEN and may further comprise an initiation codon, which may be upstream of the TALEN coding sequence, and a stop codon, which may be downstream of the TALEN coding sequence. The initiation and termination codon may be in frame with the TALEN coding sequence. The vector may also comprise a promoter that is operably linked to the TALEN coding sequence. The promoter operably linked to the TALEN coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US Patent Application Publication No. US20040175727, the contents of which are incorporated herein in its entirety.

The vector may also comprise a polyadenylation signal, which may be downstream of the TALEN. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 vector (Invitrogen, San Diego, Calif.).

The vector may also comprise an enhancer upstream of the TALEN. The enhancer may be necessary for DNA expression. The enhancer may be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector may also comprise a mammalian origin of replication in order to maintain the vector extrachromosomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector may comprise the nucleic acid sequence encoding the TALEN comprising the amino acid sequence of at least one of SEQ ID NOs:1-15

6. Pharmaceutical Compositions

The TALEN may be in a pharmaceutical composition. The pharmaceutical composition may comprise about 1 ng to about 10 mg of DNA of the TALEN or TALEN protein. The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity may include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The TALEN may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the TALEN at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA vector TALEN may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

7. Methods of Delivery

Provided herein is a method for delivering the pharmaceutical formulations, preferably TALENs, for providing genetic constructs and proteins of the TALENs. The delivery of the TALEN may be the transfection or electroporation of the TALEN as a nucleic acid molecule that is expressed in the cell and delivered to the surface of the cell. The nucleic acid molecules may be electroporated using BioRad Gene Pulser Xcell or Amaxa Nucleofector IIb devices. Several different buffers may be used, including BioRad electroporation solution, Sigma phosphate-buffered saline product # D8537 (PBS), Invitrogen OptiMEM 1 (OM), or Amaxa Nucleofector solution V (N.V.). Transfections may include a transfection reagent, such as Lipofectamine 2000.

Upon delivery of the TALEN to the cell, and thereupon the vector into the cells of the mammal, the transfected cells will express the TALEN. The TALEN may be administered to a mammal to correct the dystrophin gene in a mammal. The mammal may be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

8. Routes of Administration

The TALEN proteins and compositions may be administered to a subject by different routes including orally, parenterally, sublingually, transdermally, rectally, transmucosally, topically, via inhalation, via buccal adminstration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian may readily determine the dosing regimen and route of administration that is most appropriate for a particular animal. The TALEN proteins and compositions may be administered by traditional syringes, needleless injection devices, ("EP"), "hydrodynamic method", or ultrasound.

The vector encoding a TALEN protein may be delivered to the mammal by several technologies including DNA injection (also referred to as DNA vaccination) with and without in vivo electroporation, liposome mediated, nanoparticle facilitated, recombinant vectors such as recombinant lentivirus, recombinant adenovirus, and recombinant adeno-virus associated virus.

the nucleotide encoding a TALEN protein may be introduced into a cell to genetically correct the target gene. For example, a nucleotide encoding a TALEN protein directed towards a mutant dystrophin gene may be introduced into a myoblast cell from a DMD patient. The genetically corrected myoblast cell may be treated with MyoD to induce differentiation into fibroblasts, which may be implanted into subjects, such as the damaged muscles of a subject to verify that the corrected dystrophin protein was functional and/or to treat the subject.

9. Cell Types

Any of these delivery methods and/or routes of administration could be utilized with a myriad of cell types currently under investigation for cell-based therapies, including immortalized myoblast cells, such as wild-type and DMD patient derived lines, for example Δ48-50 DMD, C25C14 and DMD-7796 cell lines, primal DMD dermal fibroblasts, induced pluripotent stem cells, bone marrow-derived progenitors, skeletal muscle progenitors, human skeletal myoblasts from DMD patients, CD133+ cells, mesoangioblasts, and MyoD- or Pax7-transduced cells, or other myogenic progenitor cells. Immortalization of human myogenic cells may be used for clonal derivation of genetically corrected myogenic cells.

Cells may be modified ex vivo to isolate and expand clonal populations of immortalized DMD myoblasts that contain a genetically corrected dystrophin gene and are free of nuclease-introduced mutations in protein coding regions of the genome. Alternatively, transient in vivo delivery of nucleases by non-viral or non-integrating viral gene transfer, or by direct delivery of purified proteins containing cell-penetrating motifs may enable highly specific correction in situ with minimal or no risk of exogenous DNA integration.

10. Kits

Provided herein is a kit, which may be used to correct a mutated gene. The kit comprises at least one component for correcting a mutated gene and instructions for using the TALEN. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

At least one component may include at least one TALEN, as described above, that specifically binds and cleaves the mutated gene when a second TALEN is present nearby. Two or more TALENs, as described above, may be included in the kit to specifically bind and target a particular target region in the mutated gene. The TALEN may be specific for a mutated dystrophin gene, as described above. The kit may include donor DNA, as described above.

11. Examples

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present invention has multiple aspects, illustrated by the following non-limiting examples.

Example 1

Materials and Methods

Cell Culture and Transfection.

HEK293T cells were obtained from the American Tissue Collection Center (ATCC) through the Duke Cell Culture Facility and were maintained in DMEM supplemented with 10% bovine calf serum and 1% penicillin/streptomycin. Immortalized myoblasts (Mamchaoui, K. et al. *Skelet Muscle* 1, 1-11 (2011)) (one from a wild-type donor, and two Δ48-50 DMD patient derived lines) were maintained in skeletal muscle media (PromoCell) supplemented with 20% bovine calf serun (Sigma), 50 µg/ml fetuin, 10 ng/ml human epidermal growth factor (Sigma), 1 ng/ml human basic fibroblast growth factor (Sigma), 10 µg/ml human insulin (Sigma), 1% GlutaMAX (Invitrogen), and 1% penicillin/streptomycin (Invitrogen). Primary DMD dermal fibroblasts were obtained from the Coriell Cell repository (GM05162A, Δ46-50) and maintained in DMEM supplemented with 10% fetal bovine serum, 1 ng/mL human bask fibroblast growth factor, and 1% penicillin/streptomycin. All cell lines were maintained at 37° C. and 5% $CO_2$;

HEK293T cells were transfected with Lipofectamine 2000 (Invitrogen) according to the manufacturer's protocol in 24 well plates. Immortalized myoblasts and primary fibroblasts were transacted by electroporation using the Gene Pulser XCell (BioRad) with PBS as an electroporation buffer using optimized conditions for each line (FIG. 1). Transfection efficiencies were measured by delivering an EGFP expression plasmid and using flow cytometry. These efficiencies were routinely ≥95% for HEK293T and ≥70% for the primary fibroblasts and immortalized myoblasts. For all experiments, the indicated mass of electroporated plasmid corresponds to the amount used for each TALEN monomer.

TALE Nuclease Assembly and Off-Target Site Prediction.

TALENs targeted to exon 51 of the human dystrophin gene were designed in silico using the TALE-NT webserver (Cermak, T. et al. *Nucleic Acid Res* 39, e82 (2011)). TALEN target sites were chosen to include half-site targets approximately 15-19 bp in length, preceded by a 5'-T (Miller, J. C, et al. *Nat Biotechnol* 29, 143-148 (2011)). Plasmids encoding these TALENs were assembled using the Golden Gate assembly method (Cermak, T. et al. *Nucleic Acids Res* 39, e82 (2011)) and standard cloning techniques into a modified pcDNA3.1 (Invitrogen) destination vector containing the Δ152/+63 TALEN architecture (Miller, J. C. et al. *Nat Biotechnol* 29, 143-148 (2011)) derived from the pTAL3 expression vector provided in the Golden Gate kit front Addgene. The FokI endonuclease domains were codon optimized and contained the ELD/KKR obligate heterodimer (Doyon, Y. et al. *Nat Methods,* 8, 74-79 (2010)) and Sharkey mutations (Guo, J. et al. *J Mol Biol* (2010)) as described previously (Perez-Pinera, P. et al. *Nucleic Acids Res* 40, 3741-3752 (2012)). Complete sequences, including TN3/8 sequences, are provided in FIG. 2. Potential off-target sites for TALEN pairs, including TN3/8, in the human genome were predicted in silico using the Paired Target Finder tool on the TALE-NT 2.0 webserver (Doyle, E. L. et al. *Nucleic Acids Res* 40, W117-122 (2012)). All predicted off-target sites were scanned using the following parameters: recommended score cutoff (3.0) spacers of range 12-23 bp, and upstream base set to "T only". Valid likely potential off-target sites were only considered, as those with up to 4 mismatches per TALEN half-site binding sequence (maximum of 8 mismatches per TALEN pair target site). Plasmid DNA encoding the modules that were used to construct the TALES was obtained from the Addgene non-profit plasmid repository.

Cel-I Quantification of Endogenous Gene Modification.

TALEN-induced lesions at the endogenous target site were quantified using the Surveyor nuclease assay (Guschin, D. Y. et al. *Meth Mol Biol* 649, 247-256 (2010)), which can detect mutations characteristic of nuclease-mediated NHEJ. After electroporation, cells were incubated for 3 or 10 days at 37° C. and genomic DNA was extracted using the DNeasy Blood and Tissue kit (QIAGEN). The target locus was amplified by 30 cycles of PCR with the AccuPrime High Fidelity PCR kit (Invitrogen) using primers 5'-GAGTTTG-GCTCAAATTGTTACTCTT-3' (SEQ ID NO: 60) and 5'-GGGAAATGGTCTAGGAGAGTAAAGT-3' (SEQ ID NO: 61). The resulting PCR products were randomly melted and reannealed in a PCR machine with the program: 95° C. for 240 s, followed by 25° C. for 60 s, 75° C. for 60 s, 65° C. for 60 s, 55° C. for 60 s, 45° C. for 60 s, 35° C. for 60 s, and 25° C. for 60 s with a −0.3° C./s rate between steps. Following reannealing, 8 µL of PCR product was mixed with 1 µL of Surveyor Nuclease S and 1 µL of Enhancer S (Transgenomic) and incubated at 42° C. for 1 hour. After incubation, 6 µL of digestion product was loaded onto a 10% TBE polyacrylamide gel and run at 200V tor 30 min. The gels were stained with ethidium bromide and quantified using ImageLab (Bio-Rad) by densitometry as previously described (Guschin, D. Y. et al. *Meth Mol Biol* 649, 247-256 (2010)).

Cytotoxicity Assay.

To quantitatively assess potential TALEN cytotoxicity, HEK293T cells were transfected with 10 ng of a GFP reporter and 100 ng of each nuclease using Lipofectamine 2000 according to the manufacturer's instructions (Invitrogen). The percentage of GFP positive cells was assessed at 2 and 5 days by flow cytometry. The survival rate was calculated as the decrease in GFP positive cells from days 2 to 5 and normalized to cells transfected with an empty nuclease expression vector as described (Cornu, T. I. et al. *Meth Mol Biol* 649, 237-245 (2010)).

Clone Isolation Procedure.

Immortalized DMD myoblasts were electroported with 10 µg of each TALEN plasmid (20 µg total). After 2 days, isogenic clones were isolated by clonal dilution in hypoxic conditions (5% $O_2$) to accelerate myoblast growth. Genomic DNA was extracted from clones using the QuickExtract Kit (Epicentre) and the target locus amplified by PCR using the Cel-I primers and conditions above. The resulting PCR products were either mixed with equal amounts of PCR product from untreated cells and analyzed by the Surveyor assay, as described above, or directly submitted for conventional Sanger sequencing to identity modified clones.

Viral Transduction and Forced MyoD Overexpression in Primary Fibroblasts.

300,000 fibroblasts were plated transduced in 10 cm plates with a lentiviral vector encoding a full-length human MyoD cDNA under the control of a dox-inducible promoter and a constitutive puromycin resistance cassette. Two days post-transduction, fibroblasts were selected for 6 days in 1 µg/mL puromycio (Sigma) to enrich for transduced cells.

Fibroblasts were then plated at a density of 200,000 cells in 10 cm dishes and MyoD expression was induced by adding 3 μg/mL doxycycline (Fisher Scientific) to the media, which was exchanged every two days.

Western Blot Analysis.

To assess dystrophin expression, immortalized myoblasts were differentiated into myofibers by replacing the growth medium with DMEM supplemented with 1% insulin-transferrin-selenium (Invitrogen) and 1% antibiotic antibiotic/antimycotic (Invitrogen) for 4-7 days. Fibroblasts were transdifferentiated into myoblasts by inducing MyoD overexpression and incubating the cells in DMEM supplemented with 1% insulin-transferrin-selenium (Invitrogen), 1% antibiotic/antimycotic (Invitrogen) and 3 μg/mL doxycycline for 15 days. TALEN expression was assessed at 3 days after transfecting HEK293T cells. Cells were collected and lysed in RIPA buffer (Sigma) supplemented with a protease inhibitor cocktail (Sigma) and the total protein amount was quantified using the bicinchoninic acid assay according to the manufacturer's instructions (Pierce). Samples were then mixed with NuPAGE loading buffer (Invitrogen) and 5% β-mercaptoethanol and heated to 85° C. for 10 minutes. Twenty-five micrograms of protein were separated on 4-12% NuPAGE Bis-Tris gels (Invitrogen) with MES buffer (Invitrogen). Proteins were transferred to nitrocellulose membranes for 1-2 hours in transfer buffer containing 10-20% methanol and 0.01% SDS. The blot was then blocked for 1 hour with 5% milk-TBST at room temperature. Blots were probed with the following primary antibodies: NCL-Dys2 (1:25. Leica), MANDYS8 (1:100, Sigma), GAPDH (1:5000, Cell Signaling), anti-FLAG-HRP (1:2000, Cell Signaling), or anti-myogenin F5D (1:200, Santa Cruz). Dystrophin expression was detected using MANDYS8 in DMD myoblast line 2 and the DMD fibroblast line or NCL-Dys2 its DMD myoblast line 1. TALEN expression was detected using anti-FLAG. Blots were then incubated with mouse or rabbit horseradish peroxidase-conjugated secondary ant-bodies (Santa Cruz) and visualized using the ChemiDoc chemilumescent system (BioRad) and Western-C ECL substrate (BioRad).

Immunofluorescence.

Fibroblasts were plated on cover slips in 24 well plates at a density of 30,000 cells/well and MyoD expression was induced for 15 days as described above. Cells were then fixed in 4% paraformaldehyde and blocked for 1 hour at room temperature with PBS containing 5% BSA, 2% goat serum and 0.2% Triton X-100. Cells were then stained overnight at 4° C. with MF20 (1:200, Developmental Studies Hybridoma Bank) primary antibody and then for 1 hour at room temperature with anti-mouse AlexaFluor 488 (Molecular Probes) secondary antibody. Cover slips were mounted with ProLong Gold antifade (Molecular Probes).

Exome Sequencing and Analysis.

The exomes of four clonally derived DMD myoblast lines carrying known TALEN-mediated deletions in exon 51 of the dystrophin gene, as well as the parent line for these cells, were analyzed. Genomic DNA was isolated using the DNeasy Blood and Tissue Kit (QIAGEN) and 3 μg of DNA were submitted to the Duke Institute for Genome Sciences and Policy's Genome Sequencing & Analysis Core. Illumina-compatible libraries were made and enriched for exonic regions using the SureSelect Human All Exon V4 Kit (Agilent). Five total libraries were prepared from the four treatment samples and one parental line reference sample. The libraries were indexed and sequenced on one lane of Illumina HiSeq2000 (100-bp paired-end sequencing). Bioinformatics analyses were performed by Duke Genome Sequencing & Analysis Core. The analysis pipeline includes the initial QC to remove sequencing adaptors and low quality bases to facilitate mapping. Sequence depth of targeted regions was calculated as >97% at 10× coverage, >91% at 20× coverage, and >82% for 30× coverage (Table 1). Table 1 shows the exome capture statistics. DOWT was the parent DMD myoblast cell line used as the reference sample tor analysis. DO32, DO106, DO127, and DO141 were the four clonally derived DMD myoblast lines carrying predetermined on-target NHEJ events at the exon 51 dystrophin locus.

TABLE 1

Exome capture statistics

| Sample Name | DO106 | DO127 | DO141 | DO32 | DOWT | Agilent-Human All Exon V4 |
|---|---|---|---|---|---|---|
| capture efficiency | | | | | | |
| Reads on Target | 79.33 | 79.28 | 79.27 | 75.95 | 79.35 | 75 |
| Reads On-Target +/− 100 bp | 86.84 | 88.96 | 89.15 | 86.11 | 89.15 | 85 |
| Coverage | | | | | | |
| 1x | 99.87 | 99.88 | 99.88 | 99.87 | 99.88 | 99 |
| 10x | 97.4 | 97.71 | 97.48 | 97.53 | 97.46 | 90 |
| 20x | 91.26 | 92.28 | 91.41 | 91.62 | 91.41 | 80 |
| 30x | 82.66 | 84.45 | 82.8 | 83.27 | 82.94 | |
| 50x | 63.51 | 66.35 | 63.54 | 64.35 | 63.9 | |
| 100x | 28.13 | 31.12 | 27.85 | 28.45 | 28.62 | |

Each sequencing reaction generated >64 million reads with >93% of reads above a quality score of 30 and an overall mean quality score of >36.4. High quality reads were mapped to the human reference genome (hg19) using bwa 0.5.9. An exome capture pipeline developed at the Duke Sequencing Core was used to assess Site exome capture efficiency. Picard v1.74 was used for removing PCR duplicates. The GATK (v1.6-13) toolkit was used tor variant calling, read realignment around INDELs, quality score recalibration and QC filtering. The filtering step discards the variants with 1) low coverage (coverage (<30×), 2) strand-bias, 3) low SNP quality score (<50) and 4) low allelic frequency (<0.5). Each candidate point mutation or INDEL were reviewed manually by IGV to identify false negative artifacts due to insufficient coverage of the parental line. Identical point mutations and INDELs that occurred in more than two of the four clones were verified as artifacts due to coverage of the reference parent cell line and were discarded. Common point mutations and INDELs were removed by comparing to human dbSNP135. The remaining point mutations and INDELs were annotated using Annovar and classified using a perl script written by the Duke Sequencing Core. The non-exonic point mutations were not considered. All point mutations and INDELs were individually visualized and validated on IGV. The flanking 100 bp of each validated mutation was screened for any potential sequence similarity to the TN3/8 target site using the Paired Target Finder tool on the TALE-NT 2.0 webserver using the parameters: recommended score cutoff (3.0), spacers of range 1-30 bp, and upstream base set to "T only."

Example 2

Results

Design and Validation of TALENs Targeted to the Dystrophin Gene.

Figure 3:
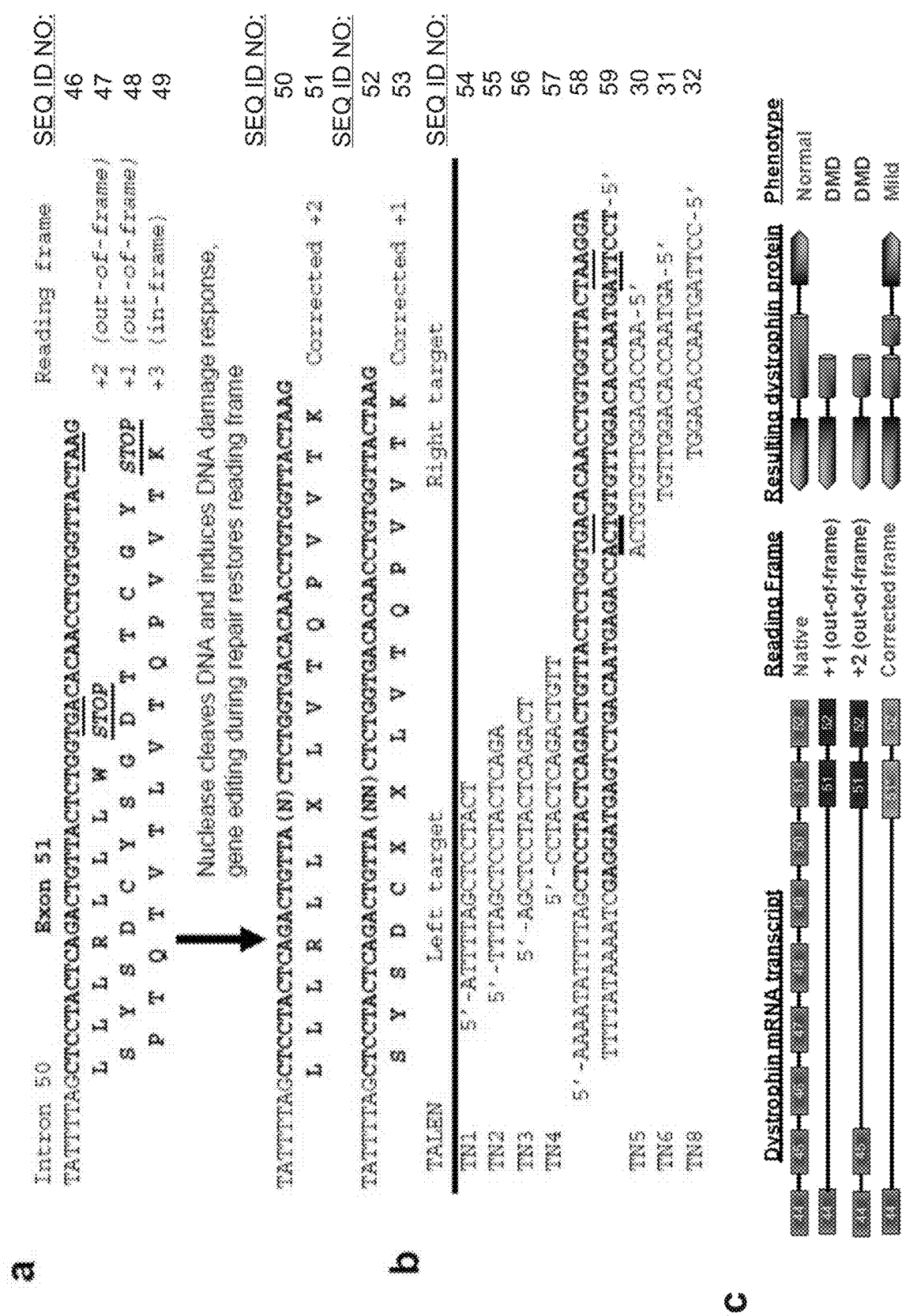
FIG. 3 shows the design of TALENs targeting exon 51 of the human dystrophin gene. (a) The possible reading frames of human dystrophin exon 51 and corresponding amino acid sequences after genome editing. (b) Combinations of TALEN pairs were designed to target immediately upstream of either out-of-frame stop codon (underline) in exon 51 (bold) of the human dystrophin gene (c) Representative genetic mutations that cause DMD and the resulting dystrophin protein are shown (deletion of exons 45-50 or 46-50). Gene editing front (a) restored the dystrophin reading frame in both types of mutations to create a functional dystrophin protein.

To evaluate TALEN-mediated genetic correction by NBEJ, several TALENs were designed to target exon 51 in the dystrophin gene. Plasmids encoding the exemplary TALENs described herein were electroporated into conditionally immortalized myoblasts (muscle cells) isolated from DMD patients. TALEN target sites were chosen immediately upstream of the two possible out-of-frame stop codons (FIG. 3a), such that insertions or deletions could restore the dystrophin reading frame in either disrupted frame. Variable lengths of spacers between TALEN monomers and TALEN RVD array lengths were tested to optimize nuclease activity (FIG. 3b, Table 2), as done previously (Miller, J. C. et al. *Nat Biotechnol* 29, 143-148 (2011).

TABLE 2

Target sequences of engineered TALENs (TN) and repeat variable diresidues (RVDs) that determine DNA-binding specificity

| | Target sequences | RVD sequence |
|---|---|---|
| TN1 | attttagctcctact (SEQ ID NO: 26) | NI NG NG NG NG NI NN HD NG HD HD NG NI HD NG |
| TN2 | tttagctcctactcaga (SEQ ID NO: 27) | NG NG NG NI NN HD NG HD HD NG NI HD NG HD NI NN NI |
| TN3 | agctcctactcagact (SEQ ID NO: 28) | NI NN HD NG HD HD NG NI HD NG HD NI NN NI HD NG |
| TN4 | cctactcagactgtt (SEQ ID NO: 29) | HD HD NG NI HD NG HD NI NN NI HD NG NN NG NG |
| TN5 | aaccacaggttgtgtca (SEQ ID NO: 30 | NI NI HD HD NI HD NI NN NN NG NG NN NG NN NG HD NI |
| TN6 | agtaaccacaggttgt (SEQ ID NO: 31) | NI NN NG NI NI HD HD NI HD NI NN NN NG NG NN NG |
| TN8 | ccttagtaaccacaggt (SEQ ID NO: 32) | HD HD NG NG NI NN NG NI NI HD HD NI HD NI NN NN NG |
| TN9 | gcaaaaacccaaaatat (SEQ ID NO: 33) | NN HD NI NI NI NI NI HD HD HD NI NI NI NI NG NI NG |
| TN10 | ttgcaaaaacccaaaat (SEQ ID NO: 34) | NG NG NN HD NI NI NI NI NI HD HD HD NI NI NI NI NG |
| TN12 | cctttttgcaaaaaccc (SEQ ID NO: 35) | HD HD NG NG NG NG NG NN HD NI NI NI NI NI HD HD HD |
| TN13 | caccagagtaacagtct (SEQ ID NO: 36) | HD NI HD HD NI NN NI NN NG NI NI HD NI NN NG HD NG |
| TN17 | gtcaccagagtaacagtct (SEQ ID NO: 37) | NN NG HD NI HD HD NI NN NI NN NG NI NI HD NI NN NG HD NG |
| TN26 | ccaaactagaaatgccat (SEQ ID NO: 38) | HD HD NI NI NI HD NG NI NN NI NI NI NG NN HD HD NI NG |
| TN27 | gaaatctgccagagcaggt (SEQ ID NO: 39) | NN NI NI NI NG HD NG NN HD HD NI NN NI NN HD NI NN NN NG |
| TN28 | ctatagatgagattatct (SEQ ID NO: 40) | HD NG NI NG NI NN NI NG NN NI NN NI NG NG NI NG HD NG |
| TN29 | agcaatgcggccatccct (SEQ ID NO: 41) | NI NN HD NI NI NG NN HD NN NN HD HD NI NG HD HD HD NG |

Figure 4:
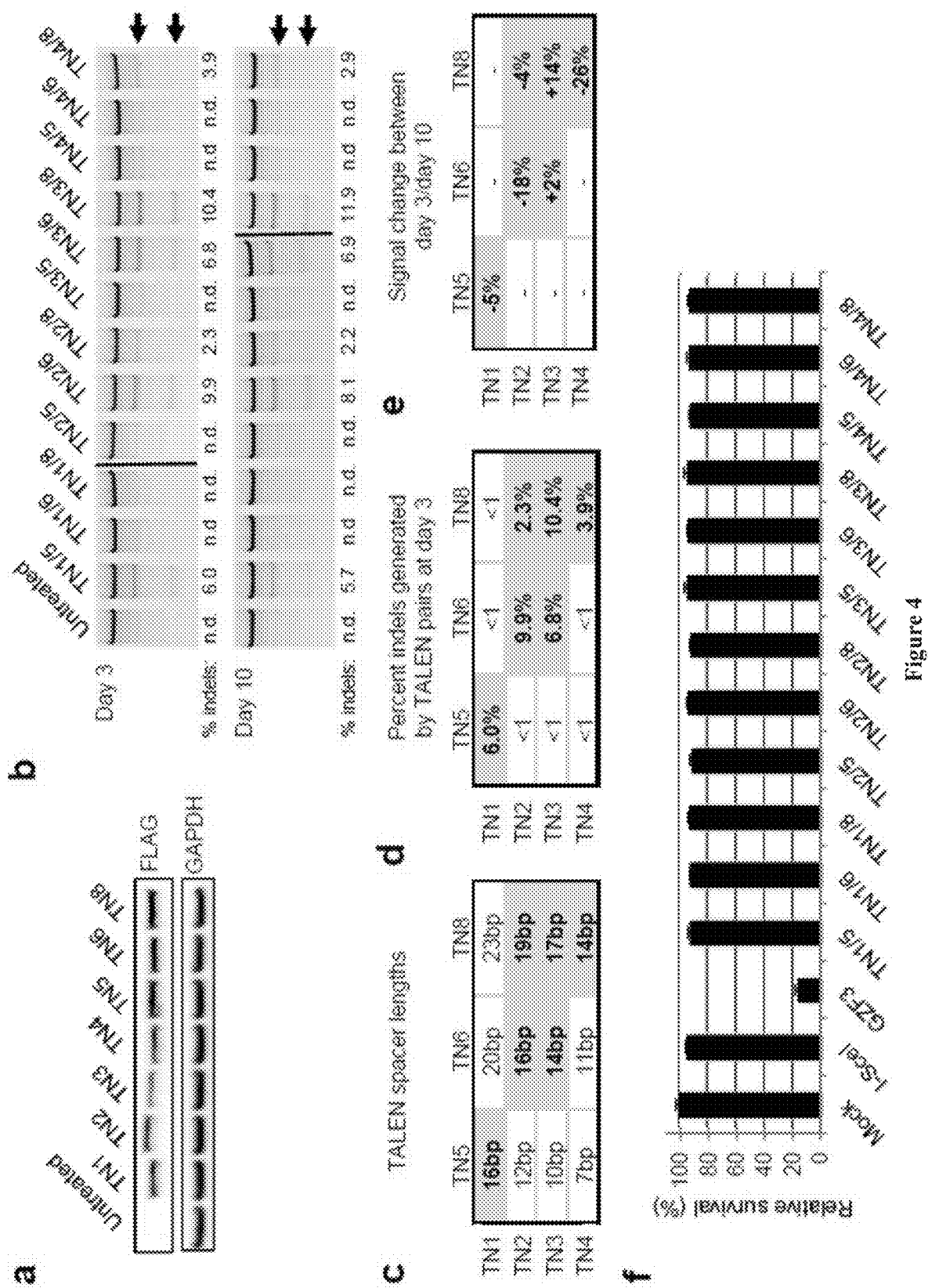
FIG. 4 shows the validation and characterization of TALENs. (a) Each TALEN construct was transfected independently into HEK293T cells to confirm full-length expression. All TALENs were approximately 95-110 kDa (b) Combinations of TALENs were co-transfected into HEK293T cells to screen for highly active TALEN pairs. Gene modification frequency was monitored at day 3 and day 10 to assess stable gene modification. Arrows denote predicted cleavage band stores indicative of NHEJ activity. (c) Summary of TALEN spacer lengths. (d) Measured gene modification rates detected by the Surveyor assay front day 3 data in (b). (e) Measured indel signal changes between day 3 and day 10 from the data in (b). (f) Cytotoxicity assay in HEK293T cells for all TALEN combinations. I-SecI is a non-toxic meganuclease and GZF3 is a zinc-finger nuclease known to be cytotoxic to human cells. "n.d." means not detected.
Figure 5:
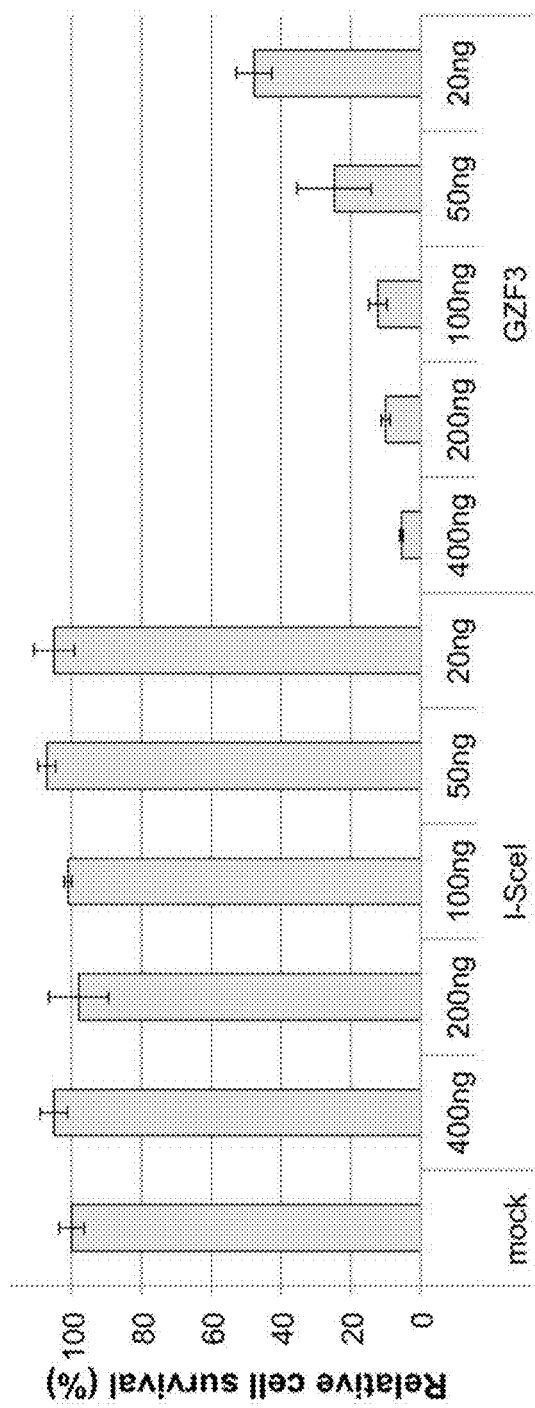
FIG. 5 shows the optimization of cytotoxicity assay using Lipofectamine 2000 in 293T cells. Varying amounts of plasmid encoding the non-toxic endonuclease I-SecI and toxic zinc-finger nuclease GZF3 were transfected into 293T cells and assessed for relative survival rates post-transfection. Based on these data, 100 ng of nuclease expression plasmid was used for the cytotoxicity studies.

Western blots confirmed full-length and robust expression of the TALENs following transfection of TALEN-encoding plasmids into HEK293T cells (FIG. 4a) All combinations of left and right TALENs were then transfected into HEK293T cells and the genomic DNA was assessed for modification by the Surveyor assay, which can detect the frequency of allelic modifications with a dynamic range of ~1-50%. Several TALENs with spacers of 14-19 bp were highly active with gene editing efficiencies exceeding modification of 10% of total, alleles (FIGS. 4b-4d). The gene editing frequencies were stable from 3 to day 10 (FIGS. 4b and 4c), confirming that these TALENs were well tolerated in human cells. Furthermore, the engineered TALENs showed minimal cytotoxicity in human cells similar to the well-characterized non-cytotoxic homing endonuclease I-SceI (FIGS. 4f and 5). TN3/8 was highly active and a well-tolerated TALEN pair and was used for subsequent experiments.

Figure 6:
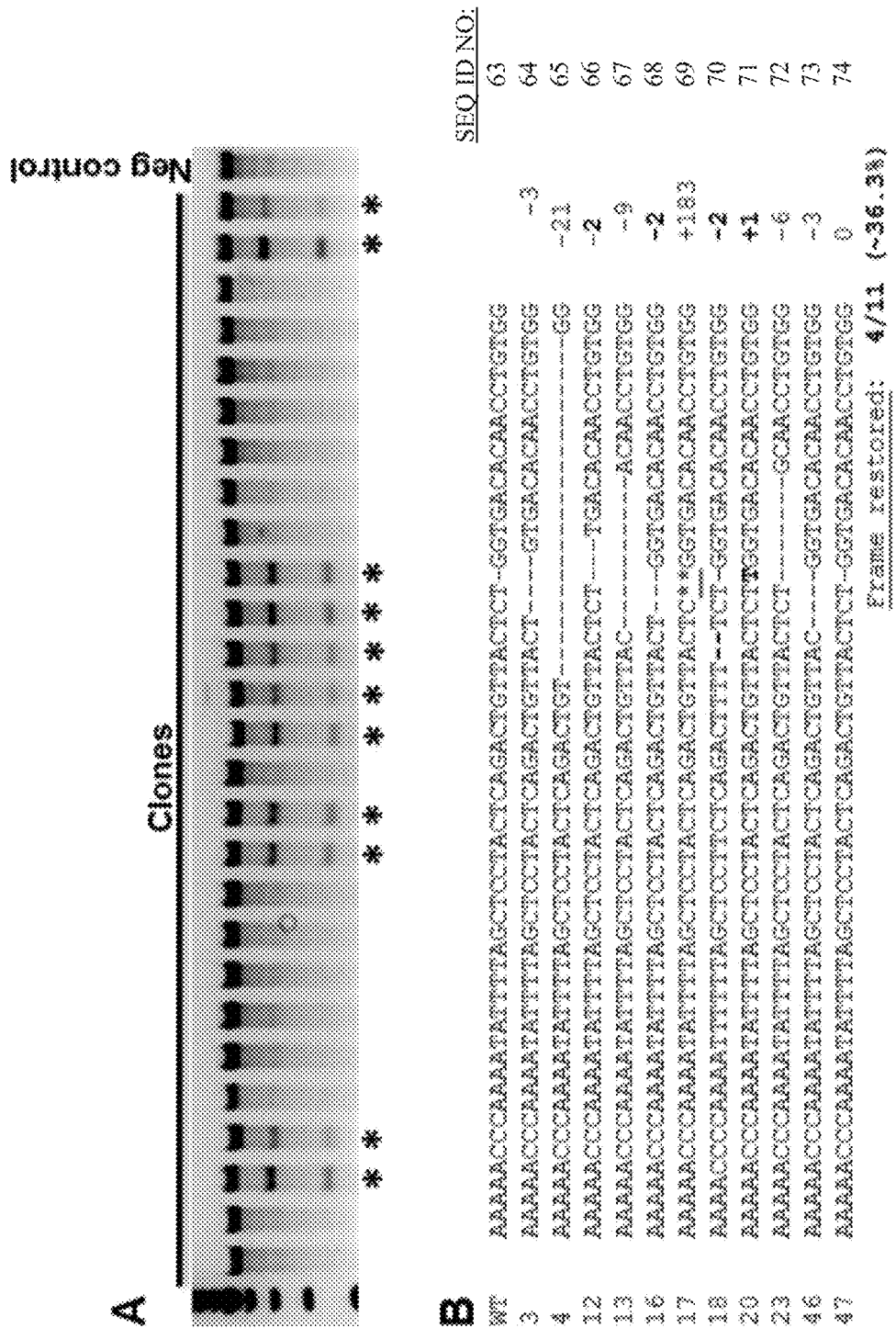
FIG. 6 shows (A) Surveyor assay to detect exon 51 gene modification in clonal cell populations of TALEN-treated DMD myoblasts. Asterisks indicate modified cells. (B) Sequences of modified clonal populations. The size of the insertion/deletion is indicated on the right. The two asterisks represent a 183 nucleotide insertion. Four of eleven modified clones (of 27 total assayed clones) showed indels that lead to reading frame correction.
Figure 9:
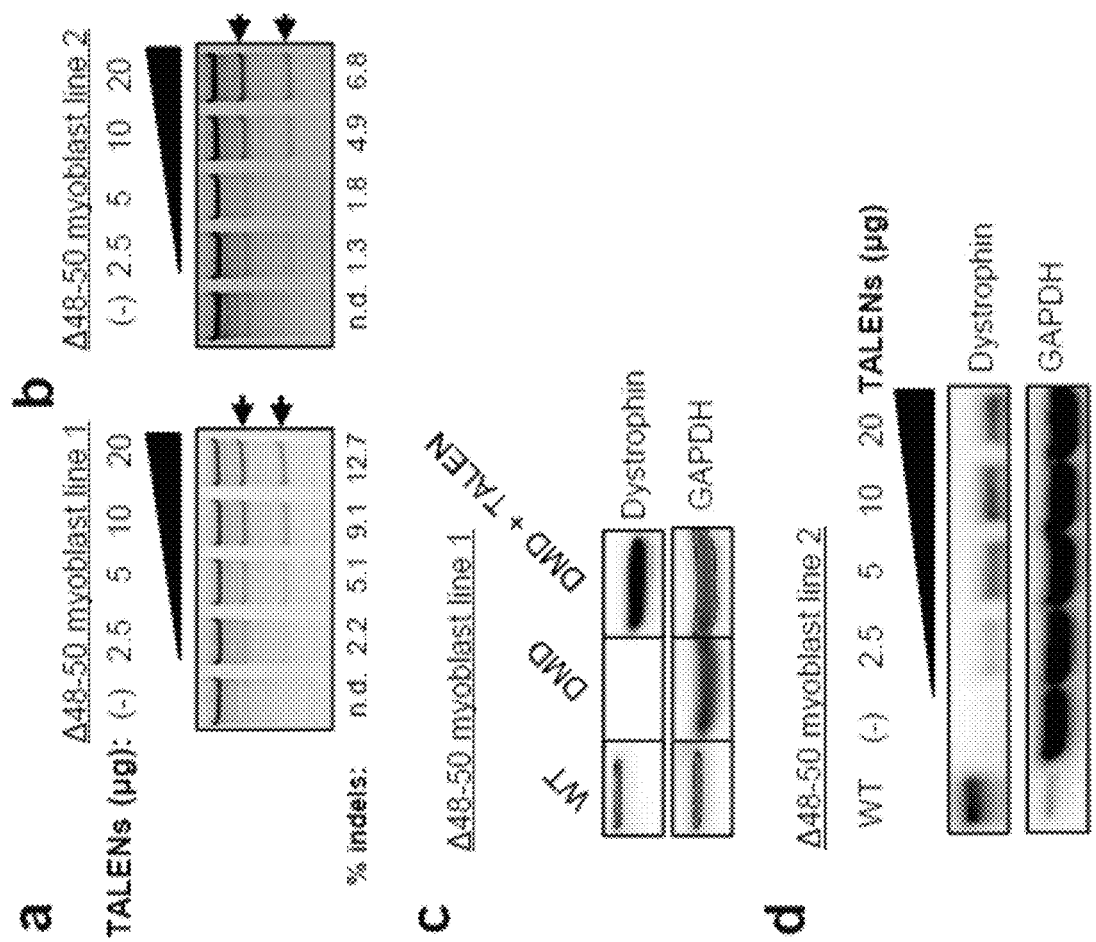
FIG. 9 shows the efficient genetic modification and protein restoration in a bulk population of cells treated with TN3/8. (a,b) Dose-dependent response of NHEJ activity with increasing amounts of TALEN pair TN3/8 measured by the Surveyor assay after transfection of the indicated amount of each TALEN plasmid into two different DMD myoblast lines, each carrying a novel deletion of exons 48-50 (Δ48-50). Arrows denote predicted cleavage band sizes indicative of NHEJ activity. (c) DMD myoblast line 1 was treated with five micrograms of each TALEN plasmid and dystrophin expression was assessed after 7 days of differentiation by western blot using the NCL-Dys2 antibody. (d) DMD myoblast 2 was treated with the indicated amount of each TALEN plasmid and dystrophin expression was assessed after 7 days of differentiation by western blot using the MANDYS8 antibody. Protein from wild-type human myoblast differentiated in parallel was diluted 1:100 and loaded as a positive control for full-length dystrophin expression (427 kDa) relative to the truncated Δ48-50 product (412 kDa).

TALEN activity in these cells was assessed by the Surveyor assay, which detects DNA cleavage and religation. This analysis showed that several TALEN pairs were active (FIGS. 6 and 9a,b). To verify that the targeted changes to exon 51 mediated by the nucleases were leading to restoration of gene expression of gene expression, dystrophin expression was determined by Western blot. Myoblasts from DMD patients harboring deletions of exons 45 through 50 were electroporated with TALENs (TN3/TN8) that target exon 51 prior to the premature stop codon. Because no homologous donor was provided, DNA repair by NHEJ to lead to small insertions and deletions (indels) was predicted. Because the size of these indels was random, one-third of the modified cells were predicted to contain indels that restored dystrophin expression. After these cells were moved to differentiation conditions, new dystrophin expression that was not present in untreated cells was detected with both an antibody recognizing the rod domain that was N-terminal of the premature truncation (MANDYS-8, Sigma) and the C-terminus (NCL-Dys2, Leica) (FIGS. 9c and 9d). Dilution of the protein lysates from the differentiated wild-type human myoblasts suggested that the level of correction achieved in the current unoptimized protocol was close to 10% (FIGS. 9c and 9d). The data demonstrated that TALEN delivery to muscle cells from DMD patients resulted in nuclease activity at the target gene (FIGS. 6, 9a, and 9b) and dystrophin protein expression in these cells (FIGS. 9c and 9d) that otherwise was not possible due to DMD mutations.

In order to further characterize the genotype and phenotype of the corrected cells, clonal cell populations were derived from the nuclease-treated human DMD myoblasts. TALEN-treated cells that showed restored dystrophin protein expression (FIGS. 9c and 9d) were clonally diluted. The exon 51 PCR product from genomic DNA of 27 clonal populations was diluted 1:1 with the same PCR product from untreated DMD cells and analyzed by the Surveyor assay, which detects mismatches between DNA sequences (FIG. 6A). Eleven of the 27 clones showed DNA sequences distinct from the untreated cells at the location of TALEN cleavage, suggesting a gene modification rate of 41% (FIG. 6A). This was significantly higher than what was detected is bulk Surveyor assays (~1015%, FIG. 4b), but was similar to what has been detected with other highly optimized nucleases. The PCR amplicons from these eleven clones were sequenced and 4 of them (36%) showed indels that would be predicted to restore the dystrophin reading frame (FIG. 6B).

These results show correction of dystrophin expression in cells front DMD patients harboring mutations that otherwise would not allow for any dystrophia expression. Although these results show correction by the random generation of indels by NHEJ gene repair in exon 51, these TALENs could be useful for gene correction via other mechanisms, such as exon deletion and gene repair by homologous recombination. Full sequences of all TALENs targeting in and around exon 51 are included in Table 2. Table 2 shows the target sequences and RVDs for TALENs. All target sequences were preceded by a prerequisite 5'T. FIG. 2 shows the amino acid sequences of engineered TALENs targeted to exon 51 of the dystrophin gene. Fok ELD-S/KKR-S refers to the FokI nuclease domain that was fused to the TALE DNA-binding domains and the RVD diresidues are underlined. Table 3 shows the target sequences of the TALEN pairs.

TABLE 3

Target sequences of the TALEN pairs.

| | |
|---|---|
| TN2/TN6 | tttagctcctactcagactgttactctggtgacacaacctgtggttact (SEQ ID NO: 16) |
| TN2/TN8 | tttagctcctactcagactgttactctggtgacacaacctgtggttactaagg (SEQ ID NO: 17) |
| TN3/6 | agctcctactcagactgttactctggtgacacaacctgtggttact (SEQ ID NO: 18) |
| TN3/TN8 | agctcctactcagactgttactctggtgacacaacctgtggttactaagg (SEQ ID NO: 19) |
| TN9/TN17 | gcaaaaacccaaaatattttagctcctactcagactgttactctggtgac (SEQ ID NO: 20) |
| TN10/TN17 | ttgcaaaaacccaaaatattttagctcctactcagactgttactctggtgac (SEQ ID NO: 21) |
| TN12/TN13 | ccttttgcaaaaacccaaaatattttagctcctactcagactgttactctggtg (SEQ ID NO: 22) |
| TN26/TN27 | ccaaactagaaatgccatcttccttgatgttggaggtacctgctctggcagatttc (SEQ ID NO: 23) |
| TN28/TN29 | ctatagatgagattatctgcccatgactggcgcagggatggccgcattgct (SEQ ID NO: 24) |

TN3/8 Mediates High Efficiency Conversion to all Three Reading Frames.

Figure 7:
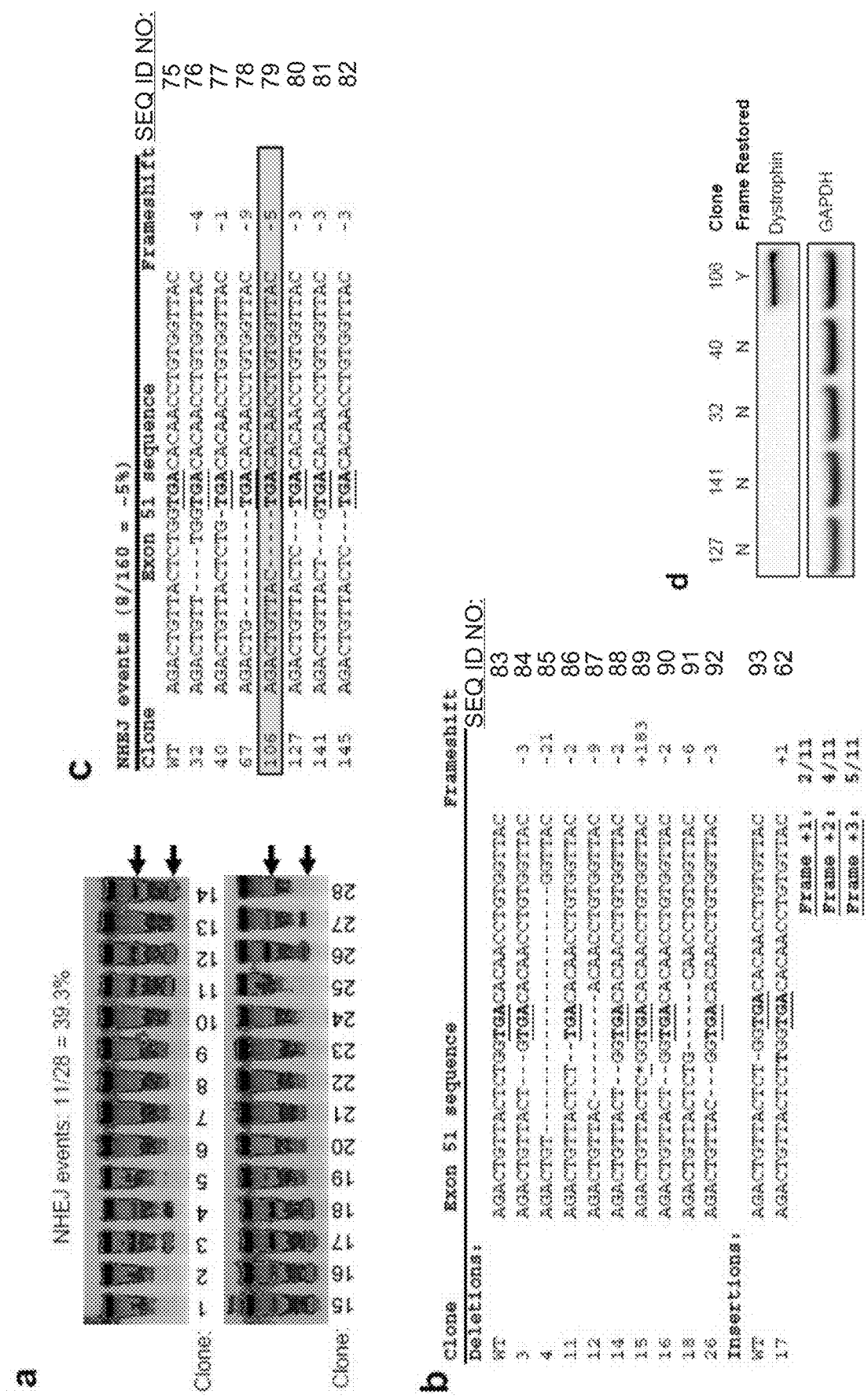
FIG. 7 shows the genetic correction of aberrant dystrophin reading frames by TALEN-mediated genome editing. (a) Isogenic clones were derived from human skeletal myoblasts treated with ten micrograms of each plasmid encoding TN3/8 and screened using the Surveyor assay to detect mutant alleles in reference to the parent (untreated) genomic DNA. Arrows denote predicted cleavage band sizes indicative of NHEJ activity, (b) Sanger sequencing of the TALEN target site in exon 51 in mutant clones identified in (a). The asterisk represents a 183 nucleotide insertion. (c) DMD human myoblast cell line 1 was treated with ten micrograms of each plasmid encoding the TN3/8 TALEN pair and isogenic clones were subsequently derived. Sanger sequencing was used to identify clones with small insertion or deletion mutations at the exon 51 genomic locus characteristic of NHEJ. Clone 106 had a 5 bp deletion that may restore the reading frame (boxed). All other clones had deletions that were not predicted to result in corrective frameshift events. (d) Clonal cell populations with NHEJ events detected at exon 51 were cultured in differentiation conditions for 7 days and analyzed by western blot for dystrophin expression at the predicted molecular weight (412 kDa).

NHEJ-based gene modification created indels of random length and may cause conversion to any of the three reading frames in an exonic sequence. To validate the overall gene modification rate and possible reading frames generated following TALEN-induced NHEJ, clonal cell populations were derived from human skeletal myoblasts that had been electroporated with TN3/8-encoding plasmids. These clones were assayed for NHEJ events occurring at the dystrophin exon 51 locus using the Surveyor assay to detect sequence differences relative to untreated cells (FIG. 7a). Eleven of 28 (39%) clonal cell populations were modified and subsequent sequencing of the alleles from these clones confirmed indels characteristic of NHEJ (FIG. 7b). Deletions were heavily favored. The random length of these indels verified that conversion to any of the three reading frames was possible. The conversion rate to any one of the three reading frames was observed to roughly proportional to ⅓ of the total NHEJ events (FIG. 7b). Interestingly, several small deletions were observed that did not alter the original reading frame, demonstrating that this approach could be used to delete aberrant stop-codons (FIG. 7b).

Reading Frame Correction Leads to Restored Protein Expression.

Whether correction of the dystrophin reading frame by TALEN-mediated NHEJ results in restored dystrophin protein expression was assessed. Immortalized human myoblasts derived from DMD patients with a frame-disrupted dystrophin gene caused by deletion of exons 48-50 (Δ48-50) were electroporated with plasmids encoding TN3/8. Clonal cell populations were isolated and screened by PCR amplification of genomic DNA and Sanger sequencing to identify indels characteristics of NHEJ. Approximately 5% of clones contained modifications in exon 51, including one clone with an NHEJ event that may correct the dystrophin reading frame (FIGS. 7c and 8). Following myogenic differentiation, restored dystrophin protein expression was detected by western blot at its predicted size (~412 kDa) only in the corrected clone, and not in clones with non-corrective NHEJ events (FIG. 7d). These data demonstrate that NHEJ events that restore the dystrophin reading frame also rescue dystrophin protein expression.

TALEN-Mediated Genetic Correction in Bulk-Treated DMD Myoblasts.

Efficient in situ frame correction in the absence of selection is a powerful use of NHEJ-based gene correction. Accordingly, the restoration of dystrophin expression in TALEN-treated bulk populations of DMD myoblast lines derived from two different patients containing different deletions of exons 48-50 in the dystrophin gene was investigated. The frequency of gene modification increased with the dose of electroporated TN3/8-encoding plasmids with indels detected in up to 12.7% and 6.8% of alleles, in the two patient lines as measured by the Surveyor assay (FIGS. 9a and 99b). Following 7 days of myogenic differentiation induced by serum removal, restored dystrophin expression was detected in the bulk cell populations at the predicted size (~412 kDa) relative to expression from wild-type cells (427 kDa) (FIGS. 9c and 9d). The increase in dystrophin protein expression with TALEN dose was concomitant with the level NHEJ events detected by the Surveyor assay.

Gene Restoration in Primary DMD Dermal Fibroblasts.

Figure 10:
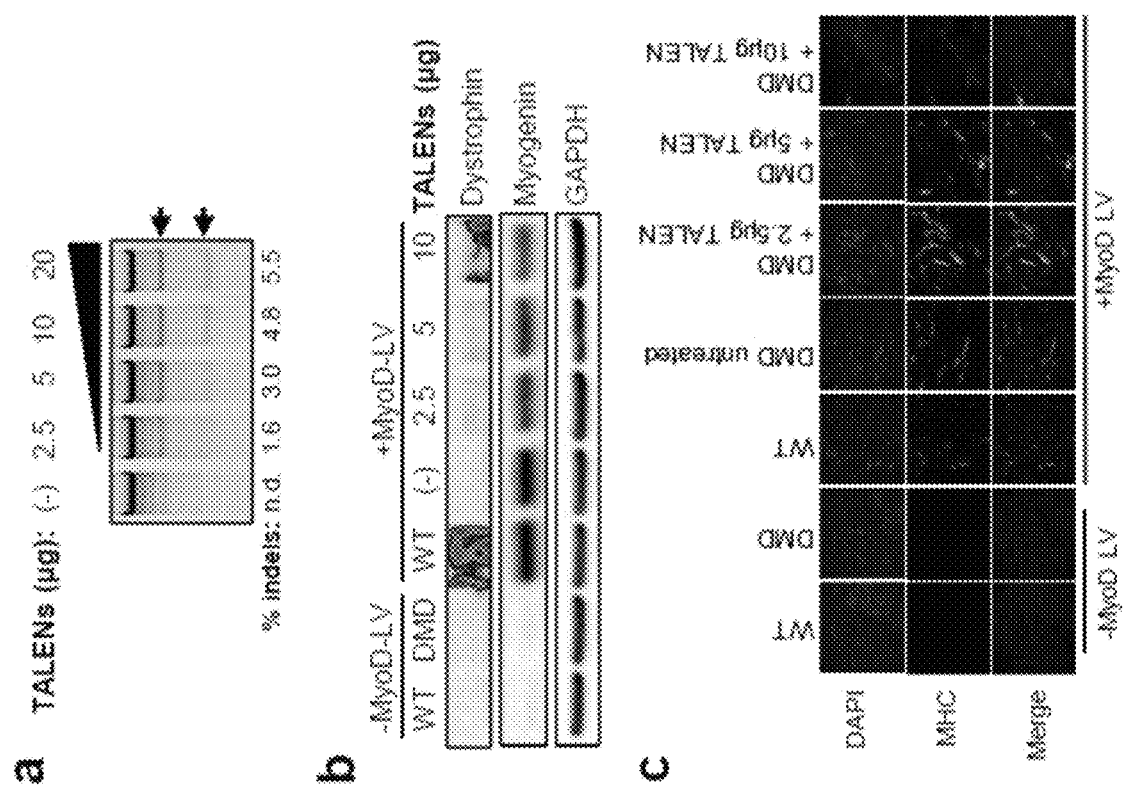
FIG. 10 shows the Dystrophin reading frame restoration in primary dermal fibroblasts. (a) Primary DMD fibroblasts carrying a deletion of exons 46-50 (Δ46-50) were electroporated with increasing doses of the indicated amount of each TALEN plasmid and gene modification rates were quantified with the Surveyor assay. Arrows denote predicted cleavage band sizes indicative of NHEJ activity. (b) Analysis of myogenin and dystrophin expression (MANDYS8) in wild-type and DMD fibroblasts after treatment with TN3/8 and 1 days of forced MyoD expression. Protein front wild-type dermal fibroblasts was included as a positive control for full-length dystrophin expression (427 kDa) relative to the truncated Δ46-50 product (400 kDa). (c) Immunofluorescence staining to detect myosin heavy chain (MHC) after MyoD expression by lentiviral gene transfer.

The simplicity of this NHEJ-based approach may enable efficient correction in proliferation-limited primary cell lines that may not be amenable to homologous recombination or selection-based gene correction. For example, DMD patient-derived primary dermal fibroblasts carrying a frame-disrupting deletion of exons 46-50 (Δ46-50) were electroporated with plasmids encoding TN3/8, resulting in high frequency gene modification in a dose-dependent manner (FIG. 10a). These treated fibroblasts were then transduced with a lentivirus expressing MyoD under an inducible promoter to stimulate transdifferentiation into the myogenic lineage and dystrophin expression. Expression of myogenin (FIG. 10b) and myosin heavy chain (FIG. 10c) confirmed efficient transdifferentiation of wild type and DMD patient fibroblasts. Rescued dystrophin expression was detected in TALEN-treated MyoD-induced fibroblasts in a dose-dependent manner at the predicted size of approximately 400 kDa (FIG. 10b), similar to the results obtained in skeletal myoblasts (FIGS. 9c and 9d).

Analysis of Off-Target Effects Induced by TN3/8.

A concern for all genome editing strategies was the potential for off-target gene modification events. TN3/8 did not show significant cytotoxicity and was well tolerated by human cells (FIGS. 4b, 4c, and 4f), suggesting specific gene targeting. Potential off-target sites were assessed in silico using the TALE-NT 2.0 Paired Target Finder Prediction webserver to scan the human genome for sequences containing up to 4 mismatches per TALEN half-site (up to 8 total mismatches per target site) separated by spacers of any length between 12 and 23 bases. This analysis did not produce any potential off-target sites that met these criteria. To further examine unpredicted off-target DNA modifications, the whole exomes of clonally derived DMD myoblasts that were previously confirmed to contain NHEJ events at the on-target exon 51 locus were sequenced (FIGS. 6d and 7c). Notably, the only insertion or deletion events characteristic of NHEJ were detected at the on-target exon 51 locus of the dystrophin gene in all four clonal lines analyzed, confirming the specificity of these TALENs (Table 1 and 4). In Table 4, "syn. SNV" refers to synonymous single nucleotide variants and "nonsyn. SNV" refers to nonsynonymous single nucleotide variants.

TABLE 4

Summary of clonal sequence variants detected by exome sequencing.

| Clone | Mutation Type | Category | AA From | AA To | Gene | Chr | Location | Ref Base | Mutant Base |
|---|---|---|---|---|---|---|---|---|---|
| 32 | Transition | syn. SNV | S | S | ANKS1B | 12 | 99201691 | C | T |
|  | Transversion | nonsyn. SNV | F | L | ZNF836 | 19 | 52659835 | G | C |
|  | Transition | syn. SNV | P | P | SASH1 | 6 | 148664242 | T | C |
|  | Transversion | syn. SNV | L | L | DAXX | 6 | 33287597 | T | G |

TABLE 4-continued

Summary of clonal sequence variants detected by exome sequencing.

| Clone | Mutation Type | Category | AA From | AA To | Gene | Chr | Location | Ref Base | Mutant Base |
|---|---|---|---|---|---|---|---|---|---|
| | Transversion | syn. SNV | L | L | CDH7 | 18 | 63525175 | T | A |
| | Deletion | frameshift | — | — | DMD | X | 31792285 | ACCAG | — |
| 106 | Transition | nonsyn. SNV | E | G | ENG | 9 | 130582267 | T | C |
| | Transition | nonsyn. SNV | N | D | CCDC36 | 3 | 49294344 | A | G |
| | Transition | syn. SNV | V | V | TARBP1 | 1 | 234556520 | C | T |
| | Transition | nonsyn. SNV | Q | R | UGT3A1 | 5 | 35988575 | T | C |
| | Transversion | nonsyn. SNV | L | I | SOWAHB | 4 | 77817679 | G | T |
| | Transversion | nonsyn. SNV | Q | P | MEF2A | 15 | 100252738 | A | C |
| | Transversion | nonsyn. SNV | R | L | RFC1 | 4 | 39306505 | C | A |
| | Transition | stopgain SNV | Q | X | ELN | 7 | 73474508 | C | T |
| | Deletion | frameshift | — | — | DMD | X | 31792285 | ACCAG | — |
| 127 | Transition | nonsyn. SNV | A | V | PLEKHH1 | 14 | 68041071 | C | T |
| | Transition | syn. SNV | P | P | RASAL2 | 1 | 178269222 | C | T |
| | Transversion | nonsyn. SNV | S | C | IGDCC4 | 15 | 65676357 | G | C |
| | Transition | syn. SNV | A | A | LMTK3 | 19 | 49001482 | G | A |
| | Transition | stopgain SNV | W | X | PLEKHS1 | 10 | 115526378 | G | A |
| | Transition | nonsyn. SNV | V | I | FAM110C | 2 | 45848 | C | T |
| | Transition | nonsyn. SNV | G | E | TRAK1 | 3 | 42251610 | G | A |
| | Transversion | syn. SNV | S | S | C15orf39 | 15 | 75499997 | A | T |
| | Transition | syn. SNV | L | L | GPBAR1 | 2 | 219127549 | C | T |
| | Deletion | nonframeshift | — | — | DMD | X | 31792284 | CAC | — |
| 141 | Transition | syn. SNV | L | L | MUC16 | 19 | 8999474 | T | C |
| | Transversion | nonsyn. SNV | F | C | RP1 | 8 | 55538286 | T | G |
| | Transversion | nonsyn. SNV | E | A | PPP1R10 | 6 | 30569808 | C | G |
| | Transition | syn. SNV | T | T | CAMKV | 3 | 49896829 | T | C |
| | Transition | syn. SNV | F | F | AK2 | 1 | 33478842 | G | A |
| | Deletion | nonframeshift | — | — | DMD | X | 31792287 | CAG | — |

Consistent with known genomic mutation rates that normally occur during clonal expansion, the exome sequencing revealed several single nucleotide variants (SNVs) in each clone relative to the parental cell line. Using the TALE-NT 2.0 Paired Target Site Prediction webserver, the immediate region around each mutation was scanned for any sequence similarity to the TN3/8 target site to determine if the TALENs could be responsible for the observed SNVs. No target sites with similarity to our TALEN target site with spacers of 1-30 bases were found in the flanking 100 bp of any SNV. Because NHEJ-mediated mutagenesis rarely results in substitutions relative to indels, the detected SNVs were likely to have arisen during clonal expansion as observed in other studies. In summary, there was no apparent off-target activity related to TALEN-mediated, NHEJ-based genetic correction in these clonally derived cells.

As shown above, the TALENs had high specificity as demonstrated by in silico analysis, cytotoxicity assays, and exome sequencing of clonally-derived modified cells.

Example 3

TALENs Targeting the 5' UTR of the Mouse and Human Dystrophin Gene

TALENs were designed to target the promoter region of the Dp427m dystrophin isoform, which has been shown to drive high expression of dystrophin in skeletal and cardiac muscle tissues. A panel of TALEN pairs was designed to optimize spacer length and gene editing activity. These TALENs were designed to target a homologous region in both mouse and human dystrophin promoter sequences to facilitate future animal studies, such as preclinical studies in a small animal model without creating a transgenic animal that carries human sequences. Combinations of TALENs were transfected into human 293T cells to assess activity by the Surveyor assay, as described above (see FIG. 11C).

One TALEN pair, TN45/50, was identified to have high activity that was stable at 3 and 10 days post-transfection (see FIG. 11A). The RVD components of TN45/50 are shown in FIG. 11B. Full amino acid sequences of engineered TALENs targeted to the 5'UTR of the dystrophin gene are provided, as TN45 (Fok-KKRS) (SEQ ID NO: 14) and TN50 (Fok-ELDS) (SEQ ID NO: 15) (see FIG. 12). Fok ELDS/KKRS refers to the FokI nuclease domain that was fused to the TALE DNA-binding domains.

10 micrograms of each plasmid encoding each of TN45 and TN50 were electroporated into human skeletal myoblasts from DMD patients. TALEN-mediated modification of the target locus was determined by the Surveyor assay three days after. As shown in FIG. 11D, the TN45/50 TALENs were active at the chromosomal locus in skeletal myoblasts from human DMD patients.

Example 4

Integration of Minidystrophin into 5'UTR of Dystrophin

Figure 13:
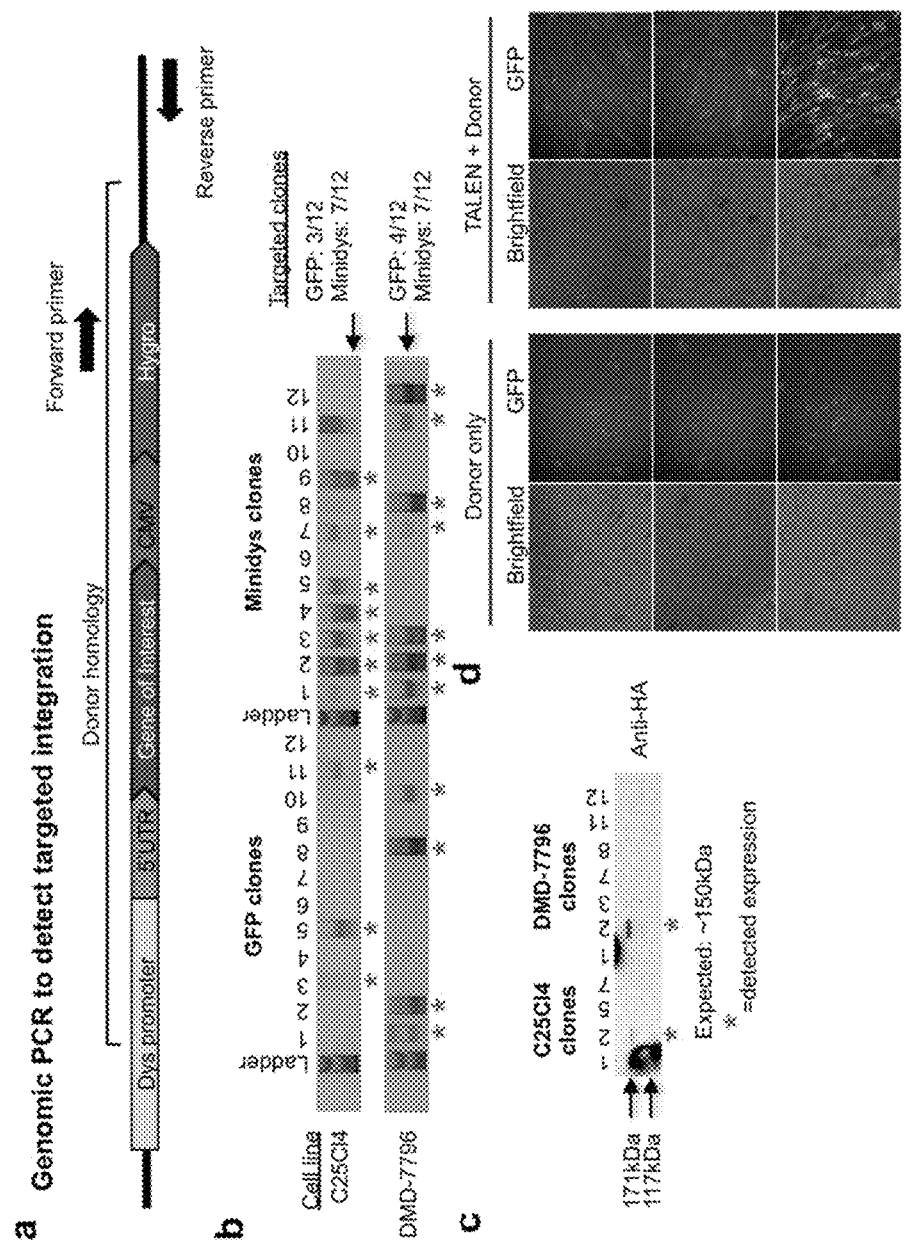
FIG. 13 shows (a) the schematic detailing PCR-based detection of targeted integration events, (b) identification of targeted clones by PCR in which a GFP or minidystrophin gene was inserted into the TALEN target site, asterisks indicate positive targeted events (c) minidystrophin expression in clones positive for targeted integration, (d) GFP expression is differentiation conditions in selected clones from treated DMD patient lines.

Functional replacement of mutated dystrophin genes may be accomplished by expression of a miniaturized dystrophin construct, termed minidystrophin ("minidys") (Wang et al. *Proc Natl Acad Sci USA*. (2000) 97(25):13714-9). The dystrophin 5'UTR was targeted with TALENs (FIG. 13a) to mediate site-specific integration of minidys would be under control of the endogenous dystrophin promoter. GFP was targeted to the 5' UTR of the dystrophin gene by co-transfecting DMD patient myoblasts with the TN45/50 TALEN pair and a donor construct containing the GFP transgene with a selection marker. Results indicated that integration of a gene encoding GFP into the 5'UTR resulted in robust expression from the endogenous promoter in many targeted clones following myogenic differentiation (FIG. 13b,d). Similarly, DMD patient myoblast clones, C25C14 and DMD-7796 (provided by Vincent Mouly, Université Pierre et Marie Curie, Paris, France), were generated with TALEN-mediated integration of a construct containing the minidystrophin gene and a selection marker at the 5'UTR. As with the GFP construct, minidystrophin expression was detected only in targeted clones by western blot (FIG. 13b, c).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. An engineered transcription activator-like effector nuclease (TALEN) protein that binds to a dystrophin gene, wherein the TALEN protein binds upstream from a premature stop codon on the dystrophin gene, downstream from a premature stop codon on the dystrophin gene, a region in exon 51 of the dystrophin gene, or a region in the 5' UTR of the dystrophin gene, wherein the TALEN protein comprises an amino acid sequence selected from the group consisting of the amino acid sequence of SEQ ID NO: 11, SEQ ID NO: 12, SEQ ID NO: 13, SEQ ID NO: 14, and SEQ ID NO: 15.

2. The TALEN protein of claim 1, wherein the TALEN protein binds to a nucleotide sequence comprising one of SEQ ID NOs: 16-46, 50, 52, 58, 59, or a full-length complement thereof.

3. The TALEN protein of claim 2, wherein the TALEN protein comprises a nuclease.

4. The TALEN protein of claim 3, wherein the nuclease comprises FokI.

5. The TALEN protein of claim 1, wherein the TALEN protein comprises 15-19 repeat variable diresidue (RVD) modules.

6. The TALEN protein of claim 1, wherein the dystrophin gene is a human dystrophin gene.

7. A composition comprising two or more TALEN proteins according to claim 1, wherein a first TALEN binds to a first binding region and a second TALEN binds to a second binding region, wherein the first binding region and second binding region are located within a target region and the first binding region and second binding region are not the same.

8. A method of treating a subject in need thereof having a mutant dystrophin gene, the method comprising administering to the subject the TALEN protein of claim 1.

9. The method of claim 8, wherein the subject is suffering from Duchenne muscular dystrophy.

10. A method of correcting a mutant dystrophin gene in a cell, the method comprising administering to the cell comprising a mutant dystrophin gene which comprises a frameshift mutation which causes a premature stop codon and a truncated gene product the TALEN protein of claim 1, thereby the correction restores the mutant dystrophin gene in the cell.

11. The method of claim 10, wherein the correction of the mutant dystrophin gene comprises homology-directed repair.

12. The method of claim 11, further comprising administering to the cell a donor DNA.

13. The method of claim 10, wherein the correction of the mutant dystrophin gene comprises nuclease mediated non-homologous end joining.

14. A method of correcting a mutant gene in a cell, the method comprising administering to the cell containing a mutant gene that has a mutation which causes a premature stop codon and a truncated gene product a first TALEN and a second TALEN, wherein the first TALEN binds to a first binding region and a second TALEN binds to a second binding region, wherein said TALENS are selected from the TALENS of claim 1, wherein the first binding region and second binding region are located within a target region and the first binding region and second binding region are not the same, wherein the correction of the mutant gene comprises nuclease mediated non-homologous end joining, and wherein the correction restores the mutant gene.

15. The method of claim 14, wherein the method comprises administering to a cell containing a mutant dystrophin gene a first TALEN and a second TALEN, wherein the first TALEN binds to a first binding region and a second TALEN binds to a second binding region, wherein the first binding region and second binding region are located within a target region and the first binding region and second binding region are not the same.

16. A kit comprising the TALEN protein of claim 1.

* * * * *